United States Patent
Gailey et al.

[11] Patent Number: 6,113,572
[45] Date of Patent: *Sep. 5, 2000

[54] MULTIPLE-TYPE CATHETER CONNECTION SYSTEMS

[75] Inventors: Robert Nelson Gailey, Farmington; Kelly B. Powers, North Salt Lake City; Kelly J. Christian, Sandy; Kenneth Arden Eliasen, Murray; Donald James Jones, West Valley City, all of Utah

[73] Assignee: C. R. Bard, Inc., Murray Hill, N.J.

[ * ] Notice: This patent is subject to a terminal disclaimer.

[21] Appl. No.: 08/599,734

[22] Filed: Feb. 12, 1996

Related U.S. Application Data

[63] Continuation-in-part of application No. 08/449,210, May 24, 1995, Pat. No. 5,637,102.

[51] Int. Cl.[7] .................................................. A61M 11/00
[52] U.S. Cl. ........................... 604/93; 604/175; 604/536; 604/535; 285/12; 285/242; 285/259
[58] Field of Search ..................................... 604/283, 285, 604/264, 265, 93, 175, 535, 536; 285/417, 338, 12, 255, 256, 259, 242, 115

[56] References Cited

U.S. PATENT DOCUMENTS

| | | |
|---|---|---|
| 2,704,074 | 3/1955 | Butler ....................................... 128/221 |
| 3,262,721 | 7/1966 | Knight . |
| 4,257,629 | 3/1981 | Maple et al. . |
| 4,511,163 | 4/1985 | Harris et al. . |
| 4,564,222 | 1/1986 | Loker et al. ............................. 285/243 |
| 4,592,749 | 6/1986 | Ebling et al. . |
| 4,630,847 | 12/1986 | Blenkush ................................. 285/29 |
| 4,635,973 | 1/1987 | Sauer . |
| 4,790,832 | 12/1988 | Lopez . |
| 4,826,477 | 5/1989 | Adams ........................................ 604/4 |
| 4,863,439 | 9/1989 | Sanderson . |
| 4,878,900 | 11/1989 | Sundt . |
| 4,929,236 | 5/1990 | Sampson . |
| 4,946,200 | 8/1990 | Blenkush et al. . |
| 4,969,879 | 11/1990 | Lichte . |
| 5,026,344 | 6/1991 | Dijkstra et al. . |
| 5,045,060 | 9/1991 | Melsky et al. . |
| 5,049,139 | 9/1991 | Gilchrist . |
| 5,129,891 | 7/1992 | Young . |
| 5,137,529 | 8/1992 | Watson et al. ........................ 604/891.1 |
| 5,180,365 | 1/1993 | Ensminger et al. . |
| 5,312,337 | 5/1994 | Flaherty et al. . |
| 5,356,381 | 10/1994 | Ensminger et al. . |
| 5,360,407 | 11/1994 | Leonard . |
| 5,360,418 | 11/1994 | Weilbacher et al. . |
| 5,387,192 | 2/1995 | Glantz et al. . |
| 5,399,168 | 3/1995 | Wadsworth, Jr. et al. . |
| 5,405,339 | 4/1995 | Kohnen et al. . |
| 5,423,776 | 6/1995 | Haindl . |
| 5,637,102 | 6/1997 | Tolkoff et al. ........................... 604/283 |

FOREIGN PATENT DOCUMENTS

| | | |
|---|---|---|
| 0343910 | 11/1989 | European Pat. Off. . |
| 0537892 | 4/1993 | European Pat. Off. . |
| 2199391 | 4/1974 | France . |
| 2703593 | 10/1994 | France . |
| 1933802 | 1/1970 | Germany . |
| 2949315 | 7/1980 | Germany . |
| 1492162 | 7/1989 | U.S.S.R. . |
| 1269405 | 4/1972 | United Kingdom . |
| 2257764 | 1/1993 | United Kingdom . |
| 9317269 | 9/1993 | WIPO . |

*Primary Examiner*—Mark Bockelman
*Attorney, Agent, or Firm*—Trask, Britt & Rossa

[57] ABSTRACT

A catheter connection system is defined by a rigid, tubular stem attached at a proximal end thereof to a medical device. The stem has a plurality of engagement barbs encircling and radially, outwardly extending on an exterior surface of the stem. The engagement barbs can be configured having a variety of different sizes and positions. A locking barb also encircles and radially, outwardly extends on the surface of the stem between the medical device and the engagement barbs. A variety of fastening assemblies are provided for inwardly compressing a portion of a body wall of a selected catheter against the engagement barbs on the stem, when the stem is received in the lumen of the selected catheter. The fastening assemblies create a mechanical joinder and liquid-tight seal between the selected catheter and the stem. The selected catheter can be chosen from one of three or more catheters each having a combination of size and material composition distinct from the other of the catheters.

120 Claims, 24 Drawing Sheets

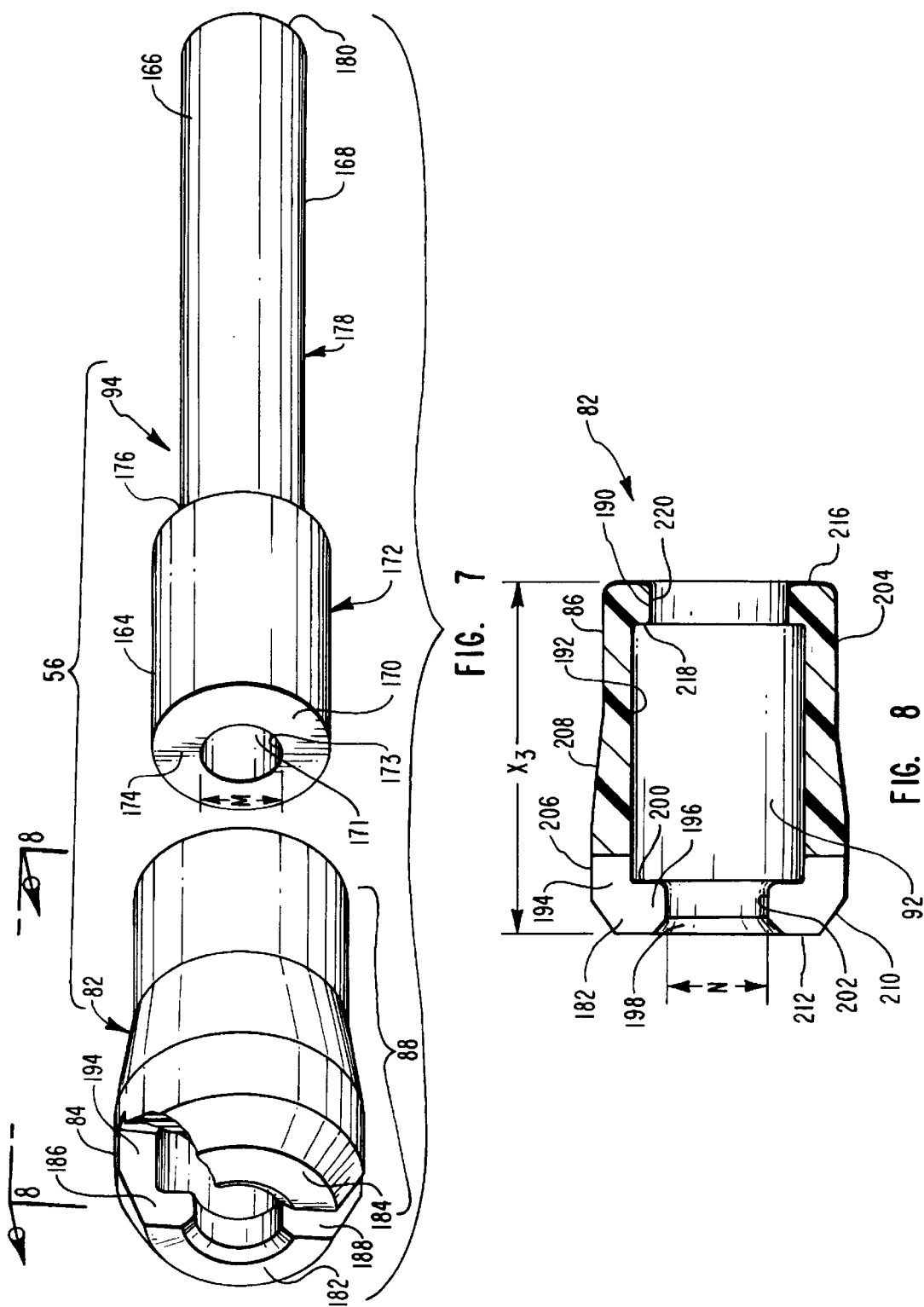

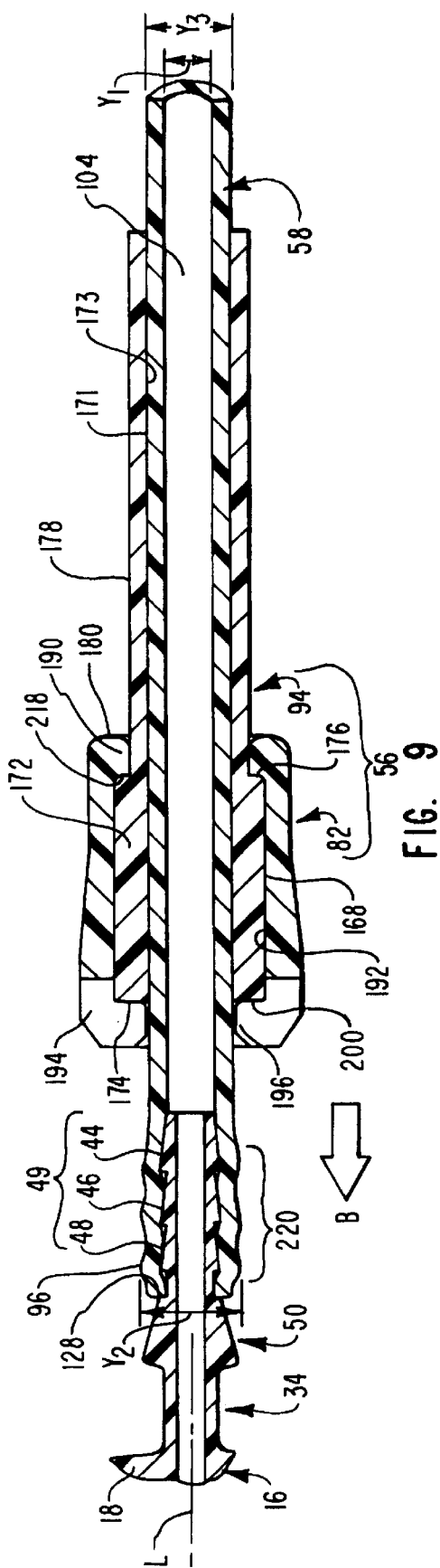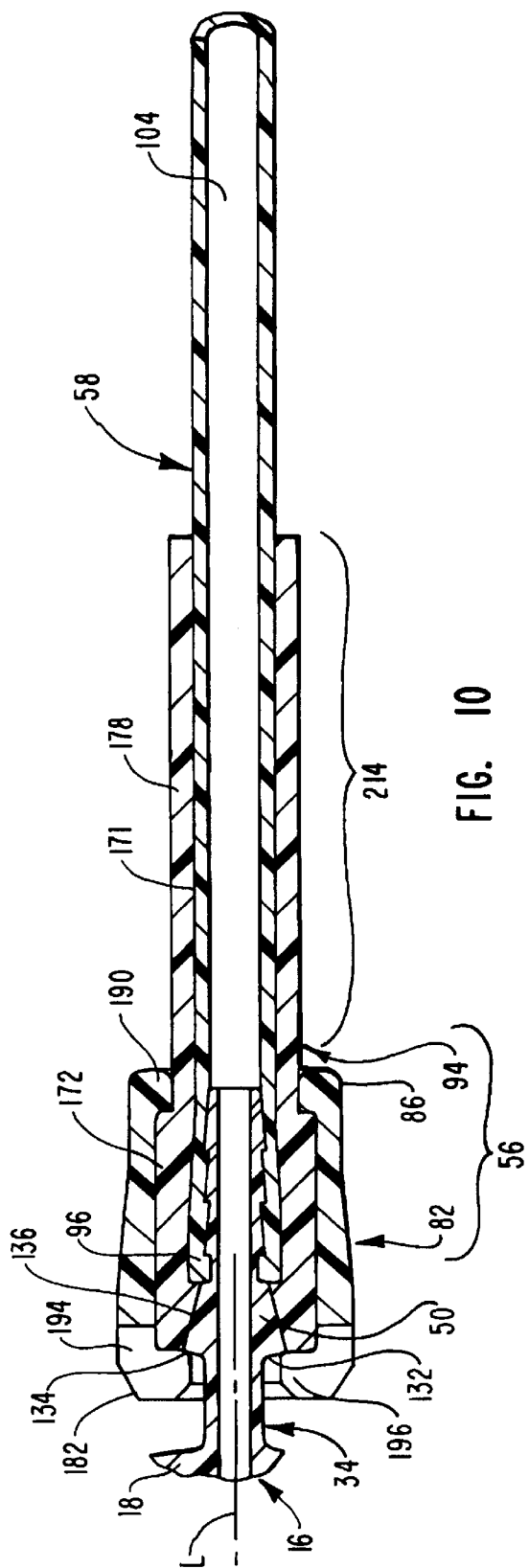

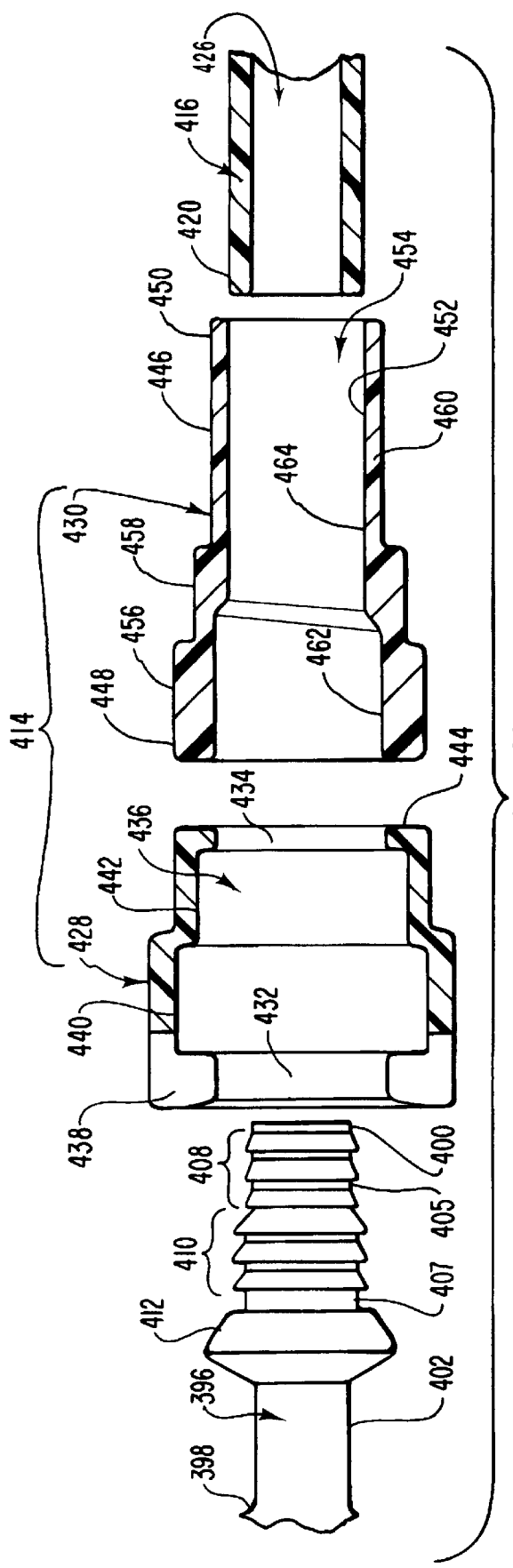
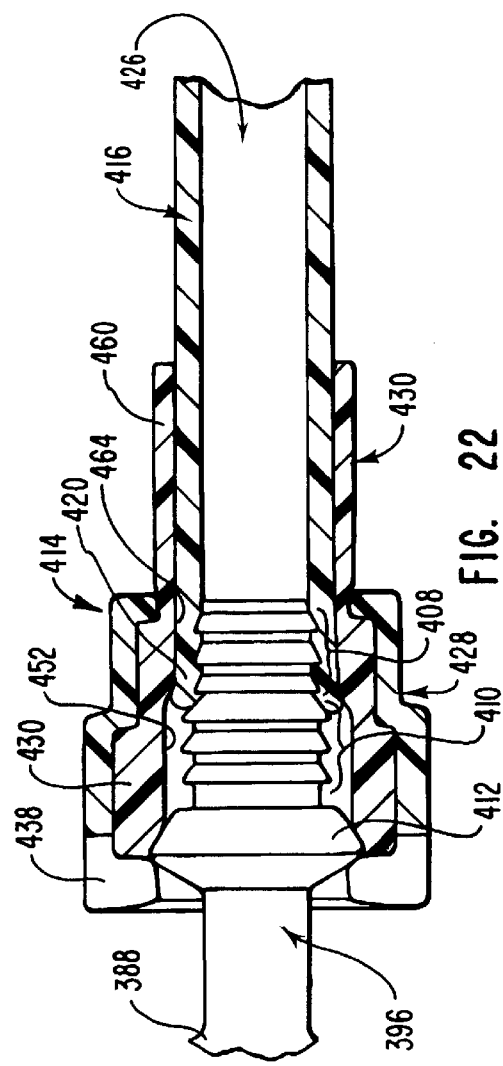
FIG. 21
FIG. 22

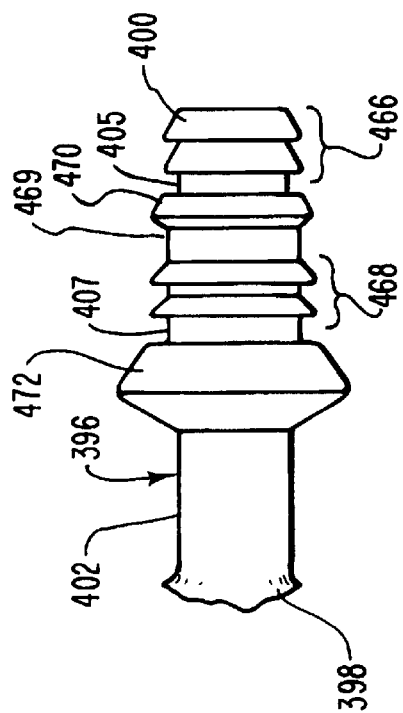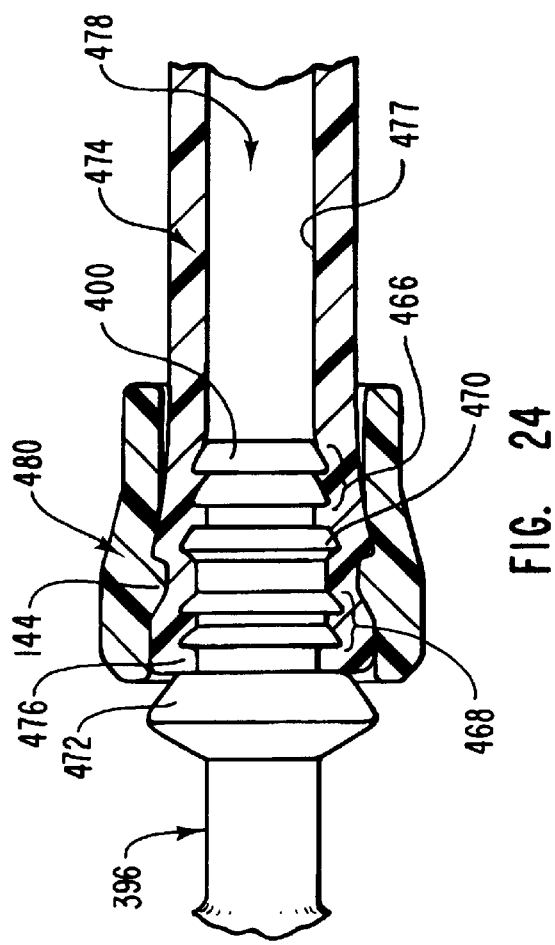

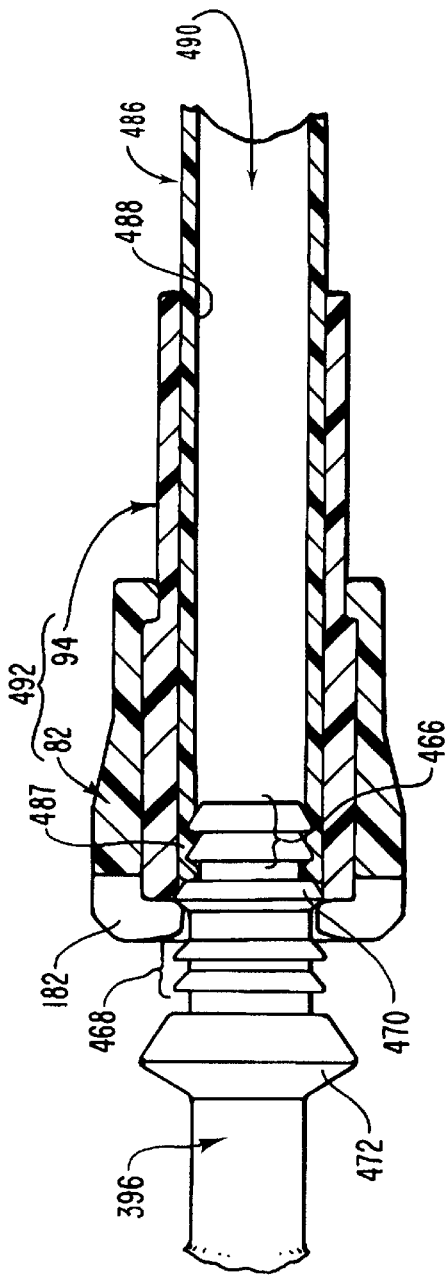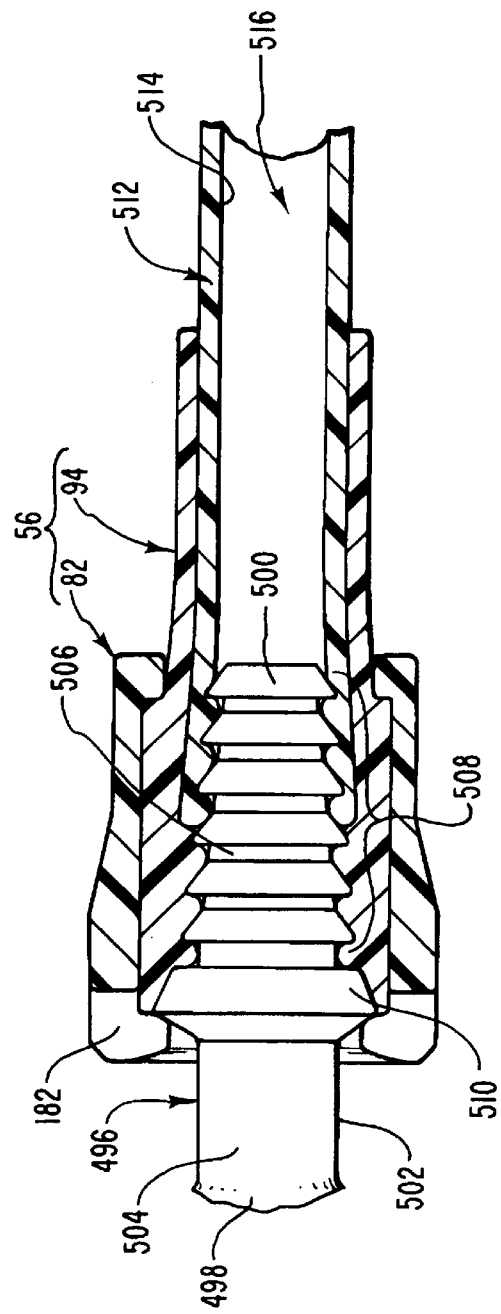

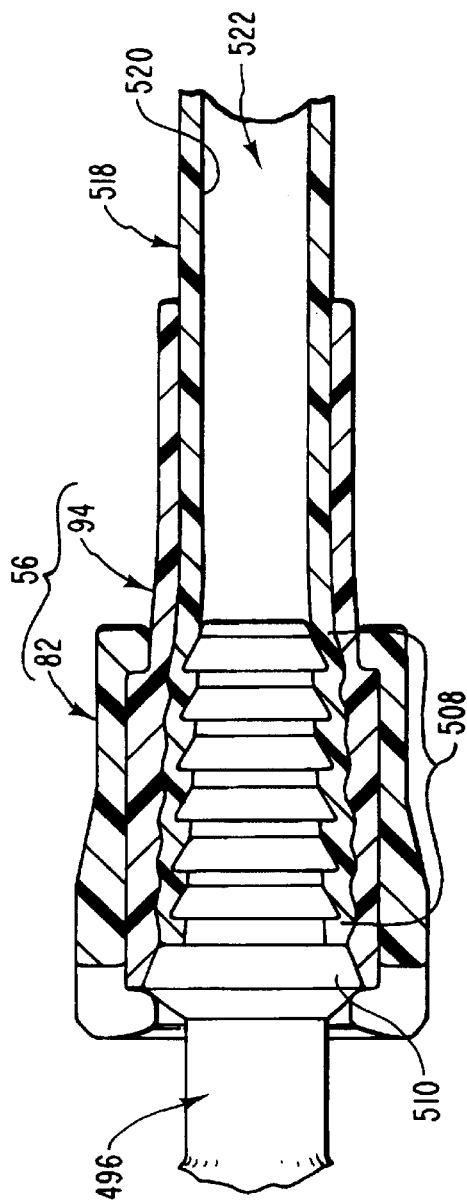
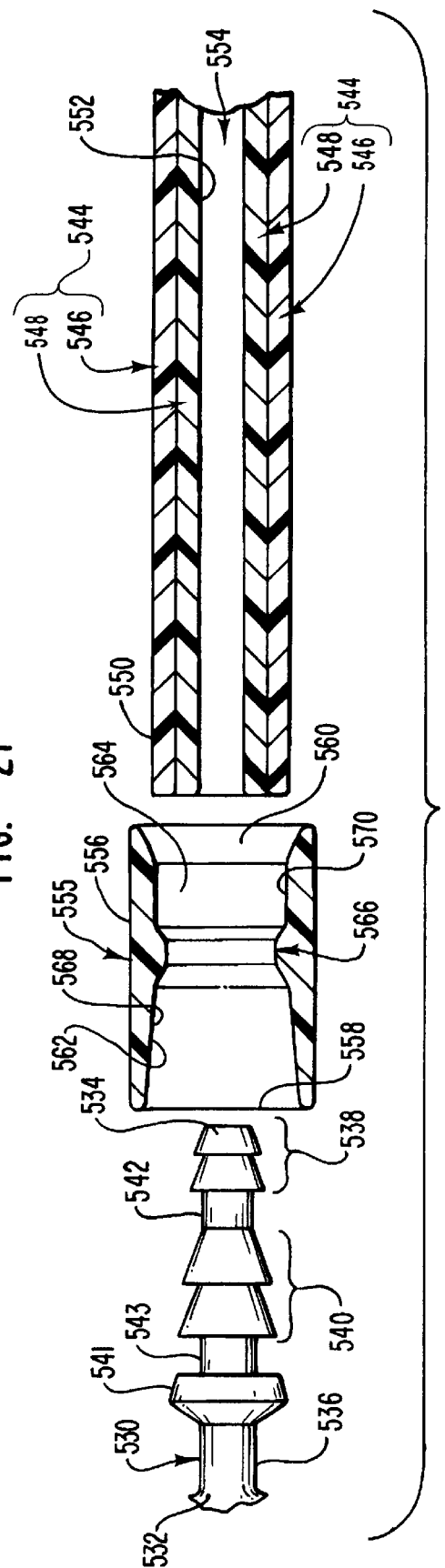

MULTIPLE-TYPE CATHETER CONNECTION SYSTEMS

RELATED APPLICATIONS

This application is a continuation-in-part of U.S. Pat. No. 5,637,102 that issued on Jun. 10, 1998, from U.S. patent application Ser. No. 449,210 filed on May 24, 1995.

BACKGROUND OF THE INVENTION

1. The Field of the Invention

The present invention relates to systems for attaching flexible catheters to medical devices.

2. Background Art

Catheters are used extensively in the medical field to facilitate the performance of recurrent therapeutic tasks inside the body of patients.

For example, using only a relatively small incision, a catheter can be implanted in the body of a patient and used to deliver fluid directly to a predetermined location, either within the cardiovascular system, the peritoneal cavity, or some organ, such as the stomach, the heart, the liver, the brain, or the reproductive tract. Alternatively or in addition thereto, such implanted catheters can be used to periodically sample from these locations, to drain fluids to relieve pressure, to withdraw fluids for extracorporeal processing on an ongoing basis, or to monitor internal body conditions, such as pressure, temperature, or fluid flow rates.

Catheters are, however, fabricated in various structural configurations, depending upon the intended use for each.

A common catheter design used in performing many of the procedures mentioned above includes an elongated, flexible cylindrical catheter body having a fluid flow passageway or a lumen extending along the interior of that catheter body. During use, an end of the catheter referred to as the distal end is inserted into the body of the patient through an incision or a body orifice and then entered into a body cavity or internal passageway, such as a blood vessel in the cardiovascular system. The distal end of the catheter is advanced within the body cavity or along the internal passageway until the distal end is located at a desired predetermined location for conducting an intended therapeutic activity. Fluid containing medication, nutrients, or cleansing agents can then be introduced through the lumen of the catheter and delivered at the predetermined location through the distal end of the catheter.

The end of such a catheter opposite the distal end is referred to as the proximal end. Once the distal end of a catheter has been implanted at a predetermined location as described above, the proximal end must be attached to the type of medical device that is appropriate to the specific task and manner of use to which the implanted catheter is to be applied. On some occasions the distal end of the catheter with the attached medical device remains outside the body of the patient. In other situations both are implanted subcutaneously in the body of the patient.

For example, if the proximal end of an implanted catheter is to remain outside the body of the patient, the proximal end of the catheter is frequently attached to a catheter termination device that facilitates access to the lumen by a hypodermic needle. Commonly, such catheter termination devices also function to close the proximal end of the catheter when the infusion or withdrawal of fluid is not taking place. In some circumstances the proximal end of an implanted catheter may need to be coupled to tubing that allows the proximal end of the catheter to in turn be fluid coupled to sizable medical devices that must remain outside the body of the patient. In such circumstances the catheter termination device to which the proximal end of the catheter is coupled is ideally selectively and non-destructively couplable with tubing, but the catheter termination device is also provided with the capacity to close the proximal end of the associated catheter whenever such tubing is detached.

On occasion the proximal end of the catheter is attached to one side of a fluid flow accommodating structure that has on the other side structures appropriate for coupling to yet another catheter. This may be done to increase the length of a catheter that is already implanted, or to splice the broken proximal end of an implanted catheter.

In some instances, the proximal end of an implanted catheter will be attached to an access device that is itself also implantable in the body of a patient. Then the entirety of the catheter with the access device attached thereto is embedded at appropriate locations in the tissue of the patient with the distal end of the catheter disposed at the predetermined location at which therapeutic activity is to be effected. Under such circumstances, medication is then delivered to the lumen of the catheter, or withdrawn therefrom, utilizing a hypodermic needle that penetrates the skin of the patient at the implantation site of the access structure and effects a fluid coupling with that access structure.

One problem encountered in attaching the proximal end of a catheter to a given medical device is that catheters are fabricated from a variety of different materials. These materials vary in material properties, such as tensile strength, shear strength, flexibility, and compressibility. Some materials tend to relax over time after being stretched over a rigid structure, a property referred to as creep, while others do not. Some kink more easily than others. Some shear easily in specific directions, while others resist such structural failures.

Silicone and polyurethane are materials used extensively in the medical field in the manufacture of implantable catheters. Silicone and polyurethane each have unique material properties. The use of one material over the other is usually determined by the intended use of the catheter and the conditions in the body to which the catheter will as a result be exposed. Often the selection of a catheter of one material over a catheter of another material is to a large degree merely a function of availability or of the preferences and prior experience of the medical personnel who will use the catheter selected.

The different materials from which catheters can be fabricated results in the availability of catheters having dramatically different material properties.

One area in which different material properties in catheters can have a significant impact is the behavior of the catheter in relation to the catheter attachment structures used to secure the proximal end of a catheter to a medical device. Some types of catheter attachment structures are inappropriate, or even dangerous, when used in connection with catheters made of a particular material. In many cases a specific catheter attachment structure is appropriate, or even safe, only when used with catheters made of a single, specific material.

Catheter attachment structures may cut, tear, or shear catheters of one material, while functioning with absolute safety relative to catheters made of another. One catheter attachment structure may be unable to effect a secure mechanical connection or a fluid tight seal relative to a given catheter material, while performing with adequate safety in relation to another catheter material. One catheter material may be incapable of cooperating effectively with the elements of a given catheter attachment structure, while being ideally suited to doing so with the elements of a different catheter attachment structure.

Thus, if a medical facility intends to permit its personnel to utilize catheters made from a selection of different materials, these facilities must correspondingly purchase and maintain an inventory of corresponding, appropriate catheter attachment structures for each type of catheter material.

Some brands of medical devices are manufactured with components of only a single type of catheter attachment system secured thereto. Thus, the freedom of medical practitioners to select among catheters made of different materials is limited in some cases by the brand of the medical device that is intended to be used in the procedure. Under such circumstances, the freedom to select differing catheter materials is in fact illusory, unless several brands of a given medical device are kept on hand at a medical facility.

The same problem also exists for using different sizes of catheters. That is, at times it is desirable to use a catheter having a larger or smaller size lumen extending therethrough. The size of the lumen affects the flow rate at which a medication can be delivered or a body fluid removed. Medical devices are typically manufactured with catheter attachment systems that can only be used with a catheter having a single defined lumen size. Thus, to enable a medical practitioner to selectively choose a catheter having a defined lumen size and material composition, a medical facility must carry a variety of sizes and brands of medical devices.

This issue is equally as complicated in relation to catheters having more than a single lumen. Dual lumen catheters allow two medications to be delivered simultaneously to a location in the body of a patient. As with single lumen catheters, dual lumen catheters can also be made of different materials and have varying lumen sizes. Thus, medical facilities must also carry selections of varying medical devices that can accommodate different kinds of dual lumen catheters.

In most instances at least one component of each catheter attachment structure is permanently secured to the medical device to which a catheter is to be coupled. Thus, the selection of one catheter attachment system frequently implies the selection of a corresponding medical device. An inventory of differing catheter attachment systems can, therefore, require in reality an inventory of different medical devices.

The purchase of different catheter attachment structures and several brands of a given type of medical device is expensive and requires a commitment of space to store an inventory. Once these costs are assumed, however, the availability of a variety of catheter attachment structures and a plurality of brands of medical devices at a medical facility will afford the medical personnel the freedom to use catheters fabricated from a variety of materials.

The availability of a plurality of types of catheter attachment structures does, however, require close attention to the correct correlation between a catheter and the catheter attachment structure by which it is to be coupled to a medical device. If an inappropriate catheter attachment structure is utilized, the attachment between a catheter and a medical device can leak, or even fail altogether.

Ensuring that a secure mechanical connection and a reliable fluid tight seal is effected between a catheter and a medical device is of utmost importance with regard to assemblies of a catheter and an attached medical device that is to be totally implanted within the body of a patient. In such a situation, an ineffective mechanical coupling or an improper fluid seal can result in major complications and expose a patient to painful, if not fatal, risks.

The failure of the mechanical coupling between an implanted catheter and an implanted medical device can result in one or the other becoming free to migrate throughout the body. Surgical intervention will then be required to locate and remove the loose article. Naturally under such conditions the delivery of medication or the withdrawal of fluid from any predetermined location in the body of the patient is totally frustrated.

Less dramatic, but possibly more insidious, is a catheter attachment with a medical device that is ineffective in producing a reliable fluid seal. Medication will then leak from the implanted assembly at the catheter attachment structure, diverting medication to an improper location. In many cases such misdelivered medication is damaging of tissue about the catheter attachment structure.

Such malfunctions may go undetected for some time, correspondingly resulting in the need for compensatory medical treatments to repair the damage produced. In addition, any failure to deliver medication in at a prescribed rate to a planned predetermined location will undermine the efficacy of a planned course of treatment. Naturally, if leaking is present in the system by which the medication is delivered, the time of the course of treatment will be extended.

Any of the circumstances described above will invariably require the removal of the catheter and the medical devices involved, the replacement of one or both, and then the surgical reimplantation of the entire assembly. Often this must occur at a fresh implantation site, as the original implantation and removal of such devices will have rendered the initial implantation site unusable, at least until a period of healing has passed.

All of these consequences of ineffective catheter attachment unnecessarily add to the duration and to the cost of medical procedures.

Even where an attachment is to be effected to the proximal end of a catheter outside the body of a patient, delay, equipment replacement, and enhanced costs can be anticipated, if a catheter attachment structure is used that is inappropriate to the material of which the associated catheter is made.

SUMMARY OF THE INVENTION

Accordingly, it is an object of the present invention to provide improved methods and systems for attaching catheters to medical devices.

It is another object of the present invention to provide methods and systems for attaching a selected catheter from a set of different kinds of catheters to a single medical device.

Another object of the present invention is to provide methods and systems for attaching a selected catheter from a set of different catheters having varying lumen sizes.

Yet another object of the present invention is to provide methods and apparatus for attaching either a silicone catheter or a polyurethane catheter to a single medical device.

Also, another object of the present invention is to provide methods and apparatus for attaching a selected catheter chosen from a set of three or more catheters each made of different materials.

Another object of the present invention is to provide improved methods and system for attaching catheters to medical devices, as discussed above, wherein the catheters are dual-lumen.

Still another object of the present invention is to provide methods and apparatus that limit the number of attachment structures a hospital or other medical facility needs to purchase and store for attaching catheters to medical devices.

Another object of the present invention is to provide methods and apparatus that limit the number of medical devices used for attachment with a catheter that a medical facility needs to purchase and store.

It is also an object of the present invention to provide methods and apparatus for connecting together opposing ends of catheters made of different materials and having different sizes.

Also, another object of the present invention is to provide methods and apparatus for insuring a secure and liquid tight attachment between a catheter and a medical device.

Finally, it is another object of the present invention to provide methods and apparatus for limiting the number of different catheter attachment structures required in an operation using different kinds of catheters.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a catheter connection system is provided for effecting a fluid-tight coupling and a mechanical joinder between a medical device and a selected catheter. The selected catheter is chosen from three or more catheters each having a unique combination of size and composition. For example, the selected catheter can be made from silicone, polyurethane, or a composite. In some cases, the medical device accommodates a fluid flow. Such medical devices include access ports, leaflet ports, and catheter termination hubs. In the alternative, the medical device can be an instrument that does not accomodate fluid flow such as a medical tunneling instrument.

The selected catheter to be attached to the medical device is typically has a body wall with an exterior surface and with an interior surface that defines a longitudinally extending fluid flow lumen. In some cases, a partition wall extends between spaced locations on the interior surface of the lumen to produce a dual lumen catheter having two distinct fluid flow lumens.

The catheter connection system includes a rigid, tubular stem having a proximal end attached in fluid communication to a medical device. The stem also has a free distal end opposite the proximal end and an exterior surface extending therebetween.

The present invention provides a variety of anchoring means on the exterior surface of the stem for engaging the interior surface of the selected catheter when the distal end of the stem is received within the lumen of the selected catheter and enabling locking of the selected catheter on the stem.

By way of example and not by limitation, such an anchoring means includes a first set of engagement barbs encircling and radially, outwardly extending on the exterior surface of the stem. The first set of engagement barbs are positioned at the distal end of the stem and have a maximum outer diameter so sized as to fit within the lumen of the selected catheter.

A second set of engagement barbs also encircle and radially, outwardly extend on the exterior surface of the stem. The second set of engagement barbs are positioned proximal of the first set of engagement barbs and have a maximum outer diameter larger than the maximum outer diameter of the first set of engagement barbs.

Finally, a locking barb encircles and radially, outwardly extends on the exterior surface of the stem between the second set of engagement barbs and the medical device. The locking barb has a maximum outer diameter that is larger than the maximum outer diameter of the second set of engagement barbs.

By varying the size, number, configuration, and orientation of the engagements barbs and locking barb, a variety of alternative anchoring means can be obtained. A representative example of these alternative embodiments are discussed in the detailed description that follows.

The present invention also provides clinching means operative when the distal end of the stem is received in the lumen of the selected catheter. The clinching means radially, inwardly compresses a portion of the body wall of the selected catheter against a portion of the anchoring means on the stem and interacts with the anchoring means to preclude unintentional disengagement of the selected catheter from the stem.

By way of example and not by limitation, one embodiment of the clinching means operative with such an above-described anchoring means includes a set of three fastening assemblies: a first fastening assembly used with a silicone catheter, a second fastening assembly used with a first polyurethane catheter, and a third fastening assembly used with a second polyurethane catheter that has a smaller inner diameter smaller than first polyurethane catheter. Each will be discussed individually below.

The first fastening assembly includes a first locking sleeve having a proximal end, a distal end, and a passageway longitudinally extending therethrough. To attach the silicone catheter to the stem, the stem is advanced into the lumen of the silicone catheter until the locking barb is received within the silicone catheter. Next, the silicone catheter with the stem received therein is positioned within the passageway of the first locking sleeve. In this position, the interior surface of the first locking sleeve radially, inwardly compresses a portion of the body wall of the silicone catheter against the locking barb on the stem.

An annular compression ring extending inwardly from the interior surface of the first locking sleeve interacts with the locking barb to preclude unintentional disengagement of the silicone catheter from the stem.

The second fastening assembly comprises a second locking sleeve having a distal end, a proximal end, and a passageway extending therebetween. A pliable compression sleeve is longitudinally disposed within the passageway of the second locking sleeve. The compression sleeve has an interior surface defining a passageway longitudinally extending therethrough.

To attach the first polyurethane catheter to the stem, the stem is advanced in the lumen of the first polyurethane catheter until the second set of engagement barbs is received within the lumen. Next, the first polyurethane catheter with the stem received therein is positioned within the passageway of the compression sleeve. In this position, the interior surface of the compression sleeve radially, inwardly compresses a portion of the body wall of the first polyurethane catheter against the second set of engagement barbs on the stem. Positioned at the proximal end of the second locking sleeve is an opposing set of radially displaceable resilient C-shaped clamps. The C-shaped clamps grasp the locking barb to prevent unintentional disengagement of the polyurethane catheter from the stem.

The third fastening assembly comprises a third locking sleeve having a distal end, a proximal end, and a passageway extending therebetween. A pliable compression sleeve is longitudinally disposed within the passageway of the second locking sleeve. The compression sleeve has an interior surface defining a passageway longitudinally extending therethrough. The interior surface comprises an annular first portion having an inner diameter positioned at the distal end of the compression sleeve and proximal thereof an annular second portion having an inner diameter larger than the inner diameter of the first portion.

To attach the second polyurethane catheter to the stem, the stem is received within the lumen of the second polyurethane catheter so that only the first set of engagement barbs are received within the lumen. Next, the second polyurethane catheter with the first set of engagement barbs received therein is positioned within the passageway of the compression sleeve. In this position, the annular first portion of the compression sleeve radially, inwardly compresses a portion of the body wall of the second polyurethane catheter against the first set of engagement barbs on the stem. Positioned at the proximal end of the third locking sleeve is an opposing set of radially displaceable resilient C-shaped clamps. The C-shaped clamps grasp the locking barb to prevent unintentional disengagement of the polyurethane catheter from the stem.

The above three fastening assemblies are only representative examples of a clinching means. Alternative embodiments can also be obtained by varying the size, shape, and configuration of the elements of the above disclosed clinching means. Such alternative clinching means are discussed in the detailed description that follows.

Using similar structural elements as discussed above with regard to the anchoring means and clinching means, the present invention also includes catheter connection systems used with dual lumen catheters. For example, catheter connection systems are provided for effecting a fluid-tight coupling in a mechanical joinder between a medical device that accommodates two separate fluid flows and a selected dual lumen catheter. The selected dual lumen catheter can be chosen from two or more dual lumen catheters having a unique combination of size and composition.

DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 7 is an exploded perspective view in partial breakaway of the elements of a fastening assembly for attaching the polyurethane catheter to the stem;

FIG. 8 is a cross-sectional view of part of the fastening assembly shown in FIG. 7;

FIG. 9 is a cross-sectional view of the stem in FIG. 3 being received within the lumen of the polyurethane catheter while the polyurethane catheter is disposed through a passageway in the fastening assembly shown in FIG. 7;

FIG. 10 is a cross-sectional view of the polyurethane catheter and the elements of the connection system of FIG. 7 shown in an assembled state thereof;

FIG. 21 is an elevation view in partial cross section of the disassembled elements of the catheter connection system of FIG. 20 used to secure the small polyurethane catheter to the stem;

FIG. 22 is an elevation view in partial cross section of the elements of the connection system of FIG. 21 in an assembled condition;

FIG. 23 is an elevation view of a second embodiment of a stem useable in a multiple-type catheter connection system shown in FIG. 20;

FIG. 24 is an elevation view in partial section of the stem of FIG. 23, a small silicone catheter, and the corresponding fastening assembly of the catheter connection system of FIG. 20, all in an assembled condition;

FIG. 25 is an elevation view in partial cross section of the stem of FIG. 23, a small polyurethane catheter, and the corresponding fastening assembly of the catheter connection system of FIG. 20, all in an assembled condition;

FIG. 26 is an elevation view in partial cross section of a third embodiment of an outlet stem useable in the multiple-type catheter connection system of FIG. 20, a small polyurethane catheter, and the corresponding fastening assembly of that system, all in an assembled condition;

FIG. 27 is an elevation view in partial cross section of the catheter connection system shown in FIG. 26, a large polyurethane catheter, and the corresponding fastening assembly of that system, all in an assembled condition;

FIG. 28 is an elevation view in partial cross of disassembled elements of a third embodiment of the catheter connection system of FIG. 20, used to secure a composite catheter to the stem;

DESCRIPTION OF THE PREFERRED EMBODIMENTS

Figure 1:
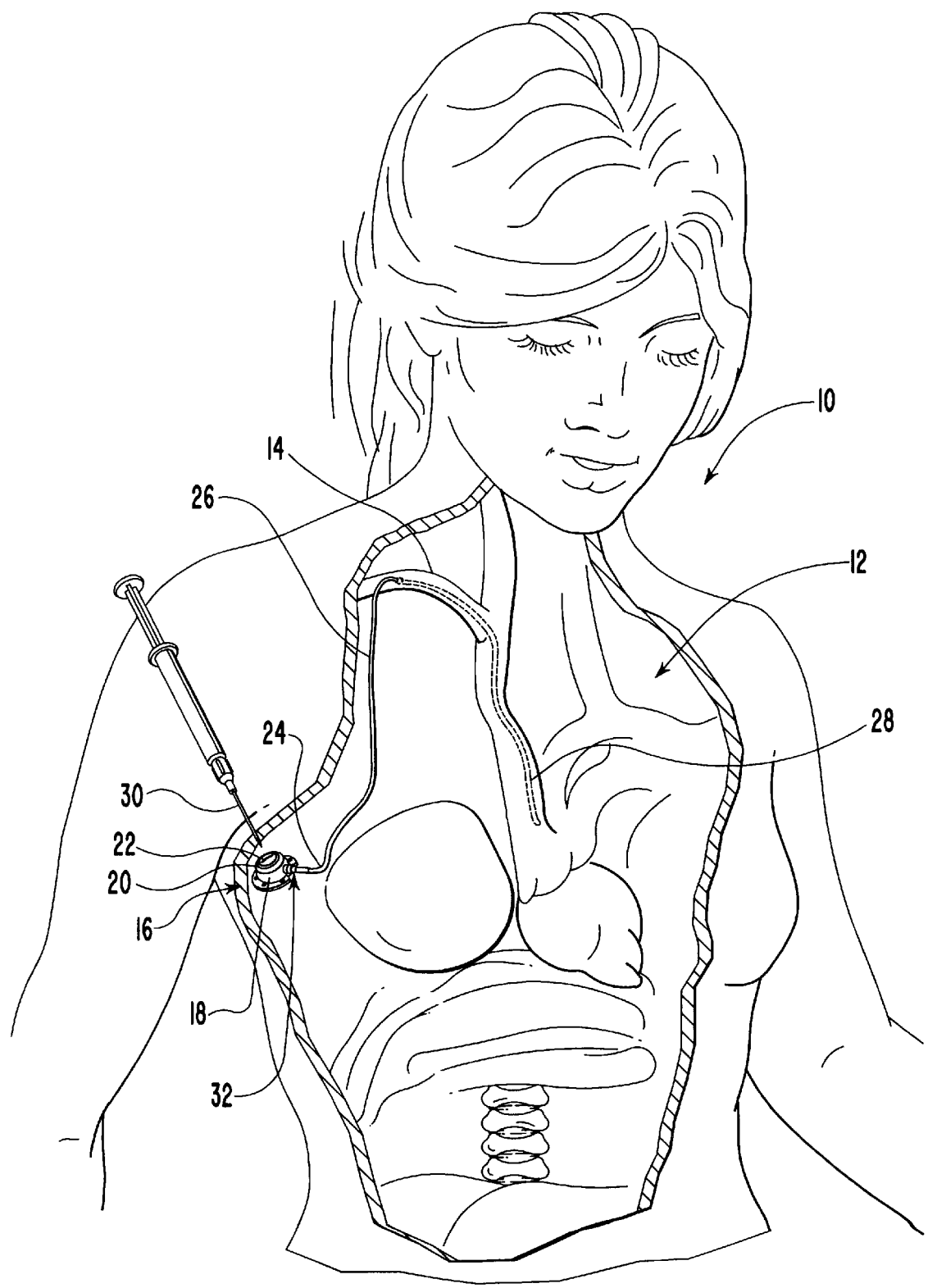
FIG. 1 is a perspective view of an access port implanted within a body of a patient and connected to a catheter by a catheter connection system embodying the teachings of the present invention.

Referring to FIG. 1, a patient 10 is shown having a chest 12 and a subclavian vein 14 therein. Implanted in chest 12 is an access port 16, which is one example of a medical device that can be used with the present invention. Access port 16 is shown as comprising a needle impenetrable housing 18 which encloses a fluid cavity, not shown in the figure, that is provided with an access opening 20. A needle penetrable septum 22 is retained in access opening 20 to seal the fluid cavity.

Also implanted in chest 12 is an elongated, pliable catheter 26 having a proximal end 24 that is attached in fluid communication to access port 16 by a catheter connection system 32. Catheter 26 is disposed in part within subclavian vein 14. A hypodermic needle 30 can penetrate septum 22 to deliver medication to the fluid cavity of access port 16. The medication then travels through catheter 26 and is discharged into the cardiovascular system of patient 10 at distal end 28 of catheter 26.

Figure 2:
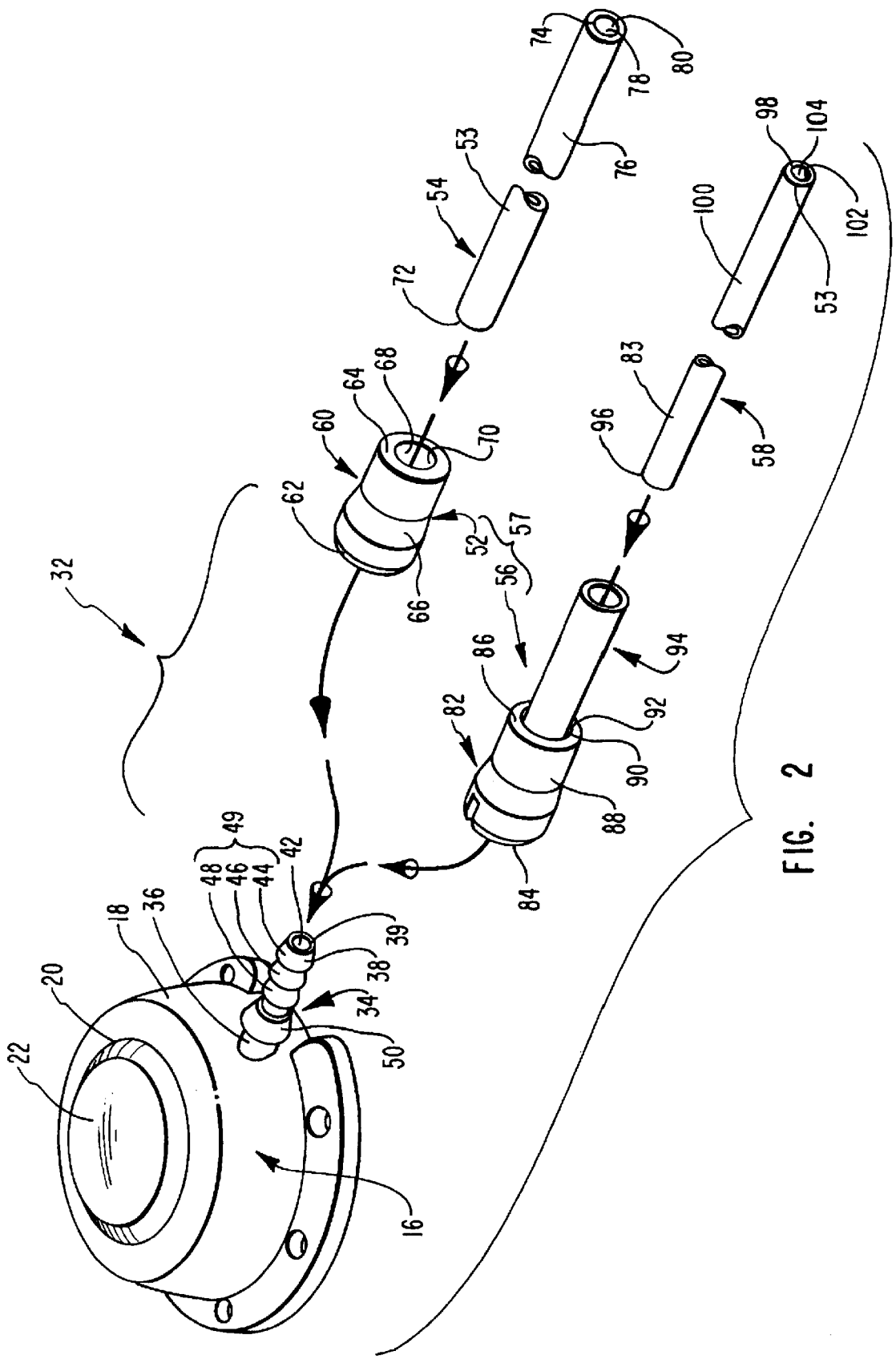
FIG. 2 is a perspective view of the access port of FIG. 1 with the catheter connection system thereof in disassembled condition, the catheter connection system including generally a stem extending from the access port and a set of fastening assemblies individually corresponding to either a silicone catheter or a polyurethane catheter.

FIG. 2 is an enlarged view of access port 16 with alternative elements of catheter connecting system 32 shown in a disassembled condition. FIG. 2 reveals catheter connection system 32 as comprising a rigid tubular stem 34 attached at proximal end 36 to access port 16 and having a free distal end 38 that tapers to a distal terminus 39. Extending between proximal end 36 and distal end 38 is an exterior surface 40 shown in FIG. 3 and discussed in detail subsequently relative thereto.

Stem 34 is depicted as being substantially cylindrical and having a passageway 42 longitudinally extending therethrough that is in fluid communication with access port 16. Stem 34 can have different cross-sectional configurations, such as elliptical, polygonal, or irregular configurations.

A first engagement barb 44 extends radially outwardly on exterior surface 40 at distal end 38 of stem 34 and encircles stem 34. A second engagement barb 46 and a third engagement barb 48 are consecutively aligned with first engagement barb 44 and likewise extends radially outwardly on exterior surface 40 of stem 34 and encircle stem 34. First engagement barb 44, second engagement barb 46, and third engagement barb 48 each have substantially the same configuration and are cumulatively referred to as engagement barbs 49.

A locking barb 50 extends radially outwardly on exterior surface 40 of stem 34 and encircles stem 34 between third engagement barb 48 and proximal end 36 of stem 34. In one embodiment, stem 34 is made separately from access port 16 and is press fit thereinto. Stem 34 can thus be made from a different material than access port 16. Stem 34, engagement barbs 49, and locking barb 50 are substantially rigid elements which are preferably made from titanium. In the alternative, stem 34, engagement barbs 49, and locking barb 50 can be made from other metals, such as stainless steel, or even from plastics, such as polycarbonate or acetal copolymer.

FIG. 2 further reveals catheter connection system 32 as comprising a first fastening assembly 52 that includes a rigid first locking sleeve 60. First locking sleeve 60 is shown as having a proximal end 62, a distal end 64, and an exterior surface 66 extending therebetween. Furthermore, first locking sleeve 60 has an interior surface 68 defining a passageway 70 longitudinally extending therethrough. First locking sleeve 60 is preferably molded formed from polycarbonate. In the alternative, first locking sleeve 60 can be made from other plastics, such as an acetal copolymer, or from a metal like titanium or stainless steel.

Operative with first fastening assembly 52 is an elongated, pliable silicone catheter 54 having a body wall 53 with an exterior surface 76 extending between a proximal end 72 and a distal end 74. Body wall 53 of silicone catheter 54 also has an interior surface 78 that defines a lumen 80 longitudinally extending through catheter 54.

In the alternative to using first fastening assembly 52, catheter connection system 32 also includes a second fastening assembly 56. First fastening assembly 52 and second fastening assembly 56 comprise a set of fastening assemblies 57. Second fastening assembly 56 is shown in FIG. 2 as comprising a rigid second locking sleeve 82 having a proximal end 84, a distal end 86, and an exterior surface 88 extending therebetween. Longitudinally extending through second locking sleeve 82 is a passageway 90 defined by an interior surface 92. Disposed within passageway 90 is an elongated compression sleeve 94, which will be discussed later in detail.

As second locking sleeve 82 includes more intricately shaped internal components than does first locking sleeve 60 second locking sleeve 82 is preferably machined from a plastic, such as an acetal copolymer, rather than being molded. In the alternative, second locking sleeve 82 can be fashioned from other plastics, such as polycarbonate, or from metals like titanium or stainless steel.

Operative with second fastening assembly 56 is an elongated polyurethane catheter 58 that is less pliant than silicone catheter 54. Polyurethane catheter 58 has a body wall 83 with an exterior surface 100 extending between a proximal end 96 and a distal end 98. Body wall 83 of polyurethane catheter 58 has an interior surface 102 defining a lumen 104 longitudinally extending therethrough.

Figure 3:
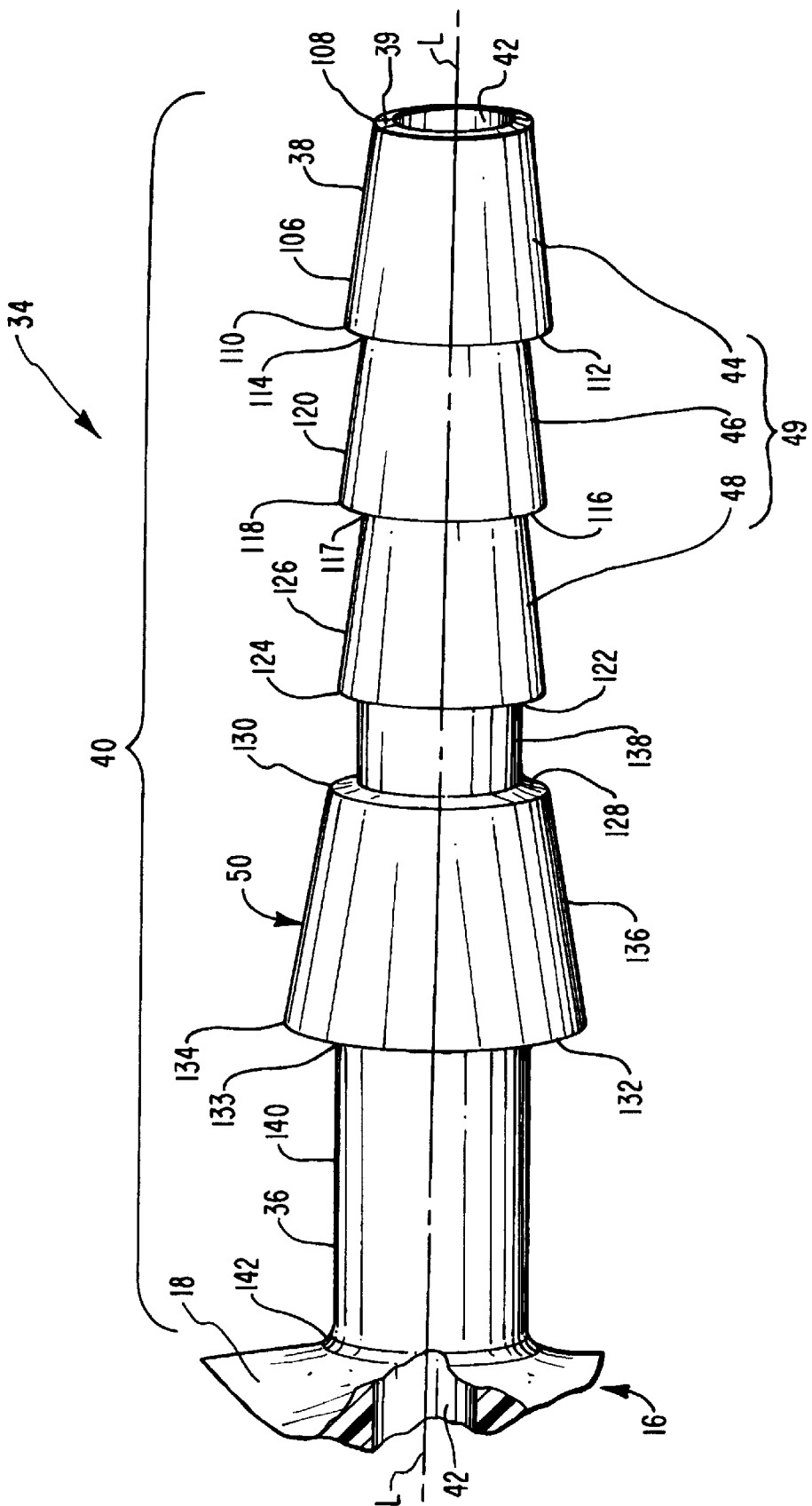
FIG. 3 is an enlarged side view of the stem in FIG. 2.

FIG. 3 is an enlarged side view of stem 34. First engagement barb 44 is depicted therein as terminating at one end thereof in a distal tip 108 that encircles stem 34 at distal terminus 39 thereof. An annular first barb face 112 encircles stem 34 and extends radially outward therefrom along a plane perpendicular to the longitudinal axis L of stem 34 to an outer ridge 110 at the opposite end of the first engagement barb 44. A frustoconical first engagement surface 106 encircles stem 34 and extends increasingly radially outwardly therefrom in a direction from distal tip 108 to outer ridge 110.

In a similar fashion, second engagement barb 46 comprises a distal tip 114 that encircles stem 34 adjacent to first barb face 112. An annular second barb face 116 encircles stem 34 and extends radially outward therefrom along a plane perpendicular to the longitudinal axis L of stem 34 to an outer ridge 118 of second engagement barb 46. A frustoconical second engagement surface 120 encircles stem 34 and extends to increasingly radially outwardly therefrom in a direction from distal tip 114 to outer ridge 118.

In like manner, third engagement barb 48 comprises a distal tip 117 that encircles stem 34 adjacent to second barb face 116. An annular third barb face 122 encircles stem 34 and extends radially outward therefrom along a plane perpendicular to the longitudinal axis L of stem 34 to an outer ridge 124 of third engagement barb 48. A frustoconical third engagement surface 126 encircles stem 34 and extends increasingly radially outwardly therefrom in a direction from distal tip 117 to outer ridge 124.

Locking barb 50 is depicted in FIG. 3 as comprising an annular distal side wall 128 that encircles stem 34 and extends radially outwardly therefrom along a plane perpendicular to the longitudinal axis L of stem 34 to an outside corner 130. Locking barb 50 also comprises an annular proximal side wall 132 that encircles stem 34 and extends radially outwardly therefrom in a direction from an inside corner 133 on stem 34 to an outside corner 134 of locking barb 50 that is distal of inside corner 133. Outside corner 134 has an outer diameter that is larger than the outer diameter of outside corner 130.

Figure 4:
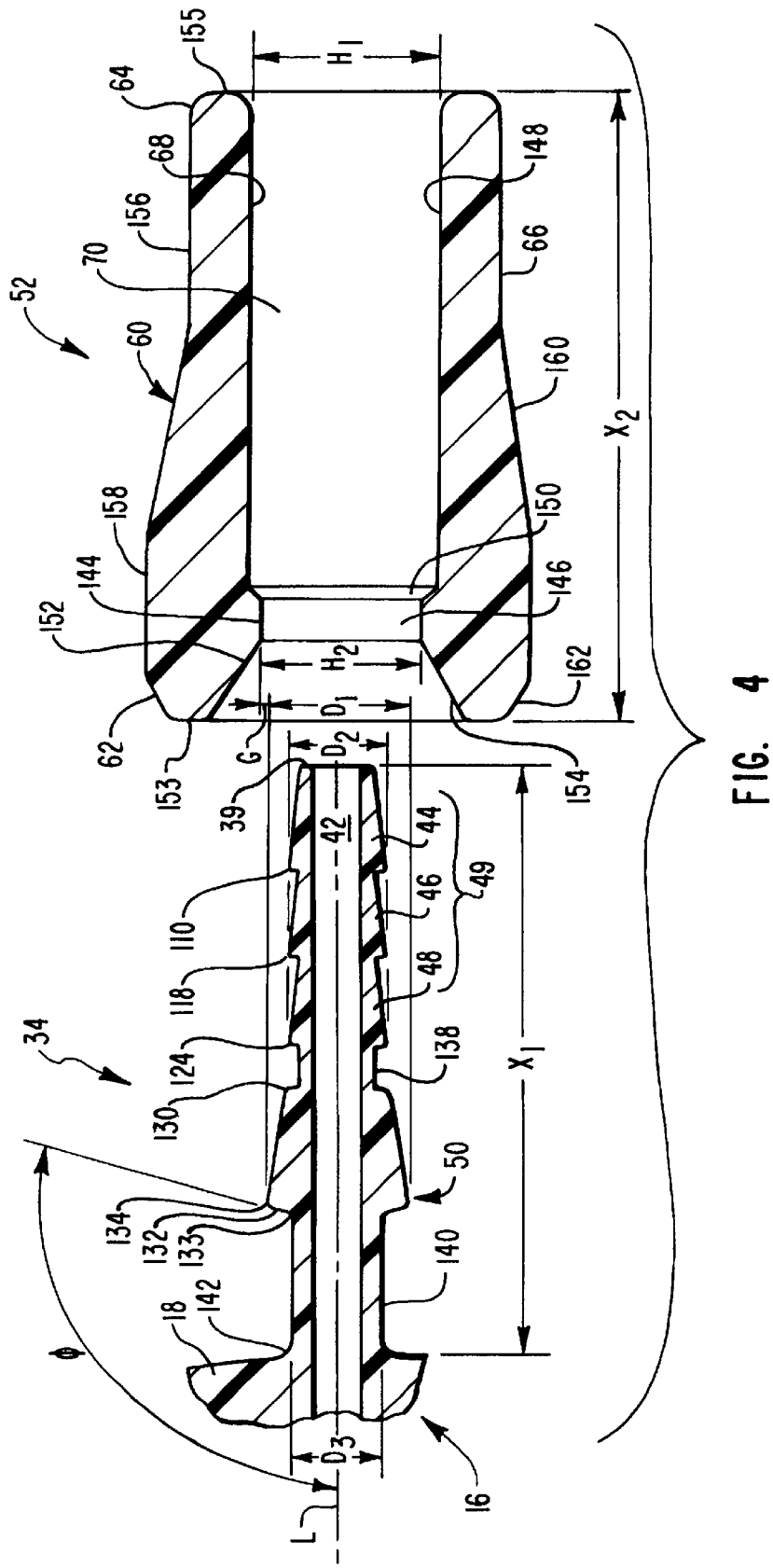
FIG. 4 is a cross-sectional view of the stem shown in FIG. 3 and the particular fastening assembly used for attaching the silicone catheter to the stem.

Proximal side wall 132 extends between inside corner 133 and outside corner 134 at an angle φ shown in FIG. 4 to be greater than 90°. Angle φ is measured between proximal side wall 132 and the longitudinal axis L of stem 34 proximal of proximal side wall 132. Preferably angle φ is in a range from about 95° to about 125°. Locking barb 50 also includes a frustoconical surface 136 that encircles stem 34 and extends increasingly radially outwardly therefrom in a direction from outside corner 130 of distal side wall 128 to outside corner 134 of proximal side wall 132. Surface 136 and proximal side wall 132 are shown in FIG. 4 at a right angle to each other.

Extending between distal side wall 128 of locking barb 50 and third barb face 122 of third engagement barb 48 is a first cylindrical portion 138 of stem 34. Extending between proximal side wall 132 of locking barb 50 and access port 16 is a second cylindrical portion 140 of stem 34. Stem 34 is attached to access port 16 at an extreme proximal end 142 of stem 34.

A cross-sectional view of stem 34 in FIG. 4 discloses outside corner 134 of locking barb 50 as having an outer diameter $D_1$. Outer ridges 110, 118, and 124 of engagement barbs 49, as shown in FIG. 3, each have the same outer diameter $D_2$, which is smaller than outer diameter $D_1$ of locking barb 50. Stem 34 has a length $X_1$ from extreme proximal end 142 to distal terminus 39, and second cylindrical portion 140 has an outer diameter $D_3$.

Also depicted in FIG. 4 is a cross-sectional view of first fastening assembly 52 showing first locking sleeve 60 as including an annular proximal end face 153, an opposing annular distal end face 155, and a length $X_2$ therebetween. Interior surface 68 of first locking sleeve 60 is shown as including a radially inwardly extending annular compression ring 144, and having a substantially cylindrical portion 148 extending between compression ring 144 and distal end face 155. Cylindrical portion 148 is shown as having an inner diameter $H_1$.

Compression ring 144 comprises a cylindrical compression surface 146 and a distal shoulder 150 sloping radially outward to cylindrical portion 148. Compression surface 146 of compression ring 144 has an inner diameter $H_2$ that is smaller than inner diameter $H_1$ of cylindrical portion 148. Inner diameter $H_2$ of compression surface 146 is slightly larger outer diameter $D_1$ of locking barb 50, so that an annular gap cap G results between inner compression surface 146 and outside corner 134 of locking barb 50.

Compression ring 144 is also partially defined by a proximal shoulder 152 that slopes radially outward from compression surface 146 to proximal end face 153 of first locking sleeve 60, thereby forming an enlarged receiving mouth 154.

Exterior surface 66 of first locking sleeve 60 includes a first cylindrical surface 156 positioned at distal end 64 of first locking sleeve 60 and a second cylindrical surface 158 positioned at proximal end 62 of first locking sleeve 60. Second cylindrical surface 158 has a larger outer diameter than first cylindrical surface 156. A sloped transition shoulder 160 extends between first cylindrical surface 156 and second cylindrical surface 158.

Transition shoulder 160 better enables a user to grasp and position first fastening assembly 52 in the manner to be discussed later. In alternative embodiments, exterior surface 66 of first locking sleeve 60 can be ribbed, cylindrical, textured, or of any other configuration that could be of assistance in the manipulation of first fastening assembly 52. To eliminate sharp edges, a corner shoulder 162 extends between second cylindrical surface 158 and proximal end face 153 on first locking sleeve 60.

Figure 5:
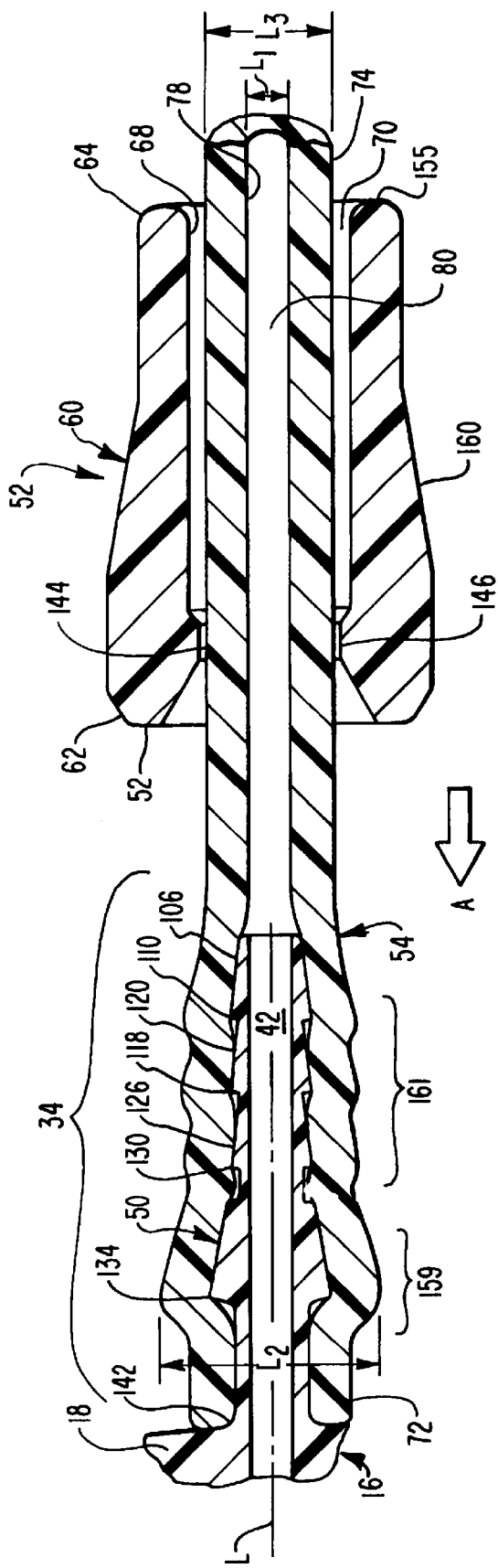
FIG. 5 is a cross-sectional view of the stem in FIG. 4 being received within the lumen of the silicone catheter while the silicone catheter is disposed through a passageway in the fastening assembly.

As depicted in FIG. 5, to attach silicone catheter 54 to access port 16, stem 34 is initially received within lumen 80 of silicone catheter 54 by sliding silicone catheter 54 over engagement barbs 49 and locking barb 50 until proximal end 72 of silicone catheter 54 abuts against housing 18 of access port 16. Lumen 80 of silicone catheter 54 is shown as having an inner diameter $L_1$ that is smaller than outer diameter $D_1$ shown in FIG. 4 of outside corner 134 of locking barb 50. Accordingly, once stem 34 is received within lumen 80, a first expansion portion 159 of silicone catheter 54 over locking barb 50 is urged radially outward. First expansion portion 159 has an outer diameter $L_2$. The normal or unexpanded remaining portion of silicone catheter 54 has an outer diameter $L_3$.

In the embodiment shown in FIG. 5, outer diameter $D_2$ of engagement barbs 49 is larger than inner diameter $L_1$ of lumen 80 of silicone catheter 54. As a result, a second expansion portion 161 of silicone catheter 54 over engagement barbs 49 is urged radially outwardly Outer diameter $D_2$ of engagement barbs 49 may alternatively be smaller than inner diameter $L_1$ of lumen 80 of silicone catheter 54.

Figure 6:
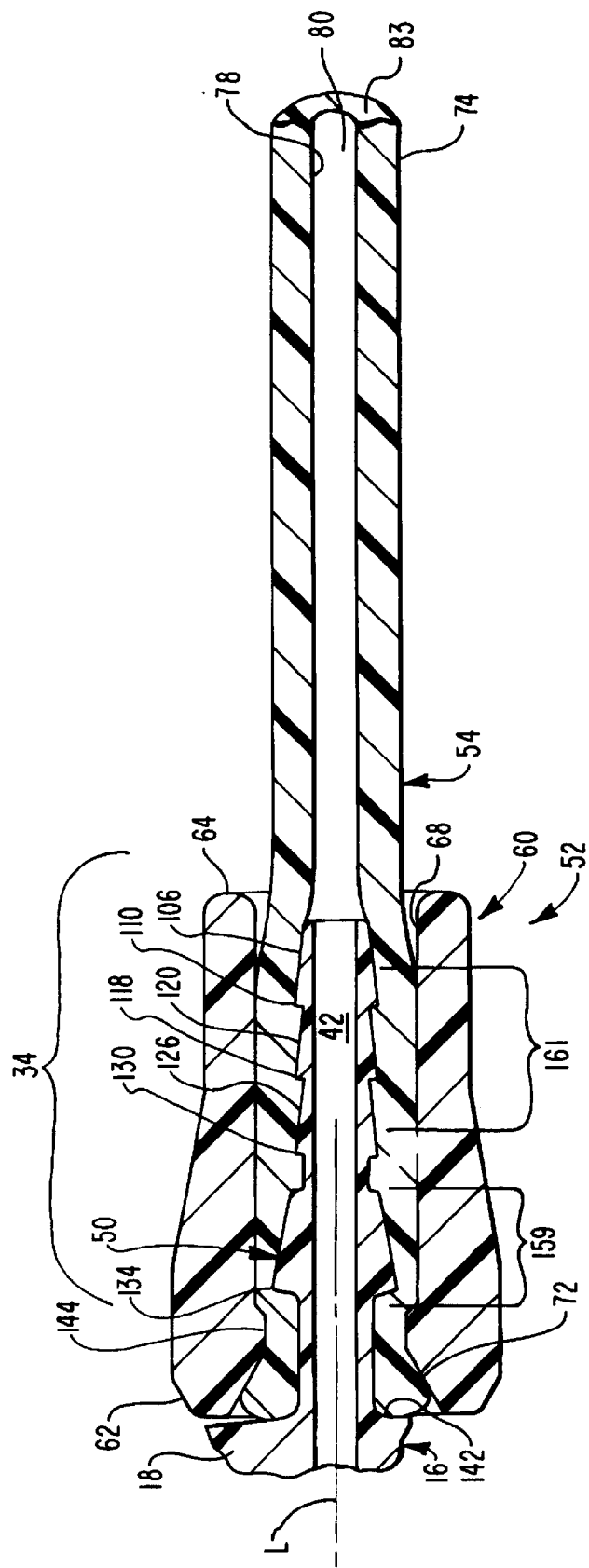
FIG. 6 is a cross-sectional view of the silicone catheter and the elements of the connection system of FIG. 5 shown in an assembled state thereof.

Also depicted in FIG. 5 is a cross-sectional view of first fastening assembly 52 with silicone catheter 54 passing through passageway 70 thereof. By advancing first fastening assembly 52 in the direction of arrow A shown in FIG. 5, stem 34 within lumen 80 of silicone catheter 54 is eventually received within passageway 70 of first locking sleeve 60 as shown in FIG. 6. First fastening assembly 52 is advanced in the direction of arrow A until compression ring 144 passes over locking barb 50 and is positioned between locking barb 50 and access port 16.

Although inner diameter $H_2$ of compression ring 144 and inner diameter $H_1$ of cylindrical portion 148 are each larger than outer diameter $D_1$ of locking barb 50, inner diameter $H_2$ and inner diameter $H_1$ are each smaller than outer diameter $L_2$ of first expansion portion 159 of silicone catheter 54 over locking barb 50. Accordingly, as compression ring 144 passes over locking barb 50, first expansion portion 159 of silicone catheter 54 is compressed therebetween. Annular gap G shown in FIG. 4 between outer diameter $D_1$ of locking barb 50 and inner diameter $H_2$ of compression ring 144 is sufficiently large, however, so that first expansion portion 159 is not ruptured or sheared in the process. Once compression ring 144 passes to the proximal side of locking barb 50, first expansion portion 159 again expands but still remains compressed between cylindrical portion 148 of first locking sleeve 60 and locking barb 50.

Accordingly, with first fastening assembly 52 positioned as shown in FIG. 6, compression ring 144 and interior surface 68 of first locking sleeve 60 radially, inwardly compresses body wall 83 of silicone catheter 54 against locking barb 50 and stem 34 to create a fluid-tight coupling between stem 34 and silicone catheter 54. The interaction between compression ring 144, silicone catheter 54, and locking barb 50 also creates a mechanical joinder therebetween which precludes unintentional disengagement of silicone catheter 54 from stem 34.

In the embodiment shown in FIG. 6, interior surface 68 of first locking sleeve 60 also compresses second expansion portion 161 of body wall 83 against engagement barbs 49. Although unnecessary, this interaction between engagement barbs 49 and body wall 83 assists in the formation of the liquid-tight seal and the mechanical joinder between stem 34 and silicone catheter 54.

Referring now to FIG. 7, second fastening assembly 56 is seen to comprise a second locking sleeve 82 and a compression sleeve 94. Compression sleeve 94 comprises a body wall 170 having a proximal end 164, a distal end 166, and an exterior surface 168 extending therebetween. A passageway 171 longitudinally extends through compression sleeve 94 and is defined by an interior surface 173. Passageway 171 has an inner diameter M.

Compression sleeve 94 further comprises a substantially cylindrical head portion 172 having an annular proximal end face 174 and an annular distal end face 176. Axially aligned with and extending from distal end face 176 is a tail portion 178 which terminates at a distal end face 180. Tail portion 178 has an outer diameter that is smaller than the outer diameter of head portion 172. Compression sleeve 94 is preferably made from silicone, although other pliant compressible materials can be used.

Also depicted in FIG. 7 is second locking sleeve 82 which includes a pair of opposing, resilient C-shaped clamps 182 and 184 positioned at proximal end 84 thereof. C-shaped clamps 182 and 184 are separated by a first slot 186 and a second slot 188 which extend through proximal end 84 of second locking sleeve 82 along an axis perpendicular to the longitudinal axis of second locking sleeve 82. First slot 186 and a second slot 188 enable C-shaped clamps 182 and 184 to pivot away from each other, expanding first slot 186 and second slot 188 therebetween, when an outwardly directed radial force is imposed on either of C-shaped clamps 182, 184. In alternative embodiments, a single slot or more than a pair of slots can extend through proximal end 84 of second locking sleeve 82 to form a corresponding number of resilient clamps.

Second locking sleeve 82 is depicted in a cross-sectional view in FIG. 8. As shown therein, second locking sleeve 82 has a proximal end face 212, an annular distal end face 216, and a length $X_3$ therebetween. Distal end face 216 in part defines an annular bracing ring 190 that extends radially inwardly from interior surface 92 at distal end 86 of second locking sleeve 82. Bracing ring 190 is defined by an annular proximal side wall 218 and an interior surface 220 that extends between proximal side wall 218 and distal end face 216 of second locking sleeve 82.

Extending between C-shaped clamp 182 and bracing ring 190 on interior surface 92 is a cylindrical compression portion 192. C-shaped clamps 182 and 184 together comprise an arm 194 extending longitudinally from compression portion 192. An attachment ridge 196 projects radially inwardly extends from said arm 194 and terminates at an interior surface 202 with an inner diameter N. Attachment ridge 196 includes a sloping proximal shoulder 198 that extends outward from interior surface 202 to proximal end face 212 of second locking sleeve 82. An annular distal end face 200 extends from interior surface 202 to arm 194.

Exterior surface 88 of second locking sleeve 82 has a first cylindrical surface 204 positioned at distal end 86 and a second cylindrical surface 206 positioned at proximal end 84. Second cylindrical surface 206 has a larger outer diameter than does first cylindrical surface 156. A sloped transition shoulder 208 extends between first cylindrical surface 204 and second cylindrical surface 206. Transition shoulder 208 serves the same purpose as discussed with regard to transition shoulder 160 of first locking sleeve 60. Likewise exterior surface 88 can have the same alternative embodiments as exterior surface 66 of first locking sleeve 60. To eliminate sharp edges, a corner shoulder 210 extends between second cylindrical surface 206 and proximal end face 212 on second locking sleeve 82.

Depicted in FIG. 9, head portion 172 of compression sleeve 94 is disposed within second locking sleeve 82. Exterior surface 168 of head portion 172 is biased against compression portion 192 of second locking sleeve 82; proximal end face 174 of head portion 172 is biased against distal end face 200 of attachment ridge 196; and distal end face 176 of head portion 172 is biased against proximal side wall 218 of bracing ring 190. Compression sleeve 94 can be freely disposed in locking sleeve 82, or can be secured to second locking sleeve 82 by an adhesive.

To attach polyurethane catheter 58 to access port 16, stem 34 is initially received within lumen 104 of polyurethane catheter 58 by sliding polyurethane catheter 58 over engagement barbs 49 until proximal end 96 of polyurethane catheter 58 abuts distal side wall 128 of locking barb 50. Lumen 104 of polyurethane catheter 58 has an inner diameter $Y_1$ that is slightly smaller than maximum outer diameter $D_2$ of engagement barbs 49. Accordingly, as stem 34 is received within lumen 104 an expansion portion 220 of polyurethane catheter 58 over engagement barbs 49 is urged radially outwardly. Expansion portion 220 has a maximum outer diameter $Y_2$. The normal or unexpanded remaining portion of polyurethane catheter 58 has an outside diameter $Y_3$.

Polyurethane catheter 58 is also shown in FIG. 9 extending through passageway 171 of compression sleeve 94. By urging second fastening assembly 56 in the direction of arrow B shown in FIG. 9, stem 34 within lumen 104 of polyurethane catheter 58 is received within passageway 171 of compression sleeve 94 as shown in FIG. 10.

Inner diameter N of attachment ridge 196 is smaller than maximum outer diameter $D_1$ of locking barb 50. Accordingly, as second fastening assembly 56 is advanced in the direction of arrow B, attachment ridge 196 passes over engagement barbs 49 and is urged against radially expanding, frustoconical top surface 136 of locking barb 50.

The force applied to second fastening assembly 56 in the direction of Arrow B causes C-shaped clamps 182 and 184 to radially expand and pass over outer corner 134 of locking barb 50. The resilience of C-shaped clamps 182 and 184 then causes C-shaped clamps 182 and 184 to spring closed, such that attachment ridge 196 becomes biased against proximal side wall 132 of locking barb 50. The interaction between C-shaped clamps 182 and 184 and locking barb 50 creates a mechanical joinder that precludes unintentional disengagement of stem 34 from polyurethane catheter 58.

The springing or constricting force of C-shaped clamps 182 and 184 works in conjunction with the slope of proximal side wall 132 to cause second fastening assembly 56 to be continually urged in the direction of arrow B. The slope of proximal side wall 132 does, however, permit the removal of second fastening assembly 56 by applying a force to second fastening assembly 56 in the direction opposite of arrow B.

Maximum outer diameter $Y_2$ of expansion portion 220 is larger than inner diameter M of passageway 171 of compression sleeve 94. Accordingly, with C-shaped clamps 182 and 184 positioned as discussed above, interior surface 92 of second fastening assembly 56 and head portion 1sleeve 94 radially,sleeve 94 radially, inwardly compresses expansion portion 220 of polyurethane catheter 58 against engagement barbs 49 and stem 34 to create a fluid-tight coupling between stem 34 and polyurethane catheter 58.

Figure 11:
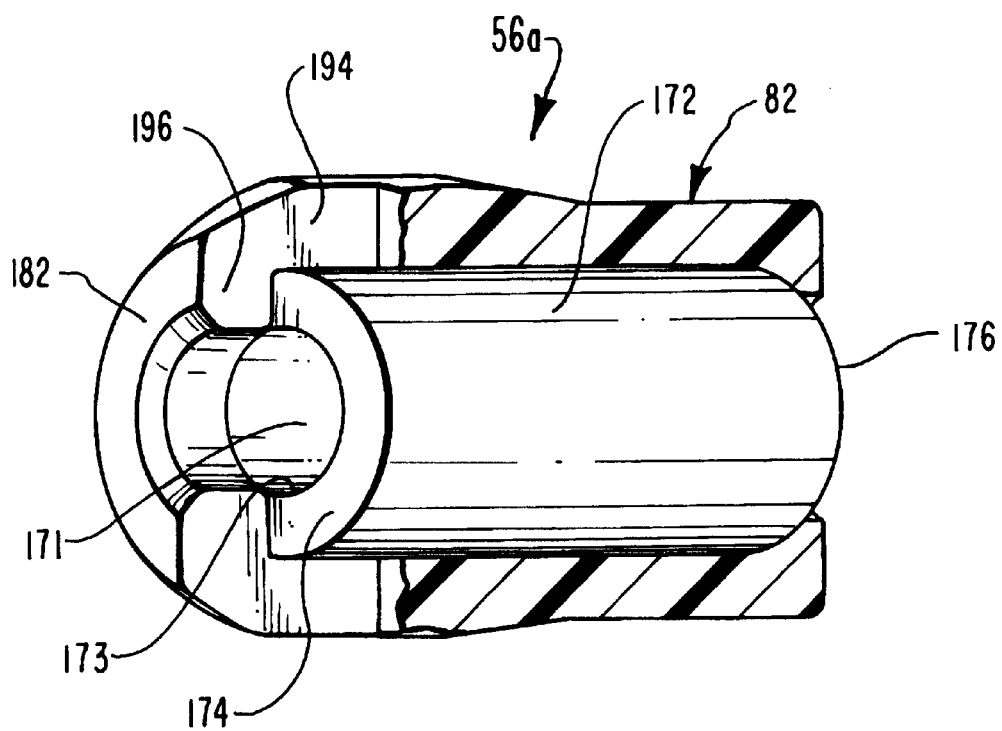
FIG. 11 is a perspective view in partial breakaway of a second embodiment of a fastening assembly for attaching the polyurethane catheter to the stem.

As shown in FIG. 10, a portion 214 of compression sleeve 94 encircles and supports polyurethane catheter 58 distal of distal end 86 of second locking sleeve 82 to prevent sharp bending in polyurethane catheter 58 which could result in kinking or pinching of polyurethane catheter 58 at that location. In an alternative embodiment of a second fastening assembly 56a shown in FIG. 11, tail portion 178 of compression sleeve 94 is eliminated, and only head portion 172 is used with second locking sleeve 82.

The embodiment of catheter connection system 32 is disclosed above is used with silicone catheter 54 and polyurethane catheter 58. In the alternative, catheter connection system 32 can be used with any first and second catheter where, the first and second catheter are made from different materials, and one material is less pliant than the other material. The catheter made of the less pliant material is then secured to stem 34 by second fastening assembly 56, and the catheter made of the other material is secured to stem 34 by first fastening assembly 52.

The size and dimensions of engagement barbs 49, locking barb 50, first fastening assembly 52, and second fastening assembly 56 depend on the size of the inner and outer diameter of the corresponding catheters used and on the materials from which the corresponding catheters are made. For example, the outer diameters of locking barb 50 and engagement barbs 49 generally increase as the inner diameter of the catheter corresponding to each of these attachment structures increases.

As compliance decreases in the material from which a catheter is made, the difference generally decreases between the inside diameter of the catheter and the maximum outer diameter of the corresponding attachment structures, such as locking barb 50 or engagement barbs 49.

Since the size of locking barb 50 and engagement barbs 49 vary depending on the specific catheter to be attached thereto, the size of locking barb 50 and engagement barbs 49 can vary independent of each other. For example, to selectively attach either a silicone catheter having a relatively small inner diameter or a polyurethane catheter having a relatively large inner diameter to stem 34, it may be necessary to decrease the outer diameter of locking barb 50 and increase the outer diameter of engagement barbs 49.

Outlined below are selected dimensions for one embodiment of a catheter connection system, such as catheter connection system 32 disclosed above, for use alternatively with a selected one of a polyurethane catheter, such as polyurethane catheter 58, and a silicone catheter, such as silicone catheter 54. Thus, selected dimensions for these specific catheters are also provided. In each case the dimensions are identified by corresponding reference characters shown in selected of the figures already discussed above. All dimensions are given in inches.

Silicone catheter 54 has the following dimension as shown in FIG. 5:

$L_1$=0.02–0.04

$L_3$=0.08–0.01

Polyurethane catheter 58 has the following dimensions as shown in FIG. 9:

$Y_1 = 0.03 – 0.05$ $Y_3 = 0.05 – 0.07$

Stem 34, locking barb 50, and engagement barbs 49 are made of titanium and have the following dimensions as shown in FIG. 4:

$X_1 = 0.34 – 0.36$ $D_1 = 0.08 – 0.10$ $D_2 = 0.04 – 0.06$ $D_3 = 0.04 – 0.06$

First fastening assembly 52 is made of polycarbonate and has the following dimensions as shown in FIG. 4:

$X_2 = 0.35 – 0.37$ $H_1 = 0.17 – 0.19$ $H_2 = 0.09 – 0.11$

Finally, second fastening assembly 56 includes second locking sleeve 82 made of acetal copolymer and compression sleeve 94 made of silicone. Second fastening assembly 56 has the following dimensions as shown in FIGS. 7 and 8:

$X_3 = 0.31 – 0.33$ $N = 0.08 – 0.09$ $M = 0.06 – 0.08$

In accordance with one aspect of the present invention, a catheter connection system, such as catheter connection system 34, is provided with attachment means on exterior surface 40 of stem 34 for engaging the interior surface of a selected catheter chosen from either a first catheter of a first material or a second catheter of a second material, where the second material is less pliant than the first material. The interior surface of the selected catheter is engaged when distal end 38 of stem 34 is received in the lumen of the selected catheter. The attachment means also enables locking of the selected catheter on stem 34.

By way of example and not by limitation, one form of the structures capable of performing the function of such an attaching means and disclosed herein includes engagement barbs 49 and locking barb 50 that are on exterior surface 40 of stem 34. As shown and discussed with regard to FIGS. 5 and 6 above, locking barb 50 engages interior surface 78 of silicone catheter 54 when stem 34 and locking barb 50 are received in lumen 80 of silicone catheter 54. Likewise, as shown and discussed with regard to FIGS. 9 and 10 above, engagement barbs 49 engage interior surface 102 of polyurethane catheter 58 when stem 34 and engagement barbs 49 are received in lumen 104 of polyurethane catheter 58.

As discussed with regard to FIG. 6, locking barb 50 enables the locking of silicone catheter 54 onto stem 34 by the interaction of locking barb 50 with compression ring 144 through silicone catheter 54. Similarly, as discussed with regard to FIG. 10, locking barb 50 enables the locking of polyurethane catheter 58 onto stem 34 by the interaction of locking barb 50 directly with attachment ridge 196 of second fastening assembly 56.

Alternative configurations of structures performing the functions of such an attachment means are possible. Such attachment structures could include, but would not be limited to, the use of a single engagement barb, two engagement barbs, or any plurality of engagement barbs. Furthermore, the locking barb and engagement barbs could be of different sizes and configurations from those already disclosed. Some of these embodiments will be shown in later figures.

In accordance with yet another aspect of the present invention there is also provided securing means that is operative when distal end 38 of stem 34 is received in the lumen of the selected catheter for performing two distinct functions. The first function is to radially, inwardly compress a portion of a body wall of the selected catheter against a portion of exterior surface 40 of stem 34. The second function of the securing means is to interact with structures performing the function of the attachment means as discussed above to preclude unintentional disengagement of the selected catheter from stem 34.

By way of example and not limitation, one form of structure capable of performing the function of such a securing means and disclosed herein includes first fastening assembly 52, as depicted in FIGS. 2–6, and second fastening assembly 56, as depicted in FIGS. 7–10.

As discussed above in greater detail, when first fastening assembly 52 is positioned as shown in FIG. 6, interior surface 68 of first locking sleeve 60 radially, inwardly compresses expansion portion 159 of silicone catheter 54 against locking barb 50 on stem 34. Interior surface 68 of first locking sleeve 60 may compress a portion of silicone catheter 54 against engagement barbs 49 but this is incidental and unnecessary for proper attachment of silicone catheter 54 to stem 34.

In like manner, when second fastening assembly 56 is positioned as shown in FIG. 10, interior surface 173 of compression sleeve 94 radially, inwardly compresses expansion portion 220 of polyurethane catheter 58 against engagement barbs 49 on stem 34.

As discussed with regard to FIGS. 6, compression ring 144 of first fastening assembly 52 interacts indirectly with locking barb 50 through silicone catheter 54 to preclude unintentional disengagement of silicone catheter 54 from stem 34. The interaction between first fastening assembly 52 and locking barb 50 is considered to be "indirect" since first fastening assembly 52 and locking barb 50 do not directly contact each other, but instead interact through silicone catheter 54. As discussed with regard to FIG. 10, attachment ridge 196 of second fastening assembly 56 interacts directly with locking barb 50 to preclude unintentional disengagement of polyurethane catheter 58 from stem 34.

Figure 12:
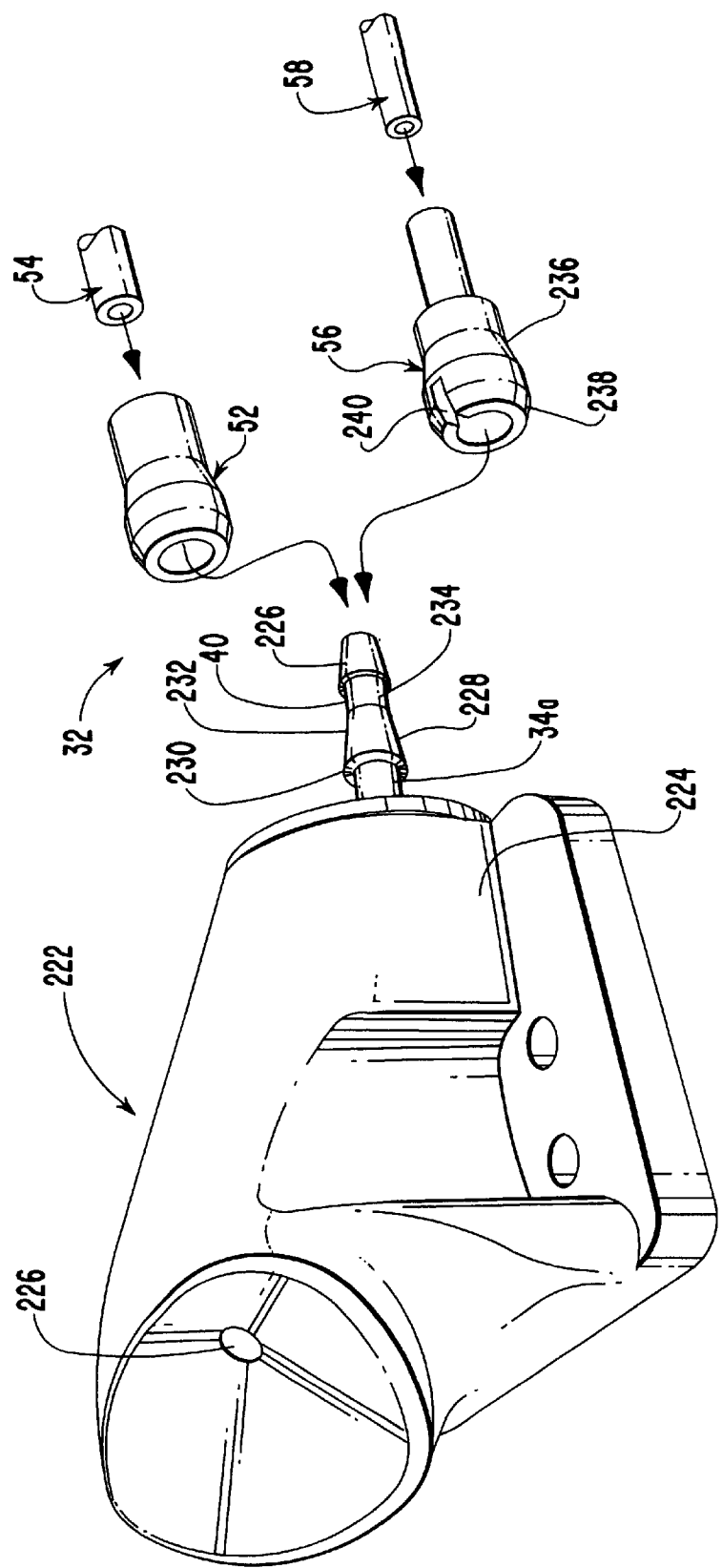
FIG. 12 is a perspective view of a second embodiment of a stem extending from a leaflet port for attachment to a catheter by use of a catheter connection system embodying teaching of the present invention.

The term "medical device" as used in the specification and appended claims is intended to include any tool, instrument, apparatus or device to which it is desirable to attach a catheter in either fluid flow communication or otherwise. The above discussed embodiment of a catheter connection system 32 has been disclosed in the context of attaching a selected catheter in fluid communication to access port 16. An alternative example of a medical device that can be used with an embodiment of catheter connection system 32 is an access port 222, depicted in FIG. 12.

Access port 222 is shown having a housing 224 with an access channel 226 leading to an leaflet valve not shown but enclosed within housing 224. Extending from housing 224 is stem 34a. In this embodiment of catheter connection system 32, a single engagement barb 226 is positioned on stem 34a as opposed to a plurality of engagement barbs, such as engagement barbs 49.

A locking barb 228 is positioned stem 34a between single engagement barb 226 and access port 222. Locking barb 228 is distinguished from locking barb 50 in that distal sidewall 128 of locking barb 50 has been eliminated from locking barb 228. Accordingly, locking barb 228 comprises a proximal sidewall 230 that is comparable to proximal sidewall 132 of locking barb 50 and a frustoconical top surface 232 that extends directly from proximal sidewall 230 to a cylindrical area 234 of stem 34a.

First fastening assembly 52 is shown for attaching silicone catheter 54 to stem 34a. Second fastening assembly 56 is shown for attaching polyurethane catheter 58 to stem 34a. In an alternative embodiment of catheter connection system 32, second locking sleeve 236 has a proximal end 238 with only a single slot 240 extending therethrough.

Figure 13:
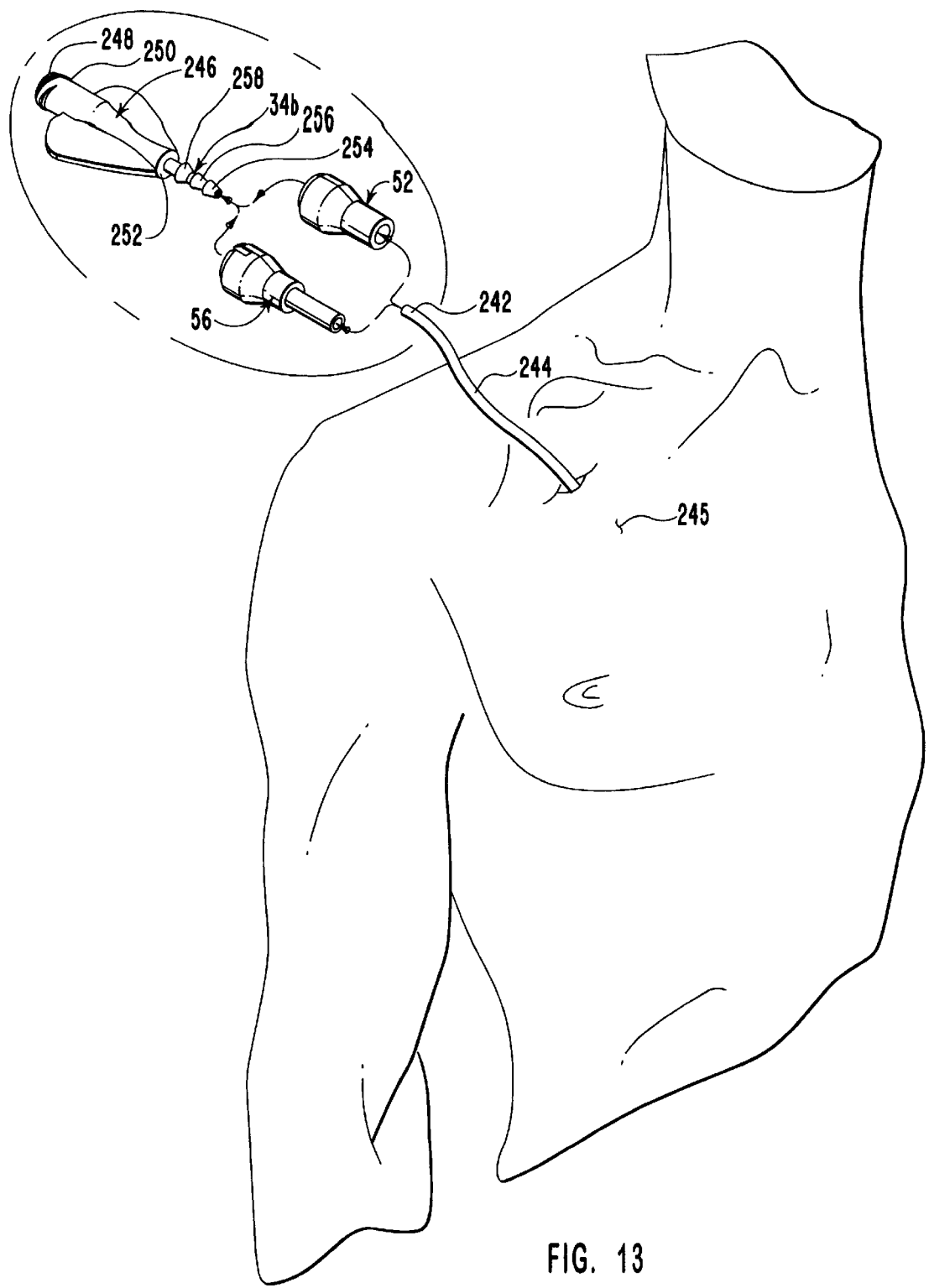
FIG. 13 is a perspective view of a proximal end of a catheter extending from a body of a patient for connection by one of a set of fastening assemblies to a catheter termination hub.

As shown in FIG. 13, another example of a medical device that accommodates a fluid flow and can be used with catheter connection system 32 is a catheter termination hub 246. Catheter termination hub 246 has a proximal end 248 with threads 250 positioned thereat for connection to an external medical device not shown and includes a distal end 252 with stem 34b extending therefrom. In the embodiment disclosed, stem 34b includes only a first engagement barb 254, a second engagement 256, and a locking barb 258. FIG. 13 also depicts a proximal end 242 of a catheter 244 extending from chest 245 of a patient for attachment to stem 34b by either first fastening assembly 52 or second fastening assembly 56, depending on the material composition of catheter 244.

Figure 14:
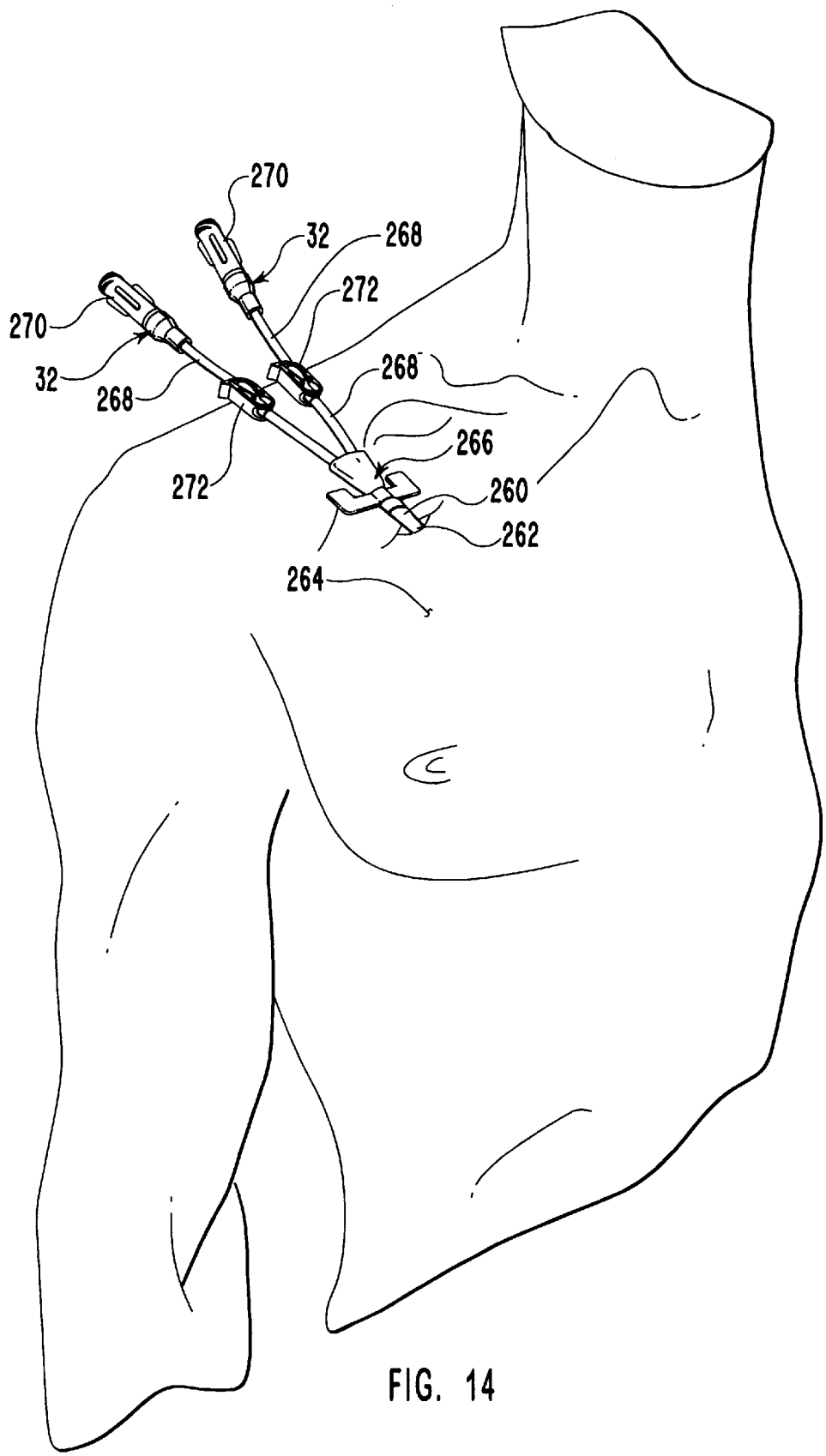
FIG. 14 is a perspective view of a proximal end of a dual lumen catheter extending from a body of a patient and having a bifurcation hub and a pair of access tubes each having a catheter termination hub secured thereto by a catheter connection system embodying teaching of the present invention.

In yet another example of how catheter connection system 32 can be used, FIG. 14 depicts a proximal end 260 of a dual lumen catheter 262 extending from chest 264 of a patient. Dual lumen catheter 262 has a bifurcation hub 266 and a pair of access tubes 268, each having a catheter termination hub 270 secured thereto by catheter connection system 32. Attached on access tubes 268 are a pair of hose clamps 272 for regulating fluid flow therein.

Figure 15:
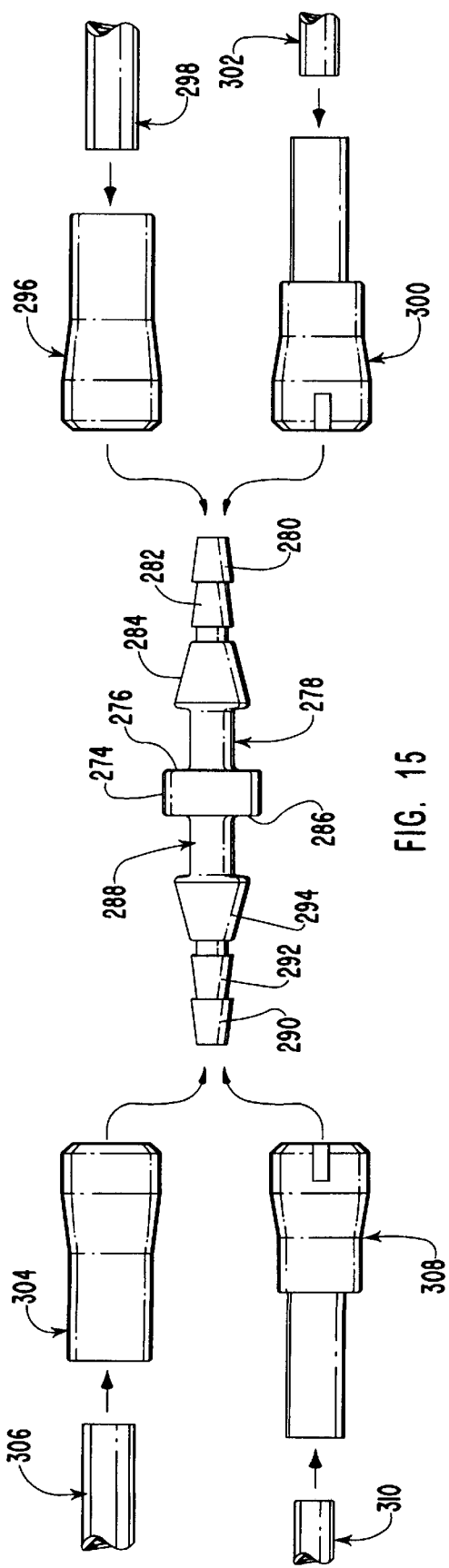
FIG. 15 is a plan view of a catheter repair or extension assembly for securing together opposing ends of different catheters using a catheter connection system embodying teaching of the present invention.

Illustrated in FIG. 15 is a catheter repair and extension stent 274 which is also another example of a medical device that can be used with an embodiment of catheter connection system 32. Extension stent 274 is used for splicing together sections of a broken catheter or for lengthening an existing catheter by attaching together opposing ends of distinct catheters. Extension stent 274 has a distal side 276 with a stem 278 extending therefrom. Positioned on stem 278 is a first engagement barb 280, a second engagement barb 282, and a locking barb 284. Extension stent 274 also has a proximal side 286 with a stem 288 extending therefrom. Positioned on stem 288 is a first engagement barb 290, a second engagement barb 292 and a locking barb 294. A passageway extends through extension stent 274 to place stem 278 and stem 288 in fluid communication.

FIG. 15 also depicts a first fastening assembly 296 for attaching a silicone catheter 298 to stem 278 and a second fastening assembly 300 for attaching a polyurethane catheter 302 to stem 278. A first fastening assembly 304 is also shown for attaching a silicone catheter 306 to stem 288 and a second fastening assembly 308 for attaching a polyurethane catheter 310 to stem 288.

Figure 16:
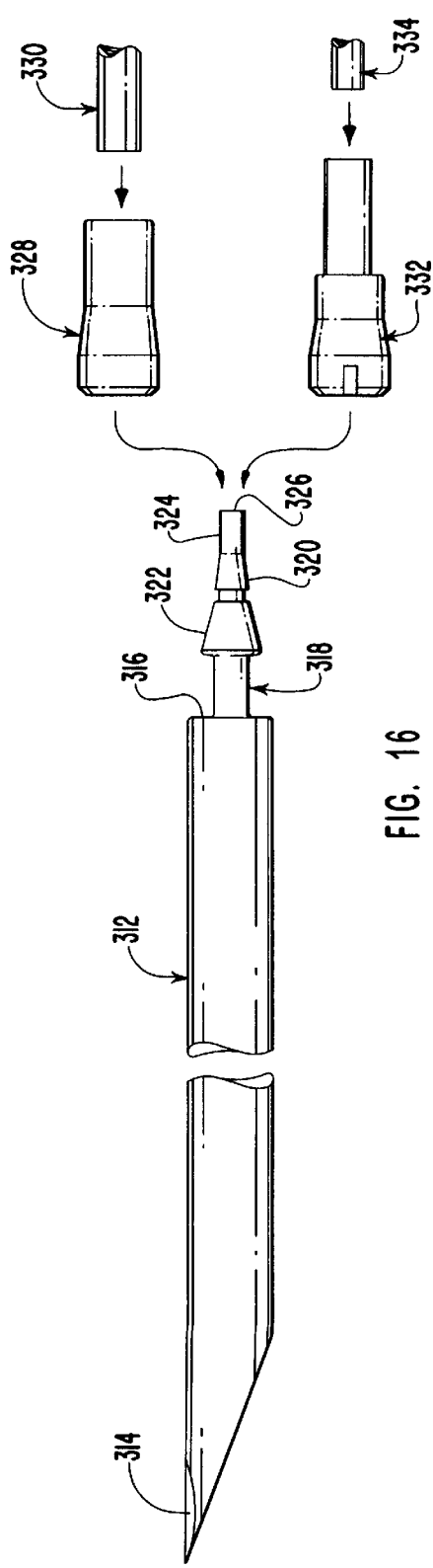
FIG. 16 is a plan view of a medical tunneling device having a stem extending therefrom for attachment to a selected catheter by a catheter connection system embodying teaching of the present invention.

The above disclosed medical devices each accommodate a fluid flow. In an alternative example, catheter connection system 32 can be used for mechanically joining a catheter to a medical tunneling device 312 as shown in FIG. 16. Tunneling device 312 does not accommodate a fluid flow but is used for threading a catheter through the tissue of a patient to a desired location within the body of the patient. Medical tunneling device 312 has a pointed distal end 314 and a base 316 with a stem 318 extending therefrom. Stem 318 has a single engagement barb 320 and a single locking barb 322 positioned distal therefrom. In further distinction from stem 34, stem 318 has a cylindrical portion 324 that projects from engagement barb 320 to a distal terminus 326. FIG. 16 also illustrates a first fastening assembly 328 for attaching a silicone catheter 330 to stem 318 and a second attachment assembly 332 for attaching a polyurethane catheter 334 to stem 318.

The previous disclosure has been primarily directed towards alternative embodiments for a catheter connection system used for effecting a mechanical joinder and a fluid tight coupling between a medical device and a selected catheter chosen from a set of two single lumen catheters. The present invention, however, also encompasses a catheter connection system used for effecting a fluid-tight coupling and a mechanical joinder between a medical device that accommodates two separate fluid flows and a selected dual lumen catheter chosen from a set of two dual lumen catheters.

Figure 17:
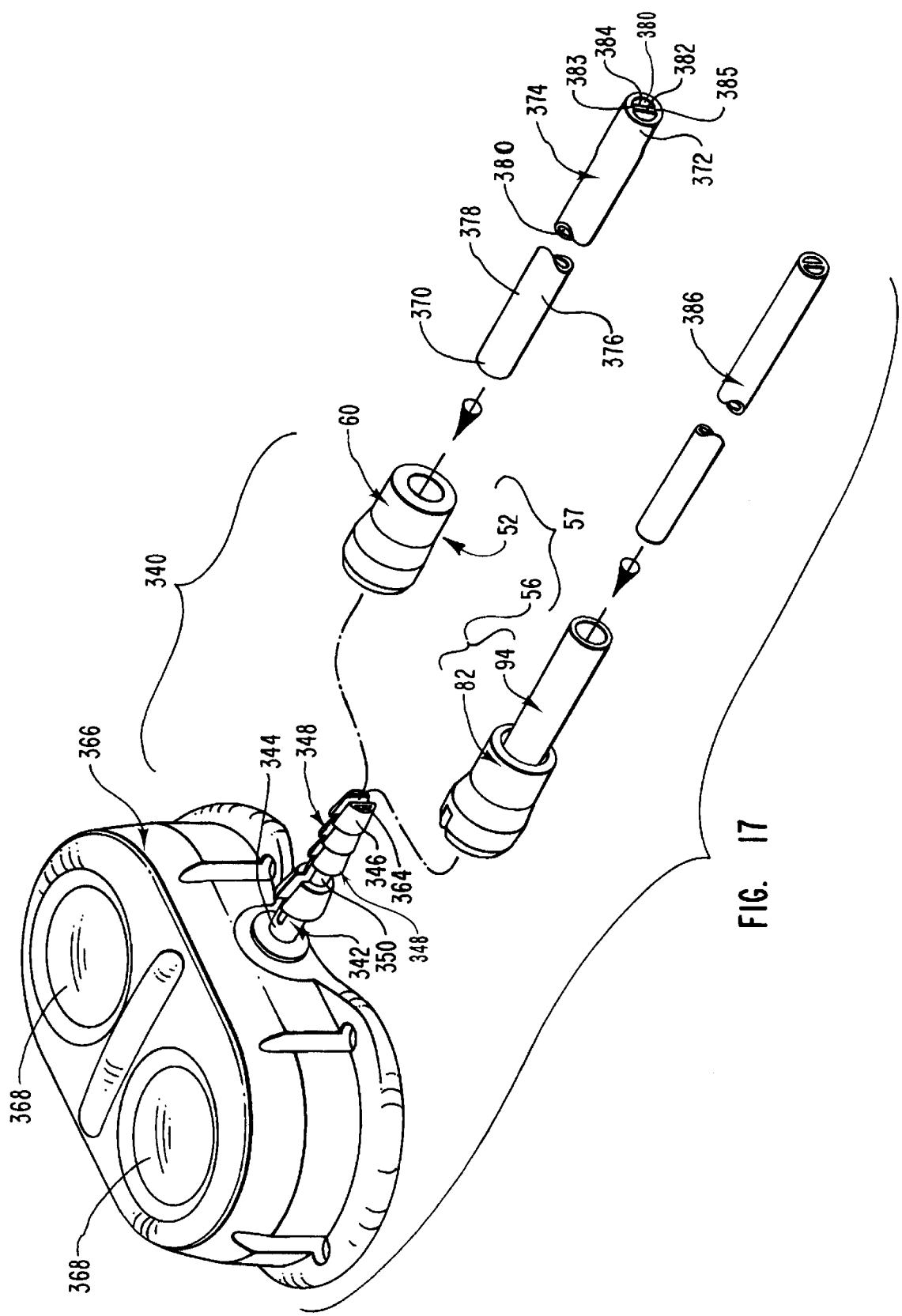
FIG. 17 is a perspective view of an implantable dual reservoir access port with a catheter connection system thereof embodying teachings of the present invention and in a dissembled condition, the catheter connection system including generally a dual passage stem extending from the access port and a set of fastening assemblies individually corresponding to a dual lumen silicone catheter and a dual lumen polyurethane catheter.

FIG. 17 discloses one embodiment of a catheter connection system 340 incorporating features of the present invention. As disclosed therein, catheter connection system 340 comprises a stem 342 having a proximal end 344 and an opposing distal end 346. As better shown in FIG. 18, positioned at distal end 346 are a pair of adjacent prongs 348 extending between a first end 354 and a distal terminus 356. Each prong 348 is defined by an exposed exterior surface 350 and an exposed inside face 352. Each inside face 352 is adjacently facing and separated by a gap G. Each of prongs 348 have an interior surface 362 that defines a passage 364 longitudinally extending through each respective prong 348 of stem 342. Referring again to FIG. 17, proximal end 344 of stem 342 is shown being attached to a dual reservoir port 366. Passage 364 in each of prongs 348 communicates with a respective fluid reservoir 368 within dual reservoir port 366.

The present invention also provides for retaining means on exposed exterior surface 350 of each of prongs 348. The retaining means is for engaging the interior surface of each of the lumens of the selected dual lumen catheter, as will be discussed below. This is accomplished when distal end 346 of each of prongs 348 is individually received in individual of the lumens of the selected dual lumen catheter. The retaining means also enables locking of the selected dual lumen catheter on stem 342.

Figure 18:
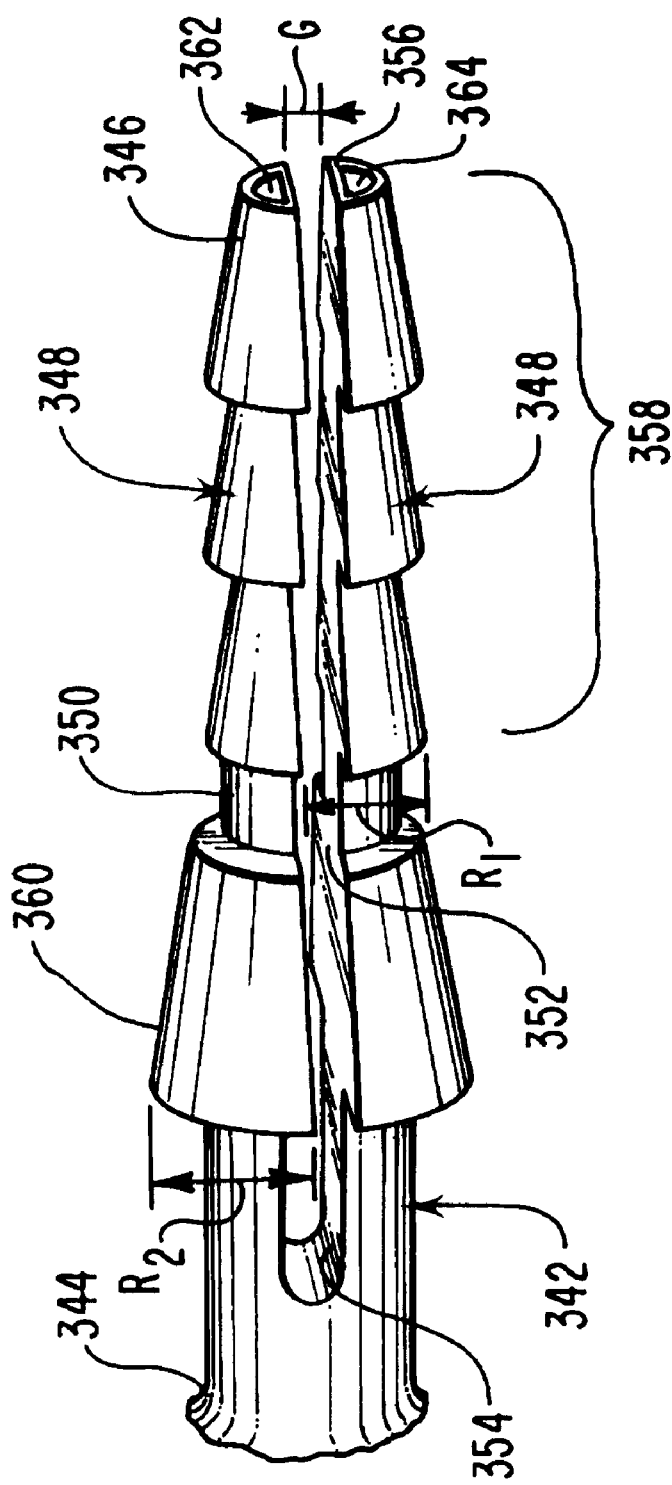
FIG. 18 is an enlarged perspective view of the stem shown in FIG. 17.

By way of example of the retaining means and not by limitation, consecutively positioned at distal end 346 of each of prongs 348 are a set of three complementary sized engagement barbs 358. As seen in FIG. 18, engagement barbs 358 span across and radially extend from exposed exterior surface 350. Corresponding engagement barbs 358 are aligned on each of opposing prongs 348. Each of engagement barbs 358 is shown as having a maximum outer radius $R_1$ as measured from a longitudinal axis extending through stem 342. Although three engagement barbs 358 are shown, alternative embodiments are also envisioned in which one, two, or even four or more engagement barbs 358 are used.

Positioned proximal of engagement barbs 358 on prongs 348 is a locking barb 360. Locking barb 360 also spans and radially extends from exposed exterior surface 350 of each of prongs 348. Locking barb 360 is defined as having a maximum outer radius $R_2$ that is larger than the maximum outer radius $R_1$ of engagement barbs 358. Engagement barbs 358 and locking barb 360 have substantially the same configuration and structural elements as engagement barbs 49 and locking barb 50 as previously discussed in FIG. 3. The primarily distinction is that engagement barbs 358 and locking barb 360 do not bridge gap cap G to completely encircle stem 342.

FIG. 17 further reveals catheter connection system 340 as including first fastening assembly 52 and second fastening assembly 56 as previously discussed with regards to FIG. 2. In distinction to the previous disclosure, however, first fastening assembly 52 is now used in conjunction with an elongated, pliable, dual lumen, silicone catheter 374. Catheter 374 is defined as having a body wall 376 with an exterior surface 378 extending between a proximal end 370 and a distal end 372. Catheter 374 also has an interior surface 380. A partition wall 382 extends between two spaced locations 383 and 385 on interior surface 380 to form two distince longitudinally extending, fluid flow lumens 384 within body wall 376.

In a similar fashion, second fastening assembly 56 operates in conjunction with an elongated, dual lumen pliable, polyurethane catheter 386. Polyurethane catheter 386 has the same configuration and structural elements as silicone catheter 374. Accordingly, the reference characters used to identify the structural elements of silicone catheter 374 will also be used to identify the structural elements of polyurethane catheter 386.

The present invention also provides clasping means operative when distal end 346 of each of prongs 348 is individually received in individual of lumens 384 of the selected dual lumen catheter. The clasping means is for radially, inwardly compressing a portion of the body wall of the selected dual lumen catheter against a portion of the attachment means on each of prongs 348. The clasping means also interacts with the attachment means to preclude unintentional disengagement of the selected catheter from stem 342. By way of example and not by limitation, the clasping means includes first fastening assembly 52, second fastening assembly 56, and all alternative embodiments as previously discussed therewith.

Figure 19:
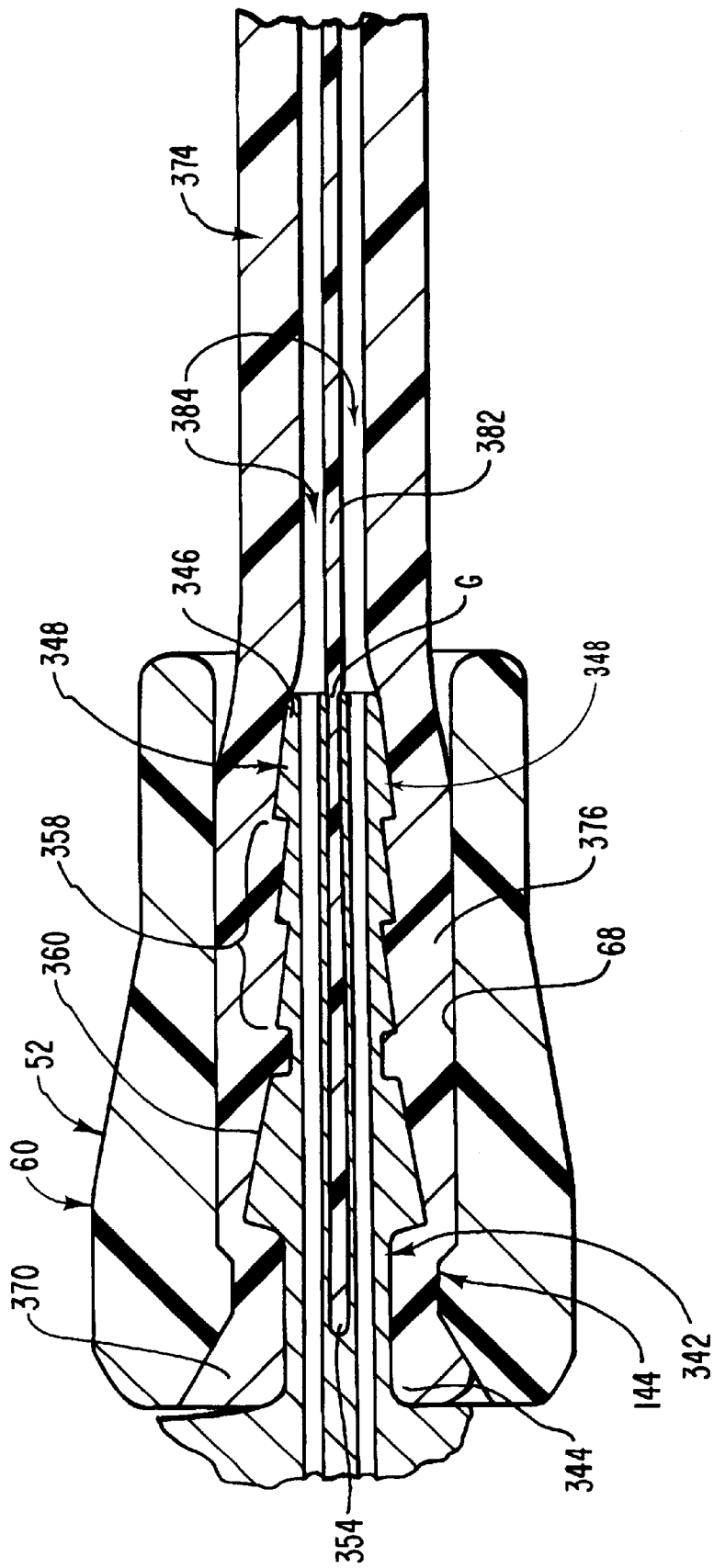
FIG. 19 is an elevation view in full cross section of a dual lumen silicone catheter and the elements of the catheter connection system of FIG. 17 shown in an assembled condition.

FIG. 19 illustrates the assembly of silicone catheter 374 and stem 342 with first fastening assembly 52. Initially, distal end 346 of each of prongs 348 is individually received within proximal end 370 of a respective one of lumens 384, so that partition wall 382 is positioned between prongs 348. As prongs 348 are advanced within lumens 384, silicone catheter 374 radially expands outward to pass over engagement barbs 358 and locking barb 360.

Once locking barb 360 is received within lumens 384, first fastening assembly 52, comprising first locking sleeve 60, is advanced over silicone catheter 374 having stem 342 received therein. First locking sleeve 60 is advanced until compression ring 144 passes over locking barbs 360 and is positioned between locking barbs 360 and proximal end 344 of stem 342. Compression ring 144 has a slightly larger inner diameter $H_2$, as shown in FIG. 4, than the combined maximum outer radius of the opposing locking barbs 360. This allows compressions ring 144 to pass over locking barbs 360 and yet still compress silicone catheter 374 against stem 342.

In the assembled condition, compression ring 144 and interior surface 68 of first locking sleeve 60 radially, inwardly compresses body wall 376 of silicone catheter 374 against each locking barb 360 and stem 342 to create a fluid-type coupling between stem 342 and silicone catheter 374. Furthermore, the interaction among compression ring 144, silicone catheter 374, and locking barb 360 creates a mechanical joinder therebetween which precludes unintentional disengagement of silicone catheter 374 and stem 342.

In the embodiment as shown in FIG. 19, interior surface 68 of first locking sleeve 60 also compresses body wall 376 against engagement barbs 358. Although unnecessary, the interaction between engagement barbs 358 and body wall 376 assists in the formation of the liquid tight seal and the mechanical joinder between stem 342 and silicone catheter 374.

Furthermore, to ensure a proper seal between stem 342 and silicone catheter 374, interior surface 68 of first locking sleeve 60 is shown configured to apply a radially inward load at distal end 346 of each of prongs 348. The inward load compresses partition wall 382 of silicone catheter 374 between prongs 348. As such, gap G is shown being smaller at distal end 346 than at first end 354.

The assembly of polyurethane catheter 386 with stem 342 using second fastening assembly 56 is performed in substantially the same manner as discussed with the assembly of stem 34 and polyurethane catheter 58. This process is discussed in detail with regard to FIGS. 9 and 10. The main distinctions are that partition wall 382 is positioned between prongs 348 and second fastening assembly 56 is configured so that distal ends 346 of prongs 348 compress partition wall 382 therebetween.

The catheter connection systems disclosed above are each directed towards systems for attaching one of two different catheters to a stem. The present invention also envisions catheter connection systems for selectively attaching one of three or more different catheters to a stem. By way of example and not by limitation, disclosed in FIG. 20 is a catheter connection system 394 incorporating features of the present invention.

Figure 20:
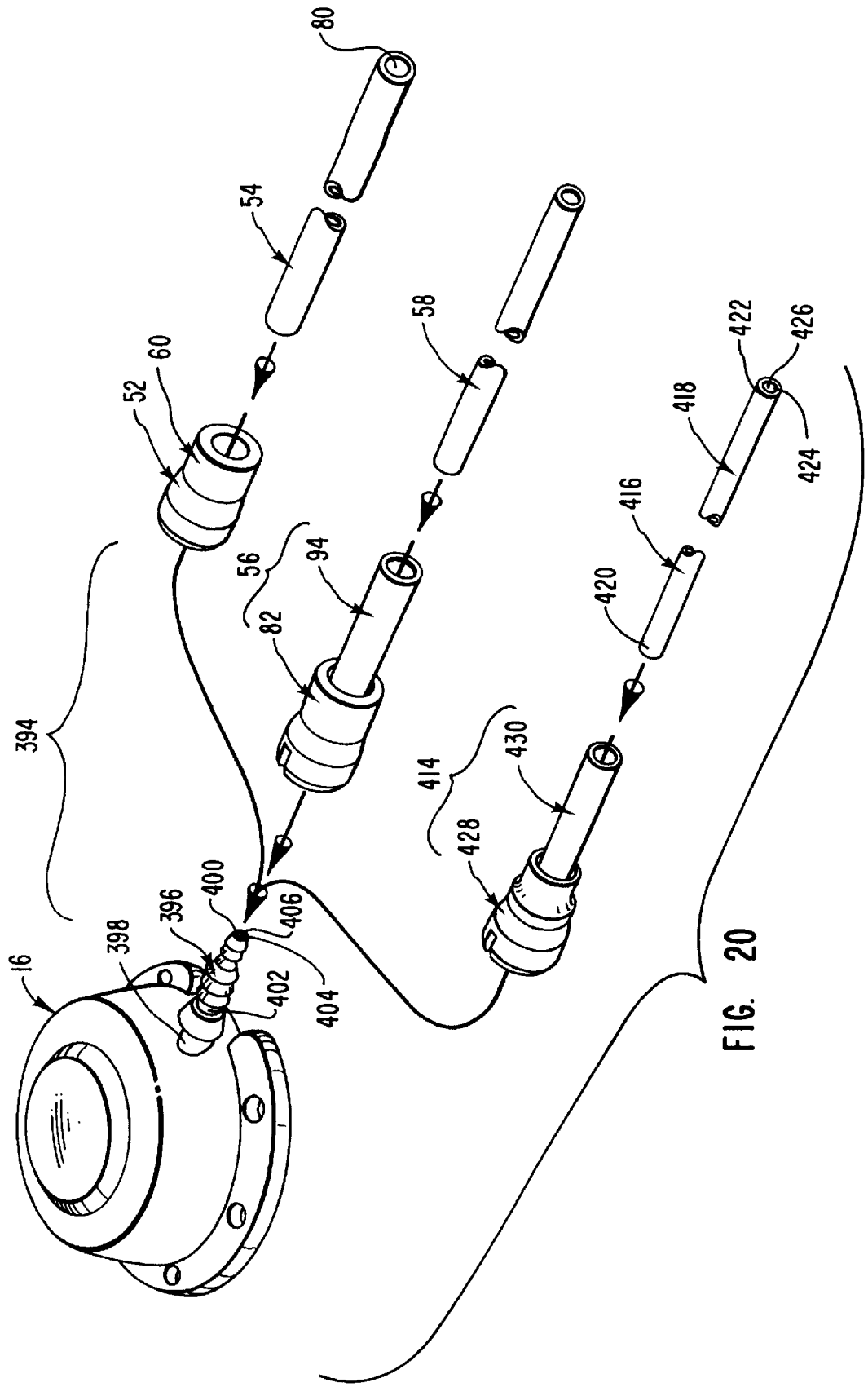
FIG. 20 is a perspective view of an implantable access port with the catheter connection system thereof embodying teachings of the present invention and in disassembled condition, the catheter connection system including generally a single passage stem extending from the access port and a set of fastening assemblies individually corresponding to a silicone catheter, a large polyurethane catheter, and a small polyurethane catheter.

As disclosed in FIG. 20, catheter connection system 394 includes a stem 396 having a free distal end 400 and an opposing proximal end 398 attached to access port 16. Stem 396 is further defined as having an exterior surface 402 and an interior surface 404. Interior surface 404 defines a passageway 406 extending through stem 396 and communicating with access port 16. As better seen in FIG. 21, exterior surface 402 is further defined as having a distal portion 405 positioned at distal end 400 and a proximal portion 407 positioned proximal of distal portion 405. Proximal portion 407 is shown as having an outer diameter larger than the outer diameter of distal portion 405.

The present invention also provides anchoring means on exterior surface 402 of stem 396 for engaging the interior surface of a selected catheter when distal end 400 of stem 396 is received in the lumen of the selected catheter. The anchoring means also enables locking of the selected catheter on stem 396. By way of example and not by limitation, anchoring means is shown in FIG. 21 as comprising a first set of engagement barbs 408 encircling and radially outwardly extending on distal portion 405 of exterior surface 402 of stem 396.

Positioned proximal to first set of engagement barbs 408 is a second set of engagement barbs 410. Second set of engagement barbs 410 encircles and radially, outwardly extends on proximal portion 407 of exterior surface 402 of stem 396. Second set of engagement barbs 410 have a maximum outer diameter that is larger than the maximum outer diameter of first set of engagement barbs 408.

There are of course several different possible embodiments of a stem, such as stem 396 in which second set of engagement barbs 410 have a larger outer diameter than first set of engagement barbs 408. For example, in one embodiment stem 396 could be substantially cylindrical along its length. Engagement barbs 408 and 410 could then yet be used in which individual barbs of second set of engagement barbs 410 have a greater height than that of first set of engagement barbs 408. Alternatively, engagement barbs 408 and 410 could have the same height but be placed on portions of the stem 396 having different diameters, such as distal portion 405 and proximal portion 407 of stem 396. FIG. 21 shows engagement barbs 408 and 410 having both different heights and being placed at different sized portions of stem 396.

Although engagement barbs 408 and 410 are shown as each comprising three individual barbs, it is also envisioned that first and second set of engagement barbs 408 and 410 could each comprise a single barb, two barbs, or four or more barbs.

Positioned between second set of engagement barbs 410 and proximal end 398 of stem 396 is a locking barb 412. Locking barb 412 encircles and radially outwardly extends on exterior surface 402 of stem 396. Furthermore, locking barb 412 has a maximum outer diameter that is larger than the maximum outer diameter of second engagement barbs 410. Locking barb 412 and second engagement barbs 410 have substantially the same configuration and structural elements as locking barb 50 and engagement barbs 49 discussed with FIG. 3.

As shown in FIG. 20, catheter connection system 394 also includes first fastening assembly 52, second fastening assembly 56, and a third fastening assembly 414. First fastening assembly 52 is used for joining silicone catheter 54 to stem 396. This process is accomplished in substantially the same manner as discussed with FIGS. 5 and 6, where silicone catheter 54 is joined to stem 34. Stem 396 is advanced within lumen 80 of catheter 54 until catheter 54 passes over locking barb 412. First fastening assembly 52, comprising first locking sleeve 60, is then advanced along silicone catheter 54 until compression ring 144 is positioned between locking barb 412 and proximal end 398 of stem 396.

First set of engagement barbs 408 are used for the attachment of polyurethane catheter 416 and do not significantly affect the attachment of silicone catheter 54. Since first set of engagement barbs 408 are smaller than second set of engagement barbs 410, first set of engagement barbs 408 will often not contact the interior of silicone catheter 54. It is preferred, however, that first fastening assembly 52 have a length sufficient to cover the full length of stem 396 in an assembled condition. This helps to prevent damage to the stem and kinking of the selected catheter.

Second fastening assembly 56 is used for joining polyurethane catheter 58 to stem 396. This process is accomplished in substantially the same manner as discussed with FIGS. 9 and 10, where polyurethane catheter 58 is shown joined to stem 34.

To do so, stem 396 is received in the lumen of polyurethane catheter 58, and polyurethane catheter 58 is advanced upon stem 396 toward access port 16. The interior of polyurethane catheter 58 while clearing first engagement barbs 408 of stem 396, engages second set of engagement barbs 410 as polyurethane catheter 58 is advanced toward access port 16. Eventually, the proximal end of polyurethane catheter 58 will abut the distal face of locking barb 412. Fastening assembly 56 is then advanced along polyurethane catheter 58 toward access port 16, over the portion of polyurethane catheter 58 dispersed on stem 396, into locking engagement with locking barb 412. The portion of compression sleeve 94 inside locking sleeve 82 then urges polyurethane catheter 58 into a sealing engagement with second set of engagement barbs 410.

Third fastening assembly 414 is designed for joining a polyurethane catheter 416 to stem 396. Polyurethane catheter 416 has an exterior surface 418 extending between a proximal end 420 and an opposing distal end 422. Polyurethane catheter 416 also has an interior surface 424 defining a lumen 426 longitudinally extending therethrough. Polyurethane catheter 416 is distinguished from polyurethane catheter 58 in that polyurethane catheter 416 has an inner diameter that is smaller than that of polyurethane catheter 58.

As disclosed in FIG. 21, third fastening assembly 414 comprises a locking sleeve 428 and a compression sleeve 430. Locking sleeve 428 comprises a proximal end 432, a distal end 434 and a passageway 436 extending therebetween. Positioned at proximal end 432 are a pair of resilient C-shaped clamps 438 that are configured comparable to C-shaped clamps 182 and 184 as discussed with regard to FIGS. 7 and 8. Passageway 436 is further defined by a first interior surface 440 position distal of C-shaped clamps 438. Passageway 436 is further defined by a second interior surface 442 positioned distal of first interior surface 440. Second interior surface 442 has an inside diameter that is smaller than the inside diameter of first interior surface 440. Radially extending inward from second interior surface 442 at distal end 434 is a retaining ring 444.

Compression sleeve 430 has an exterior surface 446 extending between a proximal end 448 and a distal end 450. Compression sleeve 430 further includes an interior surface 452 defining a passageway 454 extending therethrough. Compression sleeve 430 is configured to at least partially reside within passageway 436 of locking sleeve 428. To this end, exterior surface 446 of compression sleeve 430 comprises a first portion 456 positioned at proximal end 448 and configured to fit within first interior surface 440. Exterior surface 446 further includes a second portion 458 positioned distal of first portion 456 and configured to reside within second interior surface 442. Finally, compression sleeve 430 includes a tail portion 460 extending distally of second portion 458 and having an outside diameter smaller than second portion 458. Accordingly, as shown in FIG. 22, when compression sleeve 430 is positioned within locking sleeve 428, tail 460 projects distally of locking sleeve 428.

Referring again to FIG. 21, interior surface 452 of compression sleeve 430 is also defined as including a first portion 462 positioned at proximal end 448 and a second portion 464 positioned at distal end 450. Second portion 464 is shown as having a smaller inner diameter than the inner diameter of first portion 462.

During assembly as shown in FIG. 22, first set of engagement barbs 408 on stem 396 are received within proximal end 420 of polyurethane catheter 416. Once so configured, polyurethane catheter 416 is received within passageway 454 of compression sleeve 430. Third fastening assembly 414 is then advanced along silicone catheter 416 until C-shaped clamps 438 expand, pass over, and lock on the proximal side of locking barb 412. In this configuration, second portion 464 of interior surface 452 compresses polyurethane catheter 416 against first set of engagement barbs 408, thereby effecting a mechanical joinder and a liquid-tight coupling between polyurethane catheter 416 and stem 396.

Thus, the present invention includes clinching means operative when distal end 400 of stem 396 is received in a lumen of a selected catheter. The clinching means radially inwardly compresses a portion of the body wall of the selected catheter against a portion of the anchoring means on stem 396. Furthermore, the clinching means interacts with the anchoring means to preclude unintentional disengagement of the select catheter from stem 396. By way of example and not by limitation, the clinching means includes first fastening assembly 52, second fastening assembly 56, and third fastening assembly 414, and all alternative embodiments previously discussed therewith. Other alternative embodiments for the clinching means will be discussed later in the disclosure.

FIG. 23 discloses stem 396 having an alternative embodiment of the anchoring means positioned on exterior surface 402. As disclosed therein, the anchoring means comprises a first set of engagement barbs 466 encircling and radially extending from distal portion 405 of exterior surface 402. A second set of engagement barbs 468 are positioned proximal of first set of engagement barbs 466. Second set of engagement barbs 468 encircle and radially extend outward from proximal portion 407 of exterior surface 402. Second set of engagement barbs 468 have a larger outer diameter than the outer diameter of first set of engagement barbs 466.

The anchoring means further includes a first locking barb 470 encircling and radially extending outward on exterior surface 402 of stem 396. First locking barb 470 is positioned between first set of engagement barbs 466 and second set of engagement barbs 466. A cylindrical portion 469 of stem 396 separates first locking barb 470 and second set of engagement barbs 468. First locking barb 470 is designed as having a maximum outer diameter larger than the maximum outer diameter of first set of engagement barbs 466. Finally, a second locking barb 472 encircling and radially outwardly extends from exterior surface 402 between proximal end 398 and second set of engagement barbs 468. Second locking barb 472 has a maximum outer diameter larger than the maximum outer diameter of second set of engagement barbs 468.

The anchoring means disclosed on stem 396 in FIG. 23 facilitate the attachment of four or more different catheters. For example, using the same process as described with FIGS. 5 and 6, silicone catheter 54 can be secured around second locking barb 472 of stem 396 using first fastening assembly 52. Furthermore, using the same process as described with FIGS. 9 and 10, polyurethane catheter 58 can be secured around second engagement barbs 468 of stem 396 using second fastening assembly 56.

Next, referring to FIG. 24, a silicone catheter 474 having an inner diameter smaller than silicone catheter 54 can also be attached to stem 396. Silicone catheter 474 has a proximal end 476 and an interior surface 477 defining a lumen 478 longitudinally extending therethrough. To facilitate attachment, first locking barb 470 performs the same function for silicone catheter 474 as second locking barb 472 performs for the attachment of silicone catheter 54. During attachment, distal end 400 of stem 396 is advanced within lumen 478 of silicone catheter 474 until cylindrical portion 469 is received within lumen 478.

A first fastening assembly 480 is then used to secure silicone catheter 474 to stem 396. First fastening assembly 480 has substantially the same configuration and structural elements as first fastening assembly 52 disclosed in FIG. 4. Accordingly, the same reference characters used to identify the elements of first fastening assembly 52 will be used to identify the references characters of first fastening assembly 480. The primary distinction between first fastening assemblies 52 and 480 is that first fastening assembly 480 has a relatively small inner diameter that allows fastening assembly 480 to mechanically interact with first locking barb 470.

Once stem 396 is received within lumen 478, first fastening assembly 480 is advanced over silicone catheter 474 having stem 396 received therein. Fastening assembly 480 advances until compression ring 144 advances over first locking barb 470. In this position, compression ring 144 compress silicone catheter 474 between first locking barb 470 and second set of engagement barbs 468, thereby creating a sealed connection and mechanical joinder between silicone catheter 474 and stem 396.

Finally, referring to FIG. 25, a polyurethane catheter 486 having an inner diameter smaller than polyurethane catheter 58 can be attached to stem 396. Polyurethane catheter 486 has a proximal end 487 with an interior surface 488 defining a lumen 490 longitudinally extending therethrough. Polyurethane catheter 486 is attached to stem 396 using a second fastening assembly 492. Second fastening assembly 492 has substantially the same configuration and structural elements as second fastening assembly 56 disclosed with FIGS. 7 and 8. Accordingly the same reference character used with second fastening assembly 56 will also be used with second fastening assembly 492.

The distinction between second fastening assemblies 56 and 492 is that assembly 492 has a smaller inner diameter than assembly 56. This enables assembly 492 to secure polyurethane catheter 486 to first set of engagement barbs 466 and first locking barb 470 in the same manner that second fastening assembly 56 secures polyurethane catheter 58 to engagement barbs 49 and locking barb 50, as discussed with FIGS. 9 and 10.

In general, first set of engagement barbs 466 are received within lumen 490 of polyurethane catheter 486. Preferably, stem 396 is advanced until catheter 486 contacts first locking barb 470. Fastening assembly 492 is then advanced over polyurethane catheter 486 until C-shaped clamps 182 and 184 advance over and lock against the proximal side of first locking barb 470.

The present invention also envisions other alternative catheter connection systems for securing a selected catheter chosen from three or more catheters to a medical device. FIG. 26 discloses a stem 496 having a proximal end 498 for attachment to a medical device and an opposing distal end 500. Stem 496 is shown having an exterior surface 502 defined by a cylindrical portion 504 positioned at proximal end 498 and an annular frustoconical portion 506 positioned distal of cylindrical portion 504.

The anchoring means on exterior surface 504 of stem 496 include a plurality of engagement barbs 508 encircling and radially, outwardly, extending on frustoconical portion 506 of stem 496. Each consecutive one of plurality of engagement barbs 508 have a maximum outer diameter that incrementally decreases in size towards distal end 500 of stem 496.

Furthermore, a locking barb 510 is positioned proximal of the plurality of engagement barbs 508. Locking barb 510 encircles and radially, outwardly, extends on exterior surface 502 of stem 496. Locking barb 510 has a maximum outer diameter that is larger than the maximum outer diameter of each of plurality of engagement barbs 508.

Stem 496 in FIG. 26 is contrasted to stem 34 in FIG. 3 primarily by the fact that the plurality of engagement barbs 508 taper or decrease in outer diameter as opposed to engagement barbs 49 which all have substantially the same outer diameter. This tapering of the plurality of engagement barbs 508 allows for the attachment of a variety of polyurethane catheters having different lumen sizes. For example, disclosed in FIG. 25 is a polyurethane catheter 512 having an interior surface 514 defining a lumen 516.

Polyurethane catheter 512 has an inside diameter that permits only a portion of plurality of engagement barbs 508 to be received within lumen 516. Once stem 496 is advanced within polyurethane catheter 512, second fastening assembly 56 is advanced over polyurethane catheter 512 until C-shaped clamps 182 and 184 expand over and lock against the proximal side of locking barb 510. This step is accomplished in substantially the same way as the attachment of first fastening assembly 56 to locking barb 50 discussed with respect to FIGS. 9 and 10.

In the present embodiment, even though polyurethane catheter 512 does not cover all of the plurality of engagement barbs 508, second fastening assembly 56 compresses polyurethane catheter 512 against the adjacent plurality of engagement barbs 508 thereby sealing and securing polyurethane catheter 512 against stem 496.

In an alternative use, FIG. 27 discloses a polyurethane catheter 518 as having an inner diameter larger than the inner diameter of polyurethane catheter 512. Polyurethane catheter 518 has an interior surface 520 defining a lumen 522 longitudinally extending therethrough. During assembly, as shown in FIG. 27, stem 496 can be advanced within lumen 522 until polyurethane catheter 518 touches locking barb 510. Once so positioned, second fastening assembly 56 is positioned over stem 496 received within polyurethane catheter 518, thereby sealing and securing polyurethane catheter 518 to stem 496. Using the same approach as discussed with FIGS. 25 and 26, a plurality of polyurethane catheters having lumens of different inside diameters can be secured to stem 496.

Stem 496 can also be secured to a silicone catheter. This is accomplished using first fastening assembly 52 in substantially the same process as previously described in FIGS. 5 and 6. Namely, stem 496 is advanced within the lumen of the silicone catheter until locking barb 510 is received within the lumen. First fastening assembly 52 is then advanced along the silicone catheter until compression ring 144 is positioned proximal of locking barb 510.

Disclosed in FIG. 28 is yet another embodiment of a catheter connection system for mechanically joining a selected catheter chosen from three or more catheters to a medical device. As shown in FIG. 28, a stem 530 is provided having a free distal end 534 and an opposing proximal end 532 for attachment to a medical device. Stem 530 further has an exterior surface 536 on which anchoring means are positioned.

The anchoring means are shown as comprising a first set of engagement barbs 538 positioned at distal end 534. First set of engagement barbs 538 encircle and radially, outwardly extend on exterior surface 536. Each one of first set of engagement barbs 538 have a maximum outer diameter that decreases toward distal end 534 of stem 530.

Positioned proximal of first set of engagement barbs 538 is a second set of engagement barbs 540. Second set of engagement barbs 540 also encircle and radially outwardly extend from exterior surface 536 of stem 530. Each one of second set of engagement barbs 540 have a maximum outer diameter that incrementally decreases towards distal end 534 of stem 530. Furthermore, each one of second set of engagement barbs 540 have a maximum outer diameter that is larger than the maximum outer diameter of each one of first set of engagement barbs 538. First set of engagement barbs 538 and second set of engagement barbs 540 are separated by a substantially cylindrical portion 542 of stem 530.

Positioned between proximal end 532 of stem 530 and second set of engagement barbs 540 is a locking barb 541. Second set of engagement barbs 540 are separated from locking barb 541 by a substantially cylindrical second portion 543 of stem 530. Locking barb 541 encircles and radially outwardly extends on exterior surface 536. Furthermore, locking barb 541 has a maximum outer diameter that is larger than the maximum outer diameter of each one of second set of engagement barbs 540.

Stem 530 with the anchoring means positioned thereon is in part designed for the attachment of a composite catheter. The term "composite catheter" as used in the specification and appended claims is intended to refer to a catheter having at least two layers of different material. By way of example and not by limitation, FIG. 28 discloses a composite catheter 544 having a tubular outside layer 546 housing a tubular inside layer 548. In the embodiment shown, outside layer 546 is made of polyurethane while inside layer 548 is made of silicone. Individual of layers 546 and 548 could also be made from materials such as plastics, rubbers, mesh, or fibers. Composite catheter 544 is further defined as having a proximal end 550 and an interior surface 552 defining a lumen 554 longitudinally extending therethrough.

Composite catheter 544 is fluid coupled and mechanically joined to stem 530 by a fourth fastening assembly 555. Fourth fastening assembly 555 comprises a locking sleeve 556 having a proximal end 558 and an opposing distal end 560. Locking sleeve 556 further includes an interior surface 562 defining a passageway 564 longitudinally extending therethrough. An annular compression ring 566 radially inwardly extends from interior surface 562. Interior surface 562 is defined by a substantially cylindrical first portion 568 positioned proximal of annular compression ring 566 and a substantially cylindrical second portion 570 positioned distal of annular compression ring 566.

Figure 29:
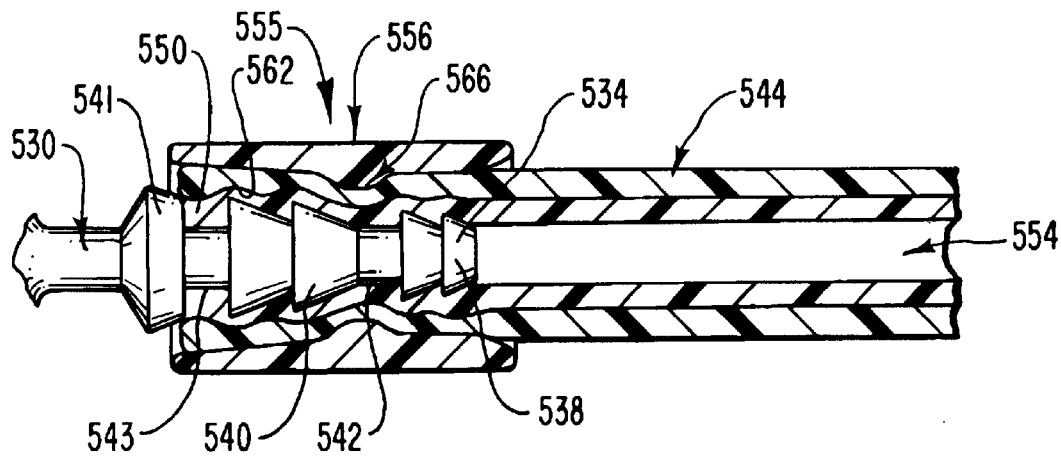
FIG. 29 is an elevation view in partial cross section of the catheter connection system of FIG. 28 in an assembled condition.

In an assembled condition as shown in FIG. 29, distal end 534 of stem 530 is advanced within lumen 554 until proximal end 550 of composite catheter 544 contacts locking barb 541. Next, locking sleeve 555 is advanced over composite catheter 544 having stem 530 positioned therein until annular compression ring 566 is positioned between first set of engagement barbs 538 and second set of engagement barbs 540. In this position, interior surface 562 and compression ring 566 compresses composite catheter 544 against first set of engagement barbs 538 and second set of engagement barbs 540, thereby producing a mechanical joiner and fluid coupling between stem 530 and composite catheter 544.

In the same way that composite catheter 544 is mechanically joined and fluid coupled to stem 530, a polyurethane catheter can also be secured to stem 530. That is, stem 530 is advanced within the lumen of a polyurethane catheter until the polyurethane catheter comes in contact with locking barb 541. Locking sleeve 556 is then advanced over polyurethane catheter until compression ring 566 is positioned between first set of engagement barbs 538 and second set of engagement barbs 540.

In yet another alternative use, stem 530 can also be used for attachment to a silicone catheter. This is accomplished using first fastening assembly 52 in substantially the same way that silicone catheter 54, as previously discussed in FIGS. 5 and 6, is secured to stem 16. Namely, stem 530 is advanced within the lumen of a silicone catheter until locking barb 541 is received within the lumen. First fastening assembly 52 is then advanced along the silicone catheter until compression ring 144 passes over locking barb 541, thereby securing the silicone catheter to stem 530.

Figure 30:
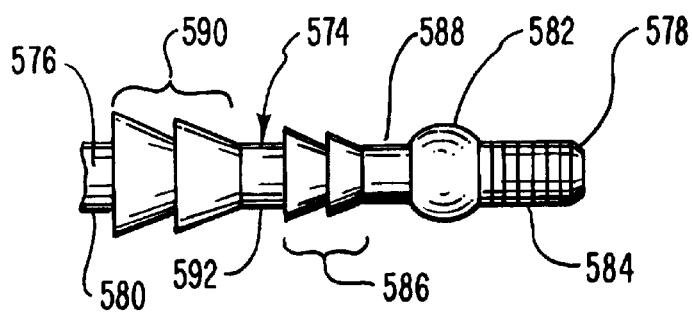
FIG. 30 is an elevation view of a fourth embodiment of a stem useable in the multiple-type catheter connection system of FIG. 20.

FIG. 30 discloses a stem 574 having yet another alternative embodiment for the anchoring means. Stem 574 includes a proximal end 576 for attachment to a medical device and an opposing free distal end 578. Stem 574 further includes an exterior surface 580 having the anchoring means positioned thereon. As disclosed in FIG. 30, the anchoring means includes an engagement bulb 582 encircling and radially extending outward on exterior surface 580.

Projecting distal of engagement bulb 582 is a substantially cylindrical first portion 584 of stem 574. First portion 584 terminates at distal end 578. Positioned proximal of engagement bulb 582 is a first set of engagement barbs 586. First set of engagement barbs 586 encircle and radially extend outward on exterior surface 580. Each one of said first set of engagement barbs 586 has a maximum outer diameter that decreases in size towards distal end 578 of stem 574. The largest maximum outer diameter of first set of engagement barbs 586 is preferably at least as large as the maximum outer diameter of engagement bulb 582. Engagement bulb 582 and first set of engagement barbs 586 are separated by a substantially cylindrical second portion 588 of stem 574.

Positioned between first set of engagement barbs 586 and proximal end 576 of stem 574 is a second set of engagement barbs 590. Second set of engagement barbs 590 encircle and radially extend outward on exterior surface 580. Each one of second set of engagement barbs 590 have a maximum outer diameter that decreases in size towards distal end 578. Each one of second set of engagement barbs 590, however, has a maximum outer diameter larger than the maximum outer diameter of each one of first set of engagement barbs 586. First set of engagement barbs 586 and second set of engagement barbs 590 are separated by a substantially cylindrical third portion 592 of stem 574.

Figure 31:
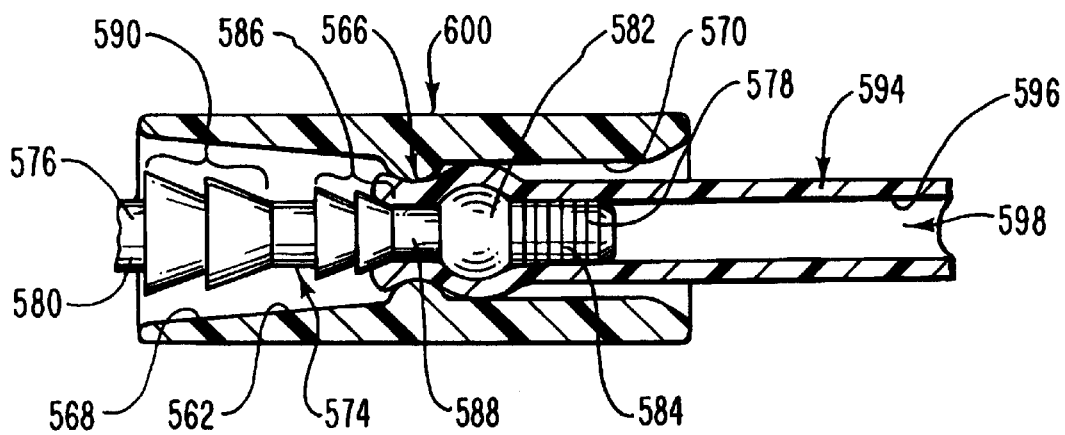
FIG. 31 is an elevation view in partial cross section of the stem in FIG. 30, a polyurethane catheter, and the corresponding fastening assembly of the catheter connection system of FIG. 20, all in an assembled condition.

Stem 574 is designed to receive and secure a silicone catheter, a polyurethane catheter, or a composite catheter. FIG. 31 shows stem 574 having a silicone catheter 594 secured thereto. Silicone catheter 594 is shown as comprising an interior surface 596 defining a lumen 598 extending therethrough. During attachment, stem 574 is advanced within lumen 598 of silicone catheter 594 until engagement bulb 582 and second portion 588 of stem 574 are received within lumen 598. Once stem 574 is properly received within lumen 598, a fourth fastening assembly 600 is advanced over silicone catheter 594 having stem 574 received therein.

Fourth fastening assembly 600 has substantially the same configuration and is identified by the same reference characters as fourth fastening assembly 555 shown in FIG. 27. The primary distinction is that fourth fastening assembly 600 is sized so that compression ring 566 can pass over engagement bulb 582 and compress silicone catheter 594 against second cylindrical portion 588 of stem 574, thereby producing a mechanical joinder and fluid tight coupling between silicone catheter 594 and stem 574.

In the preferred embodiment, as shown in FIG. 31, first portion 568 of interior surface 562 of fourth fastening assembly 600 is elongated so as to cover first set of engagement barbs 586 and second set of engagement barbs 590. Furthermore, second portion 570 of interior surface 562 has been elongated to cover engagement bulb 582 and first portion 584 of stem 574.

Figure 32:
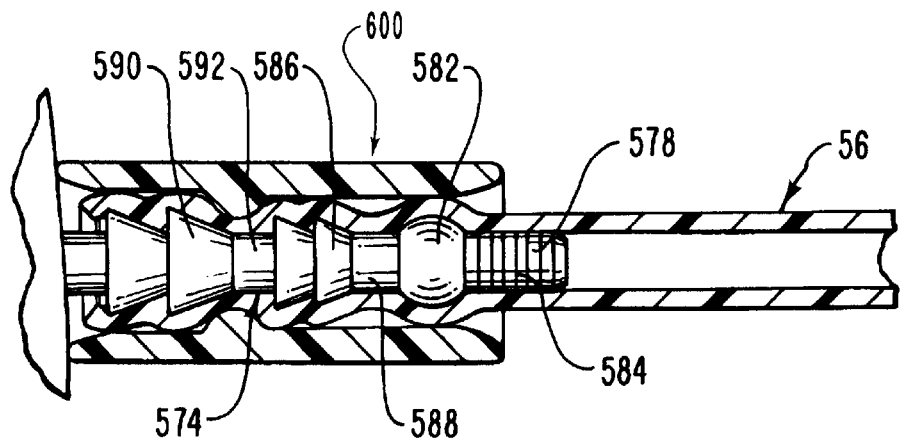
FIG. 32 is an elevation view in partial cross section of the stem of FIG. 30, a large silicone catheter, and the corresponding fastening assembly of the catheter connection system of FIG. 20, all in an assembled condition.

Finally, a silicone catheter or alternatively a composite catheter can also be secured to stem 574. First set of engagement barbs 586 and second set of engagement barbs 590 on stem 574 are comparable configured to first set of engagement barbs 538 and second set of engagement barbs 540, respectively, as shown in FIG. 28 on stem 530. Accordingly, polyurethane catheter 56, as shown in FIG. 32, can be secured to stem 574 using the same method as discussed with FIGS. 27 and 28. Using the same process, a composite catheter can also be secured to stem 574.

The above described catheter connection systems are provided as representative examples of preferred embodiments. The present invention envisions, however, a variety of equivalent embodiments which perform substantially the same function. By way of example and not by limitation, the various barb and bulb configurations on the exterior surfaces of individual stems can be varied in size, shape, and number. Furthermore, the barbs and bulbs can be interchanged on stems or cumulatively added to a single stem in order to allow attachment of a selected catheter chosen from a selected set of catheters.

In like manner, the various fastening assemblies can also be varied in size, shape, and configuration so as to correspond to the different barb and bulb configurations. It is also emphasized that alternative embodiments specifically discussed with regard to one type of catheter connection system are also relevant to the other catheter connection systems. Such alternatives include, but are not limited to, the structural configurations, material selections, and end uses of a catheter connection system. For example, as with other catheter connection systems, the catheter connections systems where one of three or more catheters can be secured to a stem can be made of metal or plastic. In addition, such systems can be used with an access port, leaflet port, catheter termination hub, or a catheter repair and extension assembly.

Figure 33:
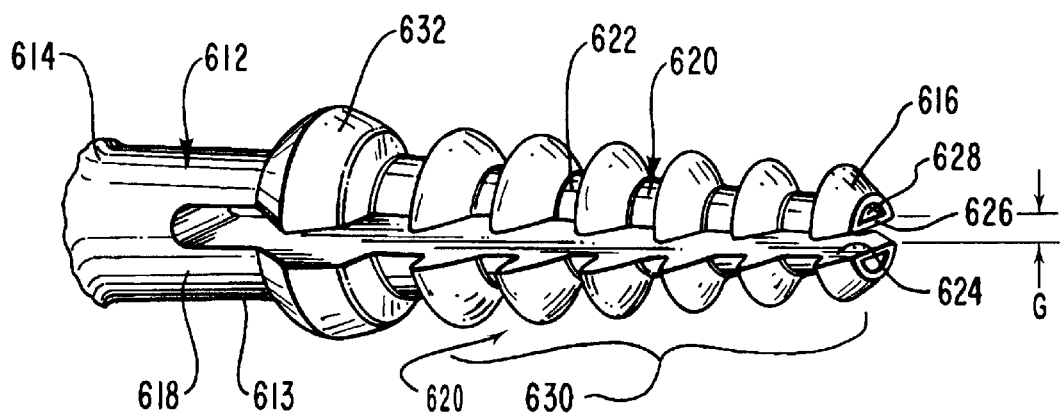
FIG. 33 is a perspective view of a stem used in a catheter connection system for attachment to one of three or more different kinds of dual lumen catheters.

In like manner, the alternative embodiments of the other catheter connection systems also relate to the catheter connection system where one of two dual lumen catheters can be secured to a stem. By way of example, FIG. 33 discloses stem 612 designed for attachment to a selected catheter chosen from three or more dual lumen catheters. Stem 612 is simply the combination of stem 342, shown in FIG. 18 and used for attachment to one of two dual lumen catheters, and stem 496, shown in FIG. 26, used for attachment to one of three or more single lumen catheters.

Stem 612 is shown as having an exterior surface 613 extending between a proximal end 614 and an opposing distal end 616. Stem 612 is further defined by a substantially cylindrical portion 618 positioned at proximal end 614. Extending distal of first portion 618 is a pair of adjacent prongs 620. Each of prongs 620 is defined by an exposed exterior surface 622 and an exposed inside face 624. Each exposed exterior surface is tapered so as to slope inward towards distal end 616. Each inside face 624 is adjacently facing and separated by a gap G. Each of prongs 620 are also defined as having an interior surface 626 that defines a passage 628 longitudinally extending through a respective prong 620 of stem 612.

The present invention also provides for gripping means on exposed exterior surface 622 on each of prongs 620. The gripping means is for engaging the interior surface of each of the lumens of the selected dual lumen catheter, as will be discussed below. This is accomplished when distal end 616 of each of prongs 620 is individually received in individual of the lumens of the selected dual lumen catheter. The gripping means also enables locking of the selected dual lumen catheter on stem 612.

By way of example and not by limitation, consecutively positioned at distal end 616 of each of prongs 620 are a plurality of engagement barbs 630.

Engagement barbs 630 span across and radially extend from exposed exterior surface 622. Each of engagement barbs 630 have a maximum outer radius that decreases in size towards distal end 616.

Positioned proximal of engagement barbs 630 on prongs 620 is a locking barb 632. Locking barb 632 also spans and radially extends from exposed exterior surface 622 of each of prongs 620. Locking barb 632 is defined as having a maximum outer radius that is larger than the maximum outer radius of engagement barbs 630. Engagement barbs 630 and locking barb 632 have substantially the same configuration and structural elements as engagement barbs 508 and locking barb 510 as previously discussed in FIG. 26.

The tapering of engagement barbs 630 enables the attachment of a variety of dual lumen polyurethane catheters having lumens of different sizes. The attachment of a polyurethane catheter is accomplished using second fastening assembly 56 in substantially the same manner as previously described in relation to FIGS. 25 and 26. The primary distinction is that the partition wall that separates the pair of lumens in the dual lumen polyurethane catheters must be received and compressed between opposing prongs 620 as was previously discussed in relation to FIG. 19. Stem 612 can also be used for attachment to a silicone catheter using first fastening assembly 52. This is accomplished in the same manner as described in relation to FIG. 19.

The present invention also provides for holding means operative when the distal end of each of prongs 620 is individually received in individual of the lumens of the selected dual lumen catheter. The holding means radially, inwardly compresses a portion of the body wall of the selected dual lumen catheter against a portion of the gripping means on each of prongs 620. The holding means also interacts with the gripping means to preclude unintentional disengagement of the selected catheter from stem 612. By way of example and not by limitation, the holding means includes second fastening assembly 56 discussed with FIGS. 25 and 26 and also first fastening assembly 52 as previously discussed with FIG. 19.

Figure 34:
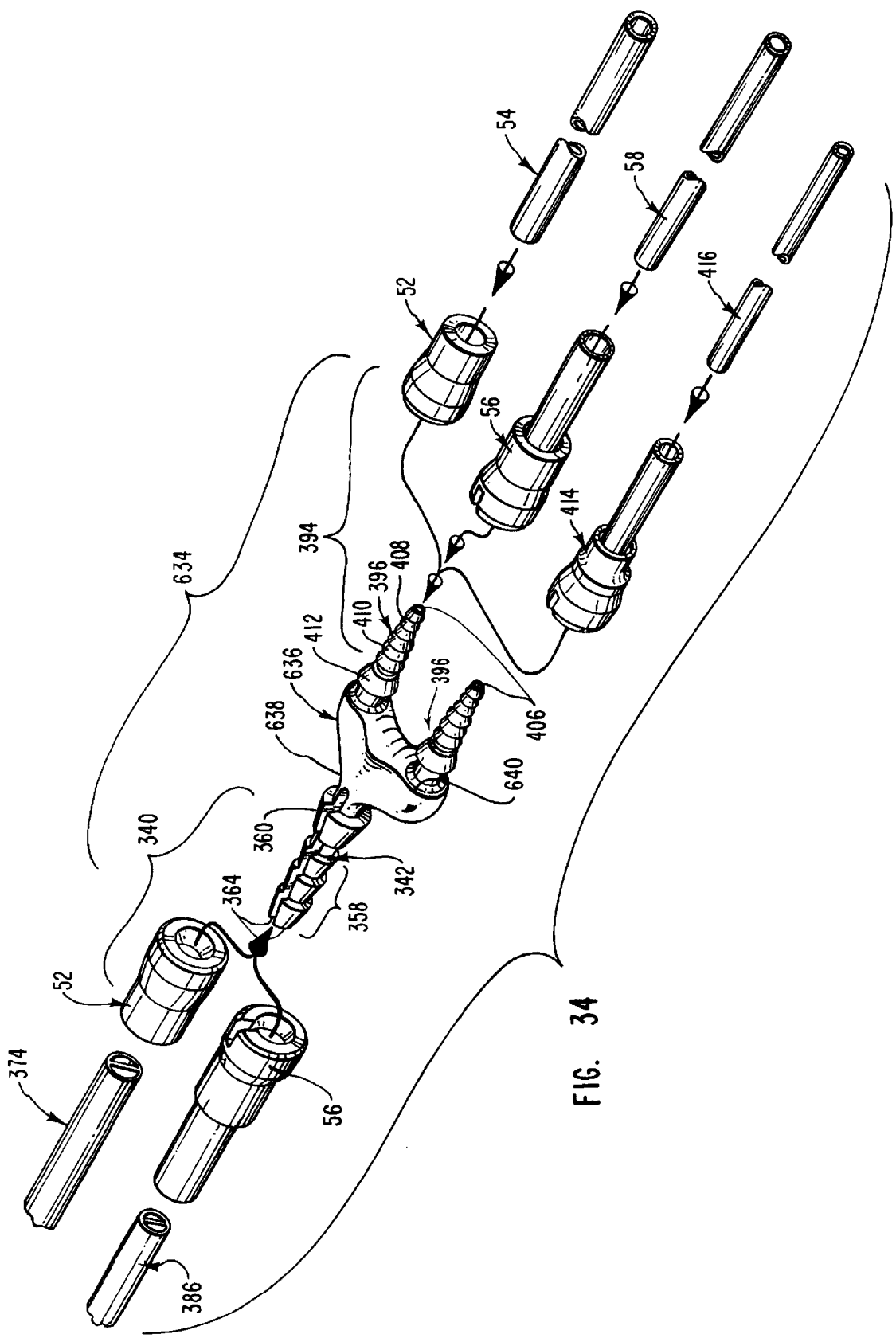
FIG. 34 is a perspective view of a system incorporating the catheter connection systems as shown in FIG. 17 and FIG. 20 for converting a single dual lumen catheter to a pair of single lumen catheters.

The present invention also envisions combining separate embodiments of the catheter connection systems to form alternative structures. By way of example, FIG. 34 discloses an catheter conversion system 634 used for converting a dual lumen catheter to two single lumen catheters. Conversion system 634 comprises an intercatheter adaptor 636 having a first end 638 and an opposing second end 640. Positioned at first end 638 is catheter connection system 340. As previously discussed with regard to FIGS. 17-18, catheter connection system 340 comprises stem 342 having engagement barbs 358 and locking barb 360 positioned thereon. One of two dual lumen catheters can be secured to stem 342. First fastening assembly 52 can be used for securing silicone catheter 374. Alternatively, second fastening 56 can be used for securing polyurethane catheter 386. These processes are previously discussed with regards to FIGS. 17–18.

Positioned at second end 640 is two sets of catheter connection systems 394. As previously discussed with FIG. 19, catheter connection system 394 comprises stem 396 having first set of engagement barbs 408, second set of engagement barbs 410, and locking barb 412 positioned thereon. One of three single lumen catheters can be secured to stem 396. First fastening assembly 52 can attach silicone catheter 54, second fastening assembly 56 can attach polyurethane catheter 58, or third fastening assembly 414 can attach polyurethane catheter 416. These processes are discussed in greater detail with regard to FIGS. 19–21.

Projecting from second end of intercatheter adaptor 636 are two adjacent stems 396. Each stem 396 has a passageway 406 extending through adaptor 636 and individually communicating with passages 364 in stem 342. Accordingly, by attaching one of two dual lumen catheters to stem 342 and one of the three single lumen catheters to each of stems 396, the conversion is made between a dual lumen catheter to two single lumen catheters.

The catheter connections systems disclosed in the present invention are designed to produce a mechanical joinder and a fluid tight coupling between the corresponding stem and catheter. As used in the specification and appended claims, the term "fluid tight coupling" means that there are substantially no fluid leaks between the stem and catheter. This holds true both when the fluid within the catheter is traveling under gravitational forces and when the fluid is inserted under a pressure.

It is envisioned that substantially no leaking will occur between a stem and a selected catheter when a fluid is pressurized within the selected catheter below 40 pounds per square inch, preferably below 60 pounds per square inch, and more preferably below 80 pounds per square inch. It is noted, however, that to enable a catheter connection system that will not leak under disclosed pressures, it is necessary that the selective catheter itself be able to withstand such pressures without failure.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter connection system for effecting a mechanical joinder between a medical device and a selected catheter chosen from among a first catheter, a second catheter, and a third catheter, the first catheter being made from a first material, the second catheter and the third catheter being made of a second material less pliant than the first material, and the inner diameter of the third catheter being smaller than the inner diameter of the second catheter, the selected catheter having a body wall with an exterior surface and with an interior surface defining a longitudinally extending, fluid flow lumen, said connection system comprising:

a. a rigid stem attached at a proximal end thereof to the medical device, said stem having a free distal end opposite said proximal end and an exterior surface extending therebetween;

b. anchoring means on said exterior surface of said stem for engaging the interior surface of the selected catheter when said distal end of said stem is received in the lumen of the selected catheter, and for enabling locking of the selected catheter on said stem; and c. clinching means operative when said distal end of said stem is received in the lumen of the selected catheter for radially, inwardly compressing the body wall of the selected catheter against a portion of said anchoring means, and for interacting with said anchoring means to preclude unintentional disengagement of the selected catheter from said stem, said clinching means comprising a set of fastening assemblies, individual of said fastening assemblies corresponding to the first catheter, the second catheter, and the third catheter, respectively.

2. A catheter connection system as recited in claim 1, wherein said anchoring means comprises:

(a) a first engagement barb radially, outwardly extending on said exterior surface of said stem and encircling said stem on said distal end of said stem, said first engagement barb having a maximum outer diameter so sized as to fit within the lumen of the selected catheter when said distal end of said stem is received in the lumen of the selected catheter;

(b) a second engagement barb radially, outwardly extending on said exterior surface of said stem and encircling said stem proximal of said first engagement barb, said second engagement barb having a maximum outer diameter larger than said first engagement barb; and (c) a locking barb radially, outwardly extending on said exterior surface of said stem and encircling said stem between said second engagement barb and the medical device, said locking barb having a maximum outer diameter that is larger than said maximum outer diameter of said second engagement barb.

3. A catheter connection system as recited in claim 1, wherein said anchoring means comprises:
(a) a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;
(b) a second set of engagement barbs radially, outwardly extending on said exterior surface of said stem and encircling said stem proximal of said first set of engagement barbs, said second set of engagement barbs having a maximum outer diameter larger than said first set of engagement barbs; and
(c) a locking barb radially, outwardly extending on said exterior surface of said stem and encircling said stem between said second set of engagement barbs and the medical device, said locking barb having a maximum outer diameter that is larger than said maximum outer diameter of said second set of engagement barbs.

4. A catheter connection system as recited in claim 3, wherein each consecutive one of said first set of engagement barbs and said second set of engagement barbs have a maximum outer diameter that decreases in size toward said distal end of said stem.

5. A catheter connection system as recited in claim 3, wherein said first set of engagement barbs and said second set of engagement barbs are adjacently disposed on said stem.

6. A catheter connection system as recited in claim 3, wherein said first set of engagement barbs and said second set of engagement barbs are separated by a portion of said stem.

7. A catheter connection system as recited in claim 3, further comprising a second locking barb radially, outwardly extending on said exterior surface of said stem and encircling said stem between said first set of engagement barbs and said second set of engagement barbs.

8. A catheter connection system as recited in claim 3, wherein said first set of engagement barbs comprises two or more engagement barbs that are substantially equally configured.

9. A catheter connection system as recited in claim 3, wherein said second set of engagement barbs comprises two or more engagement barbs that are substantially equally configured.

10. A catheter connection system as recited in claim 3, wherein said first set of engagement barbs comprises two or more engagement barbs, each consecutive one of said engagement barbs having a maximum outer diameter that decreases in size toward said distal end of said stem.

11. A catheter connection system as recited in claim 3, wherein said second set of engagement barbs comprises two or more engagement barbs, each consecutive one of said engagement barbs having a maximum outer diameter that decreases in size toward said distal end of said stem.

12. A catheter connection system as recited in claim 1, wherein said anchoring means comprises:
(a) a engagement bulb radially, outwardly extending on said exterior surface of said stem and encircling said stem at said distal end of said stem, said engagement bulb having a maximum outer diameter so sized as to fit within the lumen of the selected catheter when said distal end of said stem is received in the lumen of the selected catheter;
(b) a first set of engagement barbs radially, outwardly extending on said exterior surface of said stem proximal of said engagement bulb, said first set of engagement barbs having a maximum outer diameter at least as large as said maximum outer diameter of said engagement bulb and being separated from said engagement bulb by a first portion of said stem; and
(c) a second set of engagement barbs radially, outwardly extending on said exterior surface of said stem and encircling said stem proximal of said first set of engagement barbs, said second set of engagement barbs having a maximum outer diameter larger than said first set of engagement barbs and being separated from said first set of engagement barbs by a second portion of said stem.

13. A catheter connection system as recited in claim 1, wherein said stem and said anchoring means are made of metal.

14. A catheter connection system as recited in claim 1, wherein said stem and said anchoring means are made of plastic.

15. A catheter connection system as recited in claim 1, wherein said set of fastening assemblies comprises a first fastening assembly corresponding to the first catheter, said first fastening assembly comprising:
a. a first locking sleeve having a proximal end, a distal end, and an interior surface defining a passageway longitudinally extending through said first locking sleeve, said interior surface of said first locking sleeve radially, inwardly compressing the body wall of the first catheter against a portion of said anchoring means, when said distal end of said stem is received in the lumen of the first catheter and the first catheter with said distal end of said stem received therein is positioned within said passageway of said first locking sleeve; and
b. an annular compression ring extending inwardly from said interior surface of said first locking sleeve.

16. A catheter connection system as recited in claim 15, wherein said compression ring is positioned at said proximal end of said first locking sleeve.

17. A catheter connection system as recited in claim 15, wherein said compression ring is positioned between said proximal end and said distal end of said first locking sleeve.

18. A catheter connection system as recited in claim 15, wherein said set of fastening assemblies comprises a second fastening assembly corresponding to the second catheter, said second fastening assembly comprising:
a. a second locking sleeve having a distal end, a proximal end, and an interior surface defining a passageway extending therebetween;
b. a pliable first compression sleeve longitudinally disposed within said passageway of said second locking sleeve and having a distal end, a proximal end, and an interior surface defining a passageway longitudinally extending therethrough, said interior surface of said first compression sleeve radially, inwardly compressing the body wall of the selected catheter against a portion of said anchoring means, when said distal end of said stem is received in the lumen of the second catheter and the second catheter with said distal end of said stem received therein is positioned within said passageway of said first compression sleeve; and c. an opposing set of radially displaceable, resilient clamps at said proximal end of said second locking sleeve.

19. A catheter connection system as recited in claim 18, wherein said set of clamps comprises a pair of clamps.

20. A catheter connection system as recited in claim 18, wherein said set of clamps comprises a set of C-shaped clamps.

21. A catheter connection system as recited in claim 18, wherein said set of fastening assemblies comprises a third fastening assembly corresponding to the third catheter, said third fastening assembly comprising:

a. a third locking sleeve having a distal end, a proximal end, and an interior surface defining a passageway extending therebetween;

b. a pliable second compression sleeve longitudinally disposed within said passageway of said third locking sleeve and having a distal end, a proximal end, and an interior surface defining a passageway longitudinally extending therethrough, said second compression sleeve comprising:

i. a proximal portion at said proximal end of said second compression sleeve, said interior surface of said second compression sleeve at said proximal portion thereof being so sized and positioned as to encircle a proximal portion of said anchoring means, when said distal end of said stem is received within said passageway of said second compression sleeve; and ii. a distal portion at said distal end of said second compression sleeve, said distal portion of said second compression sleeve having an outer diameter smaller than the outer diameter of said proximal portion of said second compression sleeve, said interior surface of said second compression sleeve at said distal portion thereof inwardly compresses the body wall of the third catheter against a distal portion of said anchoring means, when said distal end of said stem is received in the lumen of the second catheter and the second catheter with said distal end of said stem received therein is positioned within said passageway of said second compression sleeve; and c. an opposing set of radially displaceable, resilient clamps at said proximal end of said third locking sleeve.

22. A catheter connection system as recited in claim 21, wherein said set of clamps comprises a pair of C-shaped clamps.

23. A catheter connection system as recited in claim 1, wherein the medical device is an implantable vascular access port.

24. A catheter connection system as recited in claim 23, wherein said access port includes a leaflet valve.

25. A catheter connection system as recited in claim 23, wherein said access port includes a needle-penetrable septum.

26. A catheter connection system as recited in claim 1, wherein the medical device is a catheter repair and extension assembly.

27. A catheter connection system as recited in claim 1, wherein the medical device is a catheter termination hub.

28. A catheter connection system as recited in claim 1, wherein the medical device is a medical tunneling instrument.

29. A catheter connection system for effecting a fluid tight coupling and a mechanical joinder between a medical device that accommodates for the flow of fluid therethrough in two distinct fluid flow pathways and a selected dual lumen catheter the selected dual lumen catheter having a body wall with an exterior surface and an interior surface, a catheter partition wall extends between spaced locations on the interior surface to define two distinct longitudinally extending, fluid flow lumens within the body wall, said connection system comprising:

a. a stem attached at a proximal end thereof in fluid communication to the medical device, said stem having a pair of adjacent prongs separated by a gap and each terminating at a free distal end, each of said prongs having an exposed exterior surface and an interior surface defining a passageway extending therethrough;

b. retaining means on said exposed exterior surface of each of said prongs for engaging the interior surface of each of the lumens of the selected dual lumen catheter, when said distal end of each of said prongs is individually received in individual of the lumens of the selected dual lumen catheter, and for enabling locking of the selected dual lumen catheter on said stem, said retaining means comprising:

i. an engagement barb spanning across and radially, outwardly extending on said exposed exterior surface of each of said prongs, said engagement barb having a maximum outer radius so sized as to fit within each of the lumens of the selected dual lumen catheter when said distal end of each of said prongs is individually received in individual of the lumens of the selected dual lumen catheter; and ii. a locking barb spanning across and radially, outwardly extending on said exposed exterior surface of each of said prongs between said engagement barb and the medical device, said locking barb having a maximum outer radius that is larger than said maximum outer radius of said engagement barb; and c. a fastening assembly comprising:

i. a locking sleeve having a distal end, a proximal end, and an interior surface defining a passageway extending therebetween;

ii. a pliable compression sleeve longitudinally disposed within said passageway of said locking sleeve and having a distal end, a proximal end, and an interior surface defining a passageway longitudinally extending therethrough, said interior surface of said compression sleeve radially inwardly compressing the body wall of the selected catheter said engagement barb on each of said prongs, when said distal end of each of said prongs is individually received in individual of the lumens of the selected dual lumen catheter and the selected dual lumen catheter with said distal end of each of said prongs of said stem received therein is positioned within said passageway of said compression sleeve; and iii. an opposing set of radially displaceable, resilient C-shaped clamps at said proximal end of said second locking sleeve, said set of clamps interacting with said retaining means to preclude unintentional disengagement of the selected catheter from said stem.

30. A catheter conversion system for effecting a fluid tight coupling and a mechanical joinder between a selected dual lumen catheter and two distinct selected single lumen catheters, the selected dual lumen catheter being chosen from among two or more dual lumen catheters each having a unique combination of size and material composition distinct from the others of the dual lumen catheters, the selected dual lumen catheter having a body wall with an exterior surface and an interior surface, the dual lumen catheter further having a partition wall extending between spaced locations on the interior surface to define two distinct longitudinally extending, fluid flow lumens within the body wall, each of the selected single lumen catheters being chosen from among two or more catheters each having a combination of size and material composition distinct from the other of the catheters, each of the selected single lumen catheters having a body wall with an exterior surface and with an interior surface defining a longitudinally extending, fluid flow lumen, said catheter conversion system comprising:

a. an adapter having a dual lumen coupling site, a first single lumen catheter coupling site, and a second single lumen catheter coupling site, b. a dual lumen catheter connection system at said dual lumen coupling site on said adapter, said dual lumen catheter connection system comprising:

i. a pronged stem attached to said adapter at said dual lumen coupling site, said pronged stem having a pair of adjacent prongs separated by a gap and each terminating at respective free distal ends, each of said prongs having an exposed exterior surface and an interior surface defining a passageway extending therethrough;

ii. an engagement barb spanning across and radially, outwardly extending on said exposed exterior surface of each of each said prongs, said engagement barb having a maximum outer radius so sized as to fit within each of the lumens of the selected dual lumen catheter, when said distal end of each of said prongs is individually received in individual of the lumens of the selected dual lumen catheter;

iii. a locking barb spanning across and radially, outwardly extending on said exposed exterior surface of each of said prongs between said engagement barb and said adapter, said locking barb having a maximum outer radius that is larger than said maximum outer radius of said engagement barb; and iv. holding means operative when said distal end of each of said prongs is individually received in individual of the lumens of the selected dual lumen catheter for radially inwardly compressing a portion of the body wall of the selected dual lumen catheter against said engagement barb on each of said prongs, and for interacting with said locking barb to preclude unintentional disengagement of the selected catheter from said pronged stem; and c. a first single lumen catheter connection system at said first single lumen coupling site on said adapter, said first single lumen catheter connection system being in fluid communication through said adapter with a first of said passageways through said prongs of said stem of said dual lumen catheter connection system, said first single lumen catheter connection system comprising:

i. a first tubular rigid stem attached at a proximal end thereof to said first single lumen coupling site on said adapter, said first tubular stem having a free distal end opposite said proximal end thereof, an exterior surface extending therebetween;

ii first anchoring means on said exterior surface of said first tubular stem for engaging the interior surface of a first of the selected single lumen catheters, when said distal end of said first tubular stem is received in the lumen of the first of the selected single lumen catheters, and for enabling locking of the first of the selected single lumen catheters on said first tubular stem; and iii. a first clinching means operative when said distal end of said first tubular stem is received in the lumen of the first of the selected single lumen catheters for radially inwardly compressing the body wall of the first of the selected single lumen catheters against a portion of said first anchoring means, and for interacting with said first anchoring means to preclude unintentional disengagement of the first of the selected single lumen catheter from said first tubular stem;

d. a second single lumen catheter connection systems at said second single lumen coupling site on said adapter, said second single lumen catheter connection system being in fluid communication through said adapter with a second of said passageways through said prongs of said stem of said dual lumen catheter connection system, said second single lumen catheter connection systems comprising:

i. a rigid second tubular stem attached at a proximal end thereof to said first single lumen coupling site on said adapter, said first tubular stem having a free distal end opposite said proximal end thereof, an exterior surface extending therebetween;

ii. second anchoring means on said exterior surface of said second tubular stem for engaging the interior surface of a second of the selected single lumen catheters, when said distal end of said second tubular stem is received in the lumen of the second of the selected single lumen catheters, and for enabling locking of the second of the selected single lumen catheters on said second tubular stem; and iii. second clinching means operative when said distal end of said second tubular stem is received in the lumen of the second of the selected single lumen catheters for radially inwardly compressing the body wall of the second of the selected single lumen catheter against a portion of said second anchoring means, and for interacting with said second anchoring means to preclude unintentional disengagement of the second of the selected single lumen catheters from said first tubular stem.

31. A catheter connection system for effecting a fluid tight coupling and a mechanical joinder between a medical device that accommodates a fluid flow and a selected catheter chosen from among a first catheter made of silicone and a second catheter, and a contrastingly sized third catheter both made of polyurethane, the selected catheter having a body wall with an exterior surface and with an interior surface defining a longitudinally extending, fluid flow lumen, said connection system comprising:

a. a rigid, tubular stem attached at a proximal end thereof in fluid communication to the medical device, said stem having a free distal end opposite said proximal end and an exterior surface extending therebetween;

b. anchoring means on said exterior surface of said stem for engaging the interior surface of the selected catheter when said distal end of said stem is received within the lumen of the selected catheter, and for enabling locking of the selected catheter on said stem, said anchoring means comprising:

i. a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;

ii. a second set of engagement barbs radially, outwardly extending on said exterior surface of said stem and encircling said stem proximal of said first set of engagement barbs, said second set of engagement barbs having a maximum outer diameter larger than said first set of engagement barbs; and iii. a locking barb radially, outwardly extending on said exterior surface of said stem and encircling said stem between said second set of engagement barbs and the medical device, said locking barb having a maximum outer diameter that is larger than said maximum outer diameter of said second set of engagement barbs; and c. clinching means operative when said distal end of said stem is received in the lumen of the selected catheter for radially, inwardly compressing a portion of the body wall of the selected catheter against a portion of said anchoring means, and for interacting with said anchoring means to preclude unintentional disengagement of the selected catheter from said stem.

32. A catheter connection system as recited in claim 31, wherein said first set of engagement barb and said second set of engagement barbs each comprise two or more engagement barbs.

33. A catheter connection system as recited in claim 31, wherein said first set of engagement barbs and said second set of engagement barbs are adjacently disposed.

34. A catheter connection system as recited in claim 31, wherein said locking barb further comprises:

(a) a proximal side wall encircling said stem and radially extending outward therefrom to an outside corner; and (b) a frustoconical top surface encircling said stem and extending from said first outside corner distally toward said stem.

35. A catheter connection system as recited in claim 34, wherein said proximal side wall extends from said exterior surface of said stem to said second outside corner at an angle greater than 90° as measured between said proximal side wall and the longitudinal axis of said stem proximal of said proximal side wall.

36. A catheter connection system as recited in claim 31, wherein said clinching means comprises a first fastening assembly corresponding to the first catheter, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the first catheter against a portion of said anchoring means, when said distal end of said stem is received in the lumen of the first catheter and the first catheter with said stem received therein is positioned within said passageway of said first locking sleeve; and b. an annular compression ring extending inwardly from said interior surface of said first locking sleeve.

37. A catheter connection system as recited in claim 36, wherein said annular compression ring is positioned at said proximal end of said first locking sleeve.

38. A catheter connection system as recited in claim 36, wherein said compression ring has an inner diameter larger than said maximum outer diameter of said locking barb.

39. A catheter connection system as recited in claim 31, wherein said stem comprises:

a. a distal portion, said first set of engagement barbs being positioned on said distal portion; and b. a proximal portion having an outer diameter larger than the outer diameter of said distal portion, said second set of engagement barbs being positioned on said proximal portion.

40. A catheter connection system as recited in claim 36, wherein said clinching means comprises a second fastening assembly corresponding to the second catheter, said second fastening assembly comprising:

a. a second locking sleeve having a distal end, a proximal end, and an interior surface defining a passageway extending therebetween;

b. a pliable first compression sleeve longitudinally disposed within said passageway of said second locking sleeve and having a distal end, a proximal end, and an interior surface defining a passageway longitudinally extending therethrough, said interior surface of said first compression sleeve radially, inwardly compressing a portion of the body wall of the second catheter against a portion of said anchoring means, when said stem is received in the lumen of the second catheter and the second catheter with said stem received therein is positioned within said passageway of said first compression sleeve; and c. an opposing set of radially displaceable, resilient C-shaped clamps at said proximal end of said second locking sleeve.

41. A catheter connection system as recited in claim 40, wherein said C-shaped clamps have an inner diameter slightly smaller than said maximum outer diameter of said locking barb.

42. A catheter connection system as recited in claim 40, wherein said clinching means comprises a third fastening assembly corresponding to the third catheter, said third fastening assembly comprising:

a. a third locking sleeve having a distal end, a proximal end, and an interior surface defining a passageway extending therebetween;

b. a pliable second compression sleeve longitudinally disposed within said passageway of said third locking sleeve and having a distal end, a proximal end, and an interior surface defining a passageway longitudinally extending therethrough, said second compression sleeve comprising:

i. a proximal portion at said proximal end of said second compression sleeve, said interior surface of said second compression sleeve at said proximal portion thereof being sized and positioned so as to encircle at least a portion of said second set of engagement barbs, when said distal end of said stem is received within said passageway of said second compression sleeve; and ii. a distal portion at said distal end of said second compression sleeve, said distal portion of said second compression sleeve having an outer diameter smaller than the outer diameter of said proximal portion of said second compression sleeve, said interior surface of said second compression sleeve at said distal portion thereof inwardly comprising the body wall of the third catheter against said first set of engagement barbs, when said distal end of said stem is received in the lumen of the third catheter and the third catheter with said distal end of said stem received therein is positioned within said passageway of said second compression sleeve; and c. an opposing set of radially displaceable, resilient C-shaped clamps at said proximal end of said third locking sleeve.

43. A catheter connection system for effecting a fluid tight coupling and a mechanical joinder between a medical device that accommodates a fluid flow and a selected catheter chosen from among three or more catheters, each of the catheters having a combination of size and material composition distinct from the other of the catheters, the selected catheter having a body wall with an exterior surface and with an interior surface defining a longitudinally extending, fluid flow lumen, said connection system comprising:

(a) a rigid, tubular stem attached at a proximal end thereof in fluid communication to the medical device, said stem having a free distal end opposite said proximal end and an exterior surface extending therebetween;

(b) anchoring means on said exterior surface of said stem for engaging the interior surface of the selected catheter when said distal end of said stem is received in the lumen of the selected catheter, and for enabling locking of the selected catheter on said stem, said anchoring means comprising:

(i) a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;

(ii) a second set of engagement barbs radially, outwardly extending on said exterior surface of said stem and encircling said stem proximal of said first set of engagement barbs, said second set of engagement barbs having a maximum outer diameter larger than said first set of engagement barbs;

(iii) a first locking barb radially, outwardly extending on said exterior surface of said stem and encircling said stem between said first set of engagement barbs and said second set of engagement barbs, said first locking barb having a maximum outer diameter larger than said maximum outer diameter of said first set of engagement barbs; and (iv) a second locking barb radially, outwardly extending on said exterior surface of said stem and encircling said stem between said second set of engagement barbs and the medical device, said second locking barb having a maximum outer diameter that is larger than said maximum outer diameter of said second set of engagement barbs; and (c) clinching means operative when said distal end of said stem is received in the lumen of the selected catheter for radially, inwardly compressing a portion of the body wall of the selected catheter against a portion of said anchoring means and for interacting with said anchoring means to preclude unintentional disengagement of the selected catheter from said stem.

44. A catheter connection system as recited in claim 43, wherein said first set of engagement barbs and said second set of engagement barbs each comprise two or more engagement barbs.

45. A catheter connection system as recited in claim 43, wherein said stem comprises:

a. a distal portion, said first set of engagement barbs being positioned on said distal portion; and b. a proximal portion having an outer diameter larger than the outer diameter of said distal portion, said second set of engagement barbs being positioned on said proximal portion.

46. A catheter connection system as recited in claim 43, wherein said second set of engagement barbs are separated from said first locking barb by an intermediate cylindrical portion of said stem.

47. A catheter connection system as recited in claim 43, wherein each of said first locking barbs and each of said second locking barbs further comprises:

(a) a proximal side wall encircling said stem and radially extending outward therefrom to an outside corner; and (b) a frustoconical top surface encircling said stem and extending from said first outside corner distally toward said stem.

48. A catheter connection system as recited in claim 47, wherein said proximal side wall extends from said exterior surface of said stem to said second outside corner at an angle greater than 90° as measured between said proximal side wall and the longitudinal axis of said stem proximal of said proximal side wall.

49. A catheter connection system as recited in claim 43, wherein said clinching means comprises a first fastening assembly, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said first locking sleeve; and b. an annular compression ring extending inwardly from said interior surface of said first locking sleeve.

50. A catheter connection system as recited in claim 49, wherein said compression ring is positioned at said proximal end of said first locking sleeve.

51. A catheter connection system as recited in claim 49, wherein said interior surface of said first locking sleeve is configured to radially, inwardly compress a portion of the body wall of the selected catheter against said first locking barb.

52. A catheter connection system as recited in claim 49, wherein said interior surface of said first locking sleeve is configured to radially, inwardly compress a portion of the body wall of the selected catheter against said second locking barb.

53. A catheter connection system as recited in claim 49, wherein said clinching means comprises a second fastening assembly, said second fastening assembly comprising:

a. a second locking sleeve having a distal end, a proximal end, and an interior surface defining a passageway extending therebetween;

b. a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the selected catheter against a portion of said anchoring means, when said distal end of said stem is received in the lumen of the selected catheter and the selected catheter with said stem received therein is positioned within said passageway of said compression sleeve; and c. an opposing set of radially displaceable, resilient C-shaped clamps positioned at said proximal end of said second locking sleeve.

54. A catheter connection system as recited in claim 53, wherein said interior surface of said compression sleeve is configured to radially, inwardly compressing a portion of the body wall of the selected catheter against said first set of engagement barbs.

55. A catheter connection system as recited in claim 53, wherein said interior surface of said compression sleeve is configured to radially, inwardly compress a portion of the body wall of the selected catheter against said second set of engagement barbs.

56. A catheter connection system for effecting a fluid tight coupling and a mechanical joinder between a medical device that accommodates a fluid flow and a selected catheter chosen from among three or more catheters, each of the catheters having a combination of size and material composition distinct from the other of the catheters, the selected catheter having a body wall with an exterior surface and with an interior surface defining a longitudinally extending, fluid flow lumen, said connection system comprising:

(a) a rigid, tubular stem attached at a proximal end thereof in fluid communication to the medical device, said stem having a free distal end opposite said proximal end and an exterior surface extending therebetween;

(b) anchoring means on said exterior surface of said stem for engaging the interior surface of the selected catheter when said distal end of said stem is received in the lumen of the selected catheter, and for enabling locking of the selected catheter on said stem, said anchoring means comprising:

(i) a plurality of engagement barbs radially, outwardly extending on said exterior surface of said stem and encircling said stem on said distal end of said stem, each consecutive one of said plurality of engagement barbs having a maximum outer diameter that decreases in size toward said distal end of said stem; and (ii) a locking barb radially, outwardly extending on said exterior surface of said stem and encircling said stem between said plurality of engagement barbs and the medical device, said locking barb having a maximum outer diameter that is larger than said maximum outer diameter of said plurality of engagement barbs; and (c) clinching means operative when said distal end of said stem is received in the lumen of the selected catheter for radially, inwardly compressing a portion of the body wall of the selected catheter against a portion of said anchoring means and for interacting with said anchoring means to preclude unintentional disengagement of the selected catheter from said stem.

57. A catheter connection system as recited in claim 56, wherein said plurality of engagement barbs comprises at least three engagement barbs.

58. A catheter connection system as recited in claim 56, wherein said plurality of engagement barbs comprises at least four engagement barbs.

59. A catheter connection system as recited in claim 56, wherein said locking barb further comprises:

(a) a proximal side wall encircling said stem and radially extending outward therefrom to an outside corner; and (b) a frustoconical top surface encircling said stem and extending from said first outside corner distally toward said stem.

60. A catheter connection system as recited in claim 59, wherein said proximal side wall extends from said exterior surface of said stem to said second outside corner at an angle greater than 90° as measured between said proximal side wall and the longitudinal axis of said stem proximal of said proximal side wall.

61. A catheter connection system as recited in claim 56, wherein said clinching means comprises a first fastening assembly, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said first locking sleeve; and b. an annular compression ring extending inwardly from said interior surface of said first locking sleeve.

62. A catheter connection system as recited in claim 61, wherein said compression ring is positioned at said proximal end of said first locking sleeve.

63. A catheter connection system as recited in claim 61, wherein said compression ring has an inner diameter slightly larger than said maximum outer diameter of said locking barb.

64. A catheter connection system as recited in claim 61, wherein said clinching means comprises a second fastening assembly, said second fastening assembly comprising:

a. a second locking sleeve having a distal end, a proximal end, and an interior surface defining a passageway extending therebetween;

b. a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said compression sleeve; and c. an opposing set of radially displaceable, resilient C-shaped clamps at said proximal end of said second locking sleeve.

65. A catheter connection system as recited in claim 64, wherein said C-shaped clamps have an inner diameter slightly smaller than said maximum outer diameter of said locking barb.

66. A catheter connection system for effecting a fluid tight coupling and a mechanical joinder between a medical device that accommodates a fluid flow and a selected catheter chosen from among three or more catheters, each of the catheters having a combination of size and material composition distinct from the other of the catheters the selected catheter having a body wall with an exterior surface and with an interior surface defining a longitudinally extending, fluid flow lumen, said connection system comprising:

(a) a rigid, tubular stem attached at a proximal end thereof in fluid communication to the medical device, said stem having a free distal end opposite said proximal end and an exterior surface extending therebetween;

(b) anchoring means on said exterior surface of said stem for engaging the interior surface of the selected catheter when said distal end of said stem is received in the lumen of the selected catheter, and for enabling locking of the selected catheter on said stem, said anchoring means comprising:

(i) a first set of engagement barbs radially, outwardly extending on said exterior surface of said stem and encircling said stem on said distal end of said stem, each one of said first set of engagement barbs having a maximum outer diameter that decreases in size towards said distal end of said stem;

(ii) a second set of engagement barbs radially, outwardly extending on said exterior surface of said stem and encircling said stem proximal of said first set of engagement barbs, each one of said second set of engagement barbs having a maximum outer diameter that decreases in size towards said distal end of said stem, each one of said second set of engagement barbs having a maximum outer diameter larger than said maximum outer diameter of each of said first set of engagement barbs, said first set of engagement barbs and said second set of engagement barbs being separated by a portion of said stem; and (iii) a locking barb radially, outwardly extending on said exterior surface of said stem and encircling said stem between said second set of engagement barbs and the medical device, said locking barb having a maximum outer diameter that is larger than said maximum outer diameter of each of said second set of engagement barbs; and (c) clinching means operative when said distal end of said stem is received in the lumen of the selected catheter for radially, inwardly compressing a portion of the body wall of the selected catheter against a portion of said anchoring means and for interacting with said anchoring means to preclude unintentional disengagement of the selected catheter from said stem.

67. A catheter connection system as recited in claim 66, wherein said first set of engagement barbs and said second set of engagement barbs each comprise two or more engagement barbs.

68. A catheter connection system as recited in claim 66, wherein said clinching means comprises a first fastening assembly, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said first locking sleeve; and b. an annular compression ring extending inwardly from said interior surface of said first locking sleeve.

69. A catheter connection system as recited in claim 68, wherein said compression ring is positioned at said proximal end of said first locking sleeve.

70. A catheter connection system as recited in claim 68, wherein said compression ring is positioned between said proximal end and said distal end of said first locking sleeve.

71. A catheter connection system as recited in claim 68, wherein said clinching means comprises a second fastening assembly, said second fastening assembly comprising:

a. a second locking sleeve having a distal end, a proximal end, and an interior surface defining a passageway extending therebetween;

b. a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said compression sleeve; and c. an opposing set of radially displaceable, resilient C-shaped clamps positioned at said proximal end of said second locking sleeve.

72. A catheter connection system as recited in claim 71, wherein said C-shaped clamps have an inner diameter slightly smaller than said maximum outer diameter of said locking barb.

73. A catheter connection system for effecting a fluid tight coupling and a mechanical joinder between a medical device that accommodates a fluid flow and a selected catheter chosen from among three or more catheters, each of the catheters having a combination of size and material composition distinct from the others of the catheters, the selected catheter having a body wall with an exterior surface and with an interior surface defining a longitudinally extending, fluid flow lumen, said connection system comprising:

a. a rigid, tubular stem attached at a proximal end thereof in fluid communication to the medical device, said stem having a free distal end opposite said proximal end and an exterior surface extending therebetween;

b. anchoring means on said exterior surface of said stem for engaging the interior surface of the selected catheter when said distal end of said stem is received in the lumen of the selected catheter, and for enabling locking of the selected catheter on said stem, said anchoring means comprising:

i. a engagement bulb radially, outwardly extending on said exterior surface of said stem and encircling said stem at said distal end of said stem, said engagement bulb having a maximum outer diameter so sized as to fit within the lumen of the selected catheter when said distal end of said stem is received in the lumen of the selected catheter;

ii. a first set of engagement barbs radially, outwardly extending on said exterior surface of said stem proximal of said engagement bulb, said first set of engagement barbs having a maximum outer diameter larger than said maximum outer diameter of said engagement bulb, said first set of engagement barbs being separated from said engagement bulb by a first intermediate cylindrical portion of said stem; and iii. a second set of engagement barbs radially, outwardly extending on said exterior surface of said stem and encircling said stem proximal of said first set of engagement barbs, said second set of engagement barbs having a maximum outer diameter larger than said first set of engagement barbs and being separated from said first set of engagement barbs by a second intermediate cylindrical portion of said stem; and c. clinching means operative when said distal end of said stem is received in the lumen of the selected catheter for radially, inwardly compressing a portion of the body wall of the selected catheter against a portion of said anchoring means, and for interacting with said anchoring means to preclude unintentional disengagement of the selected catheter from said stem.

74. A catheter connection system as recited in claim 73, wherein each one of said first set of engagement barbs and said second set of engagement barbs have a maximum outer diameter that decreases toward said distal end of said stem.

75. A catheter connection system as recited in claim 73, wherein said first set of engagement barbs and said second set of engagement barbs each comprise two or more engagement barbs.

76. A catheter connection system as recited in claim 73, wherein a distal cylindrical portion of said stem projects distal of said engagement bulb.

77. A catheter connection system as recited in claim 73, wherein said clinching means comprises a first fastening assembly, said first fastening assembly comprising:
   a. a first locking sleeve having a proximal end, a distal end, and an interior surface defining a passageway longitudinally extending through said first locking sleeve, said interior surface of said first locking sleeve radially, inwardly compressing a portion of the body wall of the selected catheter against a portion of said anchoring means, when said distal end of said stem is received in the lumen of the selected catheter and the selected catheter with said distal end of said stem received therein is positioned within said passageway of said first locking sleeve; and
   b. an annular compression ring extending inwardly from said interior surface of said first locking sleeve.

78. A catheter connection system as recited in claim 77, wherein said compression ring is so positioned on said interior surface of said first locking sleeve as to compress a portion of the body wall of the selected catheter against said first intermediate cylindrical portion of said stem, when said distal end of said stem is received in the lumen of the selected catheter and the selected catheter with said distal end of said stem received therein is positioned within said passageway of said first locking sleeve.

79. A catheter connection system as recited in claim 77, wherein said compression ring is so positioned on said interior surface of said first locking sleeve as to compress a portion of the body wall of the selected catheter against said second intermediate cylindrical portion of said stem, when said distal end of said stem is received in the lumen of the selected catheter and the selected catheter with said distal end of said stem received therein is positioned within said passageway of said first locking sleeve.

80. A catheter connection system for effecting a mechanical joinder between a medical device and a selected catheter, the selected catheter having a body wall with an exterior surface and with an interior surface defining a longitudinally extending, fluid flow lumen, said connection system comprising:
   a. a rigid stem attached at a proximal end thereof to the medical device, said stem having a free distal end opposite said proximal end and an exterior surface extending therebetween;
   b. anchoring means on said exterior surface of said stem for engaging the interior surface of the selected catheter when said distal end of said stem is received in the lumen of the selected catheter, and for enabling locking of the selected catheter on said stem; and
   c. a fastening assembly comprising:
      i. a locking sleeve having a distal end, a proximal end, and an interior surface defining a passageway extending therebetween;
      ii. a pliable compression sleeve longitudinally disposed within said passageway of said locking sleeve and having a distal end, a proximal end, and an interior surface defining a passageway longitudinally extending therethrough, said interior surface of said compression sleeve radially, inwardly compressing the body wall of the selected catheter against a portion of said anchoring means, when said distal end of said stem is received in the lumen of the selected catheter and the selected catheter with said distal end of said stem received therein is positioned within said passageway of said compression sleeve; and
      iii. an opposing set of radially displaceable, resilient C-shaped clamps positioned at said proximal end of said locking sleeve, said set of clamps interacting with said anchoring means to preclude unintentional disengagement of the selected catheter from said stem.

81. A catheter connection system as recited in claim 80, wherein said anchoring means comprises:
   a. a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;
   b. a second set of engagement barbs radially, outwardly extending on said exterior surface of said stem and encircling said stem proximal of said first set of engagement barbs, said second set of engagement barbs having a maximum outer diameter larger than said first set of engagement barbs; and
   c. a locking barb radially, outwardly extending on said exterior surface of said stem and encircling said stem between said second set of engagement barbs and the medical device, said locking barb having a maximum outer diameter that is larger than said maximum outer diameter of said second set of engagement barbs.

82. A catheter connection system as recited in claim 81, wherein said anchoring means comprises:
   a. a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;
   b. a second set of engagement barbs radially, outwardly extending on said exterior surface of said stem and encircling said stem proximal of said first set of engagement barbs, said second set of engagement barbs having a maximum outer diameter larger than said first set of engagement barbs;
   c. a first locking barb radially, outwardly extending on said exterior surface of said stem and encircling said stem between said first set of engagement barbs and said second set of engagement barbs, said first locking barb having a maximum outer diameter larger than said maximum outer diameter of said first set of engagement barbs; and
   d. a second locking barb radially, outwardly extending on said exterior surface of said stem and encircling said stem between said second set of engagement barbs and the medical device, said second locking barb having a maximum outer diameter that is larger than said maximum outer diameter of said second set of engagement barbs.

83. A catheter connection system as recited in claim 81, wherein each of said second set of engagement barbs has a maximum outer diameter that decreases in size towards said distal end of said stem, and said first set of engagement barbs and said second set of engagement barbs are separated by an intermediate cylindrical portion of said stem.

84. A catheter connection system as recited in claim 80, wherein said anchoring means comprises:
   a. a plurality of engagement barbs radially, outwardly extending on said exterior surface of said stem and encircling said stem on said distal end of said stem, each consecutive one of said plurality of engagement barbs having a maximum outer diameter that decreases in size toward said distal end of said stem; and
   b. a locking barb radially, outwardly extending on said exterior surface of said stem and encircling said stem between said plurality of engagement barbs and the medical device, said locking barb having a maximum outer diameter that is larger than said maximum outer diameter of said plurality of engagement barbs.

85. A catheter connection system for effecting a fluid tight coupling and a mechanical joinder between a medical device that accommodates for the flow of fluid therethrough in two distinct fluid flow pathways and a selected dual lumen catheter chosen from either a first dual lumen catheter or a second dual lumen catheter, the first dual lumen catheter being made from a first material and the second dual lumen catheter being made from a second material, the second material being less pliant than the first material, the selected dual lumen catheter having a body wall with an exterior surface and an interior surface, a catheter partition wall extends between spaced locations on the interior surface to define two distinct longitudinally extending, fluid flow lumens within the body wall, said connection system comprising:
   (a) a stem attached at a proximal end thereof in fluid communication to the medical device, said stem having a pair of adjacent prongs separated by a gap and each terminating at a free distal end, each of said prongs having an exposed exterior surface and an interior surface defining a passageway extending therethrough;
   (b) retaining means on said exposed exterior surface of each of said prongs for engaging the interior surface of each of the lumens of the selected dual lumen catheter when said distal end of each of said prongs is individually received in individual of the lumens of the selected dual lumen catheter, and for enabling locking of the selected dual lumen catheter on said stem, said retaining means comprising:
      (i) an engagement barb spanning across and radially, outwardly extending on said exposed exterior surface of each of said prongs, said engagement barb having a maximum outer radius so sized as to fit within each of the lumens of the selected dual lumen catheter when said distal end of each of said prongs is individually received in individual of the lumens of the selected dual lumen catheter; and
      (ii) a locking barb spanning across and radially, outwardly extending on said exposed exterior surface of each of said prongs between said engagement barb and the medical device, said locking barb having a maximum outer radius that is larger than said maximum outer radius of said engagement barb; and
   (c) clasping means operative when said distal end of each of said prongs is individually received in individual of the lumens of the selected dual lumen catheter for radially, inwardly compressing a portion of the body wall of the selected dual lumen catheter against a portion of said retaining means on each of said prongs, and for interacting with said retaining means to preclude unintentional disengagement of the selected catheter from said stem.

86. A catheter connection system as recited in claim 85, wherein said retaining means further comprises a plurality of engagement barbs radially, outwardly extending on said exposed exterior surface of each of said prongs.

87. A catheter connection system as recited in claim 85, wherein said locking barb further comprises:
   (a) a distal side wall radially extending outward from said exposed outside surface to a first outside corner having an outer radius;
   (b) a proximal side wall radially extending outward from said exposed outside surface to a second outside corner having an outer radius larger than said outer radius of said first outside corner; and
   (c) a top surface spanning across said exposed outside surface of each of said prongs and extending between said first outside corner and said second outside corner.

88. A catheter connection system as recited in claim 87, wherein said proximal side wall extends from said exterior surface of said stem to said second outside corner at an angle greater than 90° as measured between said proximal side wall and the longitudinal axis of said stem proximal of said proximal side wall.

89. A catheter connection system as recited in claim 85, wherein said clasping means comprises a first fastening assembly, said first fastening assembly comprising:
   a. a first locking sleeve having a proximal end, a distal end, and an interior surface defining a passageway longitudinally extending through said first locking sleeve, said interior surface of said first locking sleeve radially, inwardly compressing a portion of the body wall of the selected catheter against a portion of said retaining means, when said distal end of each of said prongs is individually received in individual of the lumens of the selected dual lumen catheter and the selected dual lumen catheter with said distal end of each of said prongs of said stem received therein is positioned within said passageway of said first locking sleeve; and
   b. an annular compression rings extending inwardly from said interior surface of said first locking sleeve.

90. A catheter connection system as recited in claim 89, wherein said compression ring has an inner radius larger than said maximum outer radius of each of said locking barb.

91. A catheter connection system as recited in claim 89, wherein said compression ring is positioned at said proximal end of said first locking sleeve.

92. A catheter connection system as recited in claim 89, wherein said interior surface of said first locking sleeve radially, inwardly compresses a portion of the body wall of the selected catheter against each of said prongs and urges said prongs toward each other thereby to compress at least a portion of the partition wall of the selected catheter between said prongs.

93. A catheter connection system as recited in claim 89, wherein said clasping means comprises a second fastening assembly, said second fastening assembly comprising:
   a. a second locking sleeve having a distal end, a proximal end, and an interior surface defining a passageway extending therebetween;

b. a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing a portion of the body wall of the selected catheter against a portion of said retaining means, when said distal end of each of said prongs is individually received in individual of the lumens of the selected dual lumen catheter and the selected dual lumen catheter with said distal end of each of said prongs of said stem received therein is positioned within said passageway of said compression sleeve; and c. an opposing set of radially displaceable, resilient C-shaped clamps at said proximal end of said second locking sleeve.

94. A catheter connection system as recited in claim 93, wherein said interior surface of said compression sleeve radially, inwardly compresses the body wall of the selected catheter against each of said adjacent prongs and urges said prongs toward each other, thereby to compress at least a portion of the partition wall between said prongs.

95. A catheter connection system for effecting a fluid tight coupling and a mechanical joinder between a medical device that accommodates for the flow of fluid therethrough in two distinct fluid flow pathways and a selected dual lumen catheter chosen from among a first dual lumen catheter, a second dual lumen catheter, and a third dual lumen catheter, the first dual lumen catheter being made from a first material, the second dual lumen catheter and the third dual lumen catheter being made of a second material less pliant than the first material, and the inner diameter of the third dual lumen catheter being less than the inner diameter of the second dual lumen catheter, the selected dual lumen catheter having a body wall with an exterior surface and an interior surface, the selected dual lumen catheter further having a partition wall extending between spaced locations or the interior surface to define two distinct longitudinally extending, fluid flow lumens within the body wall, said connection system comprising:

a. a stem attached at a proximal end thereof in fluid communication to the medical device, said stem having a pair of adjacent prongs separated by a gap and each terminating at a free distal end, each of said prongs having an exposed exterior surface and an interior surface defining a passageway extending therethrough;

b. gripping means on said exposed exterior surface of each of said prongs for engaging the interior surface of each of the lumens of the selected dual lumen catheter when said distal end of each of said prongs is individually received in individual of the lumens of the selected dual lumen catheter, and for enabling locking of the selected dual lumen catheter on said stem, said gripping means comprising:

i. an engagement barb spanning across and radially, outwardly extending on said exposed exterior surface of each of said prongs, said engagement barb having a maximum outer radius so sized as to fit within each of the lumens of the selected dual lumen catheter when said distal end of each of said prongs is individually received in individual of the lumens of the selected dual lumen catheter; and ii. a locking barb spanning across and radially, outwardly extending on said exposed exterior surface of each of said prongs between said engagement barb and the medical device, said locking barb having a maximum outer radius that is larger than said maximum outer radius of said engagement barb; and c. holding means operative when said distal end of each of said prongs is individually received in individual of the lumens of the selected dual lumen catheter for radially, inwardly compressing a portion of the body wall of the selected dual lumen catheter against said engagement barb on each of said prongs, and for interacting with said locking barb to preclude unintentional disengagement of the selected catheter from said stem, said holding means comprising a set of fastening assemblies, individual of said fastening assemblies corresponding to the first dual lumen catheter, the second dual lumen catheter, and the third dual lumen catheter, respectively.

96. A catheter connection system as recited in claim 95, wherein said gripping means further comprises a plurality of said engagement barbs spanning across and radially, outwardly extending on said exposed exterior surface of each of said prongs, said engagement barbs each having a maximum outer radius that decreases in size toward said distal end of said stem, said maximum outer radius of each of said engagement barbs being less than said maximum outer radius of said locking barb.

97. A catheter connection system as recited in claim 95, wherein said set of fastening assemblies comprises a first fastening assembly corresponding to said first dual lumen catheter, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the first dual lumen catheter against said engagement barb on each of said prongs of said stem, when said distal end of each of said prongs is individually received in individual of the lumens of the first dual lumen catheter and the first dual lumen catheter with said distal end of each of said prongs of said stem received therein is positioned within said passageway of said first locking sleeve; and b. an annular compression ring extending inwardly from said interior surface of said first locking sleeve.

98. A catheter connection system as recited in claim 97, wherein said compression ring has an inner radius larger than said maximum outer radius of each of said locking barb.

99. A catheter connection system as recited in claim 97, wherein said compression ring is positioned at said proximal end of said first locking sleeve.

100. A catheter connection system as recited in claim 97, wherein said interior surface of said first locking sleeve radially, inwardly compresses a portion of the body wall of the first dual lumen catheter against each of said prongs and urges said prongs toward each other, thereby to compress at least a portion of the partition wall of the first dual lumen catheter between said prongs.

101. A catheter connection system as recited in claim 95, wherein said set of fastening assemblies comprises a second fastening assembly corresponding to the second dual lumen catheter, said second fastening assembly comprising:

a. a second locking sleeve having a distal end, a proximal end, and an interior surface defining a passageway extending therebetween;

b. a pliable first compression sleeve longitudinally disposed within said passageway of said second locking sleeve and having a distal end, a proximal end, and an interior surface defining a passageway longitudinally extending therethrough, said interior surface of said compression sleeve radially, inwardly compressing the body wall of the second dual lumen catheter against said engagement barb on each of said prongs of said stem, when said distal end of each of said prongs is individually received in individual of the lumens of the second dual lumen catheter and the second dual lumen catheter with said distal ends of each of said prongs of said stem received therein is positioned within said passageway of said compression sleeve; and c. an opposing set of radially displaceable, resilient clamps at said proximal end of said second locking sleeve.

102. A catheter connection system as recited in claim 101, wherein said interior surface of said compression sleeve radially, inwardly compresses a portion of the body wall of the second dual lumen catheter against each of said prongs and urges said prongs toward each other, thereby to compress at least a portion of the partition wall of the second dual lumen catheter between said prongs.

103. A catheter connection system as defined in claim 101, wherein said set of clamps comprises a pair of C-shaped clamps.

104. A catheter connection system as recited in claim 101, wherein said set of fastening assemblies comprises a third fastening assembly corresponding to the third dual lumen catheter, said third fastening assembly comprising:

a. a third locking sleeve having a distal end, a proximal end, and an interior surface defining a passageway extending therebetween;

b. a pliable second compression sleeve longitudinally disposed within said passageway of said third locking sleeve and having a distal end, a proximal end, and an interior surface defining a passageway longitudinally extending therethrough, said second compression sleeve comprising:

i. a proximal portion at said proximal end of said second compression sleeve, said interior surface of said second compression sleeve at said proximal portion thereof being sized and positioned so as to encircle at least a portion of said second set of engagement barbs, when said distal end of each of said prongs is individually received in individual of the lumens of the third dual lumen catheter and the third dual lumen catheter with said distal ends of each of said prongs of said stem received therein is positioned in said passageway of said second compression sleeve; and ii. a distal portion at said distal end of said second compression sleeve, said distal portion of said second compression sleeve having an outer diameter smaller than the outer diameter of said proximal portion, said distal portion of said second compression sleeve inwardly comprising the body wall of the third catheter against said engagement barb on each of said prongs, when said distal end of each of said prongs is individually received in individual of the lumens of the third dual lumen catheter and the third dual lumen catheter with said distal ends of each of said prongs of said stem received therein is positioned within said passageway of said second compression sleeve; and c. an opposing set of radially displaceable, resilient C-shaped clamps at said proximal end of said third locking sleeve.

105. A catheter conversion system for effecting a fluid tight coupling and a mechanical joinder between a selected dual lumen catheter and two distinct selected single lumen catheters, the selected dual lumen catheter being chosen from among two or more dual lumen catheters each having a unique combination of size and material composition distinct from the others of the dual lumen catheters, the selected dual lumen catheter having a body wall with an exterior surface and an interior surface, the selected dual lumen catheter further having a partition wall extending between spaced locations on the interior surface to define two distinct longitudinally extending, fluid flow lumens within the body wall, each of the selected single lumen catheters being chosen from among two or more catheters each having a combination of size and material composition distinct from the other of the catheters, each of the selected single lumen catheters having a body wall with an exterior surface and with an interior surface defining a longitudinally extending, fluid flow lumen, said catheter conversion system comprising:

a. an adapter having a first end and an opposing second end;

b. a dual lumen catheter connection system at said first end of said adapter, said dual lumen catheter connection system comprising:

i. a pronged stem attached at said first end in fluid communication with said adapter, said pronged stem having a pair of adjacent prongs separated by a gap and terminating at respective free distal ends, each of said prongs having an exposed exterior surface and an interior surface defining a passageway extending therethrough;

ii. an engagement barb spanning across and radially, outwardly extending on said exposed exterior surface of each of each said prongs, said engagement barb having a maximum outer radius so sized as to fit within each of the lumens of the selected dual lumen catheter when said distal end of each of said prongs is individually received in individual of the lumens of the selected dual lumen catheter;

iii. a locking barb spanning across and radially, outwardly extending on said exposed exterior surface of each of said prongs between said engagement barb and said adapter, said locking barb having a maximum outer radius that is larger than said maximum outer radius of said engagement barb; and iv. holding means operative when said distal end of each of said prongs is individually received in individual of the lumens of the selected dual lumen catheter for radially, inwardly compressing a portion of the body wall of the selected dual lumen catheter against said engagement barb on each of said prongs, and for interacting with said locking barb to preclude unintentional disengagement of the selected catheter from said stem; and c. a pair of single lumen catheter connection systems positioned at said second end of said adapter, individual of said single lumen catheter connection systems being in fluid communication through said adapter with a respective one of said passageways of said dual lumen catheter connection system, each of said single lumen catheter connection systems comprising:

i a rigid, tubular stem attached at a proximal end thereof to said second end of said adapter, said tubular stem having a free distal end opposite said proximal end thereof and an exterior surface extending therebetween;

ii. anchoring means on said exterior surface of said tubular stem for engaging the interior surface of the selected single lumen catheter, when said distal end of said tubular stem is received in the lumen of the selected single lumen catheter, and for enabling locking of the selected single lumen catheter on said tubular stem; and iii clinching means operative when said distal end of said tubular stem is received in the lumen of the selected single lumen catheter for radially, inwardly compressing a portion of the body wall of the selected single lumen catheter against a portion of said anchoring means and for interacting with said anchoring means to preclude unintentional disengagement of the selected single lumen catheter from said tubular stem.

106. A catheter connection system as recited in claim 105, further comprising a plurality of engagement barbs spanning across and radially, outwardly extending on said exposed exterior surface of each of said prongs, said engagement barbs each having a maximum outer radius that decreases in size toward said distal end of said stem, said maximum outer radius of each of said engagement barbs being less than said maximum outer radius of said locking barb.

107. A catheter connection system as defined in claim 105, wherein said holding means comprises a first fastening assembly, said first fastening assembly comprising:

a. a first locking sleeve having a proximal end, a distal end, and an interior surface defining a passageway longitudinally extending through said first locking sleeve, said interior surface of said first locking sleeve radially, inwardly compressing the body wall of the selected dual lumen catheter against said engagement barb on each of said prongs of said stem, when said distal end of each of said prongs is individually received in individual of the lumens of the selected dual lumen catheter and the selected dual lumen catheter with said distal ends of each of said prongs of said pronged stem received therein is positioned within said passageway of said first locking sleeve; and b. an annular compression ring extending inwardly from said interior surface of said first locking sleeve.

108. A catheter connection system as recited in claim 107, wherein said compression ring has an inner radius larger than said maximum outer radius of said locking barb.

109. A catheter connection system as recited in claim 107, wherein said compression ring is positioned at said proximal end of said first locking sleeve.

110. A catheter connection system as recited in claim 107, wherein said interior surface of said first locking sleeve radially, inwardly compresses the body wall of the selected dual lumen catheter against each of said prongs and urges said prongs toward each other, thereby to compress the partition wall of the selected catheter between said prongs.

111. A catheter connection system as recited in claim 107, wherein said holding means comprises a second fastening assembly, said second fastening assembly comprising:

a. a second locking sleeve having a distal end, a proximal end, and an interior surface defining a passageway extending therebetween;

b. a pliable compression sleeve longitudinally disposed within said passageway of said second locking sleeve and having a distal end, a proximal end, and an interior surface defining a passageway longitudinally extending therethrough, said interior surface of said compression sleeve radially, inwardly compressing the body wall of the selected dual lumen catheter against said engagement barb on each of said prongs of said stem, when said distal end of each of said prongs is individually received in individual of the lumens of the selected dual lumen catheter and the selected dual lumen catheter with said distal ends of each of said prongs of said stem received therein is positioned within said passageway of said compression sleeve; and c. an opposing set of radially displaceable, resilient C-shaped clamps at said proximal end of said second locking sleeve.

112. A catheter connection system as recited in claim 111, wherein said interior surface of said first compression sleeve radially, inwardly compresses a portion of the body wall of the selected dual lumen catheter against each of said prongs and urges said prongs toward each other, thereby to compress the partition wall between said prongs.

113. A catheter connection system as recited in claim 105, wherein the anchoring means comprises:

(a) a first set of engagement barbs radially, outwardly extending on said exterior surface of said stem and encircling said stem on said distal end of said stem, said first set of engagement barbs having a maximum outer diameter so sized as to fit within the lumen of the selected catheter when said distal end of said stem is received in the lumen of the selected catheter;

(b) a second set of engagement barbs radially, outwardly extending on said exterior surface of said stem and encircling said stem proximal of said first set of engagement barbs, said second set of engagement barbs having a maximum outer diameter larger than said first set of engagement barbs; and (c) a locking barb radially, outwardly extending on said exterior surface of said stem and encircling said stem between said second set of engagement barbs and the medical device, said locking barb having a maximum outer diameter that is larger than said maximum outer diameter of said second set of engagement barbs.

114. A catheter connection system as recited in claim 105, wherein said clinching means comprises a first fastening assembly, said first fastening assembly comprising:

a. a first locking sleeve having a proximal end, a distal end, and an interior surface defining a passageway longitudinally extending through said first locking sleeve, said interior surface of said first locking sleeve radially, inwardly compressing a portion of the body wall of the selected single lumen catheter against a portion of said anchoring means, when said distal of said stem is received in the lumen of the selected single lumen catheter and the selected single lumen catheter with said distal stem received therein is positioned within said passageway of said first locking sleeve; and b. an annular compression ring extending inwardly from said interior surface of said first locking sleeve.

115. A catheter connection system as recited in claim 114, wherein said compression ring is positioned at said proximal end of said first locking sleeve.

116. A catheter connection system as defined in claim 114, wherein said compression ring has an inner diameter larger than said maximum outer diameter of said locking barb of said anchoring means.

117. A catheter connection system as recited in claim 114, wherein said clinching means comprises a second fastening assembly, said second fastening assembly comprising:

a. a second locking sleeve having a distal end, a proximal end, and an interior surface defining a passageway extending therebetween;

b. a pliable first compression sleeve longitudinally disposed within said passageway of said second locking sleeve and having a distal end, a proximal end, and an interior surface defining a passageway longitudinally extending therethrough, said interior surface of said compression sleeve radially, inwardly compressing the body wall of the selected single lumen catheter against a portion of said anchoring means, when said distal end of said stem is received in the lumen of the selected single lumen catheter and the selected single lumen catheter with said distal end of said stem received therein is positioned within said passageway of said compression sleeve; and c. an opposing set of radially displaceable, resilient C-shaped clamps at said proximal end of said second locking sleeve.

118. A catheter connection system as recited in claim 117, wherein said C-shaped clamps have an inner diameter slightly smaller than said maximum outer diameter of said locking barb of said anchoring means.

119. A catheter connection system as recited in claim 117, wherein said clinching means comprises a third fastening assembly, said third fastening assembly comprising:

a. a third locking sleeve having a distal end, a proximal end, and an interior surface defining a passageway extending therebetween;

b. a pliable second compression sleeve longitudinally disposed within said passageway of said third locking sleeve and having a distal end, a proximal end, and an interior surface defining a passageway longitudinally extending therethrough, said second compression sleeve comprising:

i. a proximal portion at said proximal end of said second compression sleeve, said interior surface of said second compression sleeve at said proximal portion thereof being so sized and positioned as to encircle a proximal portion of said anchoring means, when said distal end of said stem is received within said passageway of said second compression sleeve; and ii. a distal portion at said distal end of said second compression sleeve, said distal portion of said second compression sleeve having an outer diameter smaller than the outer diameter of said proximal portion, said interior surface of said second compression sleeve at said distal portion thereof radially inwardly compressing the body wall of the third single lumen catheter against said distal portion of said anchoring means, when said distal end of said stem is received in the lumen of the second single lumen catheter and the second single lumen catheter with said distal end of said stem received therein is positioned within said passageway of said second compression sleeve; and c. an opposing set of radially displaceable, resilient C-shaped clamps positioned at said proximal end of said second locking sleeve.

120. A catheter connection system as recited in claim 105, wherein said stem comprises:

(a) a distal portion having an outer diameter on which said first set of engagement barbs are positioned; and (b) a proximal portion having an outer diameter larger than said outer diameter of said distal section, said second set of engagement barbs being positioned on said proximal section.

* * * * *

UNITED STATES PATENT AND TRADEMARK OFFICE
CERTIFICATE OF CORRECTION

PATENT NO. : 6,113,572
DATED : September 5, 2000
INVENTOR(S) : Gailey et al.

It is certified that error appears in the above-identified patent and that said Letters Patent is hereby corrected as shown below:

Title page,
Item [75] "Inventors," the city and state of residence for each of the following coinventors were changed in the Supplemental Declaration filed December 23, 1999, and should be:
-- Kelly J. Christian, Pocatello, ID; Kenneth Arden Eliasen, Queensbury, NY --.

Column 4,
Line 24, delete "in".

Column 5,
Line 2, change "system" to -- systems --; and
Line 47, delete "is" at beginning of line.

Column 6,
Line 32, change "the" to -- such a --, and change "such an" to -- the --.

Column 8,
Line 60, change "dissembled" to -- disassembled --.

Column 9,
Line 42, change "cross" to -- cross-section --, and after "of" insert -- the --.

Column 11,
Line 1, delete "formed"; and
Line 55, delete "to".

Column 12,
Line 48, change "sloping" to -- that slopes --.

Column 13,
Line 30, after "outwardly" insert -- . --.

Column 15,
Line 1, change "156" to -- 204 --.

UNITED STATES PATENT AND TRADEMARK OFFICE
CERTIFICATE OF CORRECTION

PATENT NO. : 6,113,572
DATED : September 5, 2000
INVENTOR(S) : Gailey et al.

It is certified that error appears in the above-identified patent and that said Letters Patent is hereby corrected as shown below:

Column 16,
Line 1, change "1sleeve 94" to -- 172 of compression --;
Line 2, change "radially,sleeve 94" to -- sleeve 94 --;
Line 6, after "a" insert -- distal --;
Line 15, delete "is"; and
Line 37, change "structures," to -- structure, --.

Column 18,
Line 62, change "an" to -- a --.

Column 19,
Line 24, after "engagement" insert -- barb --.

Column 21,
Line 2, change "primarily" to -- primary --;
Line 16, change "distince" to -- distinct --; and
Line 56, change "compressions" to -- compression --.

Column 24,
Line 66, change "select " to -- selected --.

Column 25,
Line 21, change "466" to -- 468 --.
Line 26, change "encircling" to -- encircles --; and
Line 58, change "references" to -- reference --.

Column 26,
Line 1, change "compress" to -- compresses --;
Line 14, change "character" to -- characters --; and
Line 61, change "FIG. 25" to -- FIG. 26 --.

Column 28,
Line 30, change "555" to -- 556 --; and
Line 37, change "joiner" to -- joinder --.

UNITED STATES PATENT AND TRADEMARK OFFICE
CERTIFICATE OF CORRECTION

PATENT NO. : 6,113,572
DATED : September 5, 2000
INVENTOR(S) : Gailey et al.

It is certified that error appears in the above-identified patent and that said Letters Patent is hereby corrected as shown below:

Column 29,
Line 58, change "56" to -- 58 --.

Column 30,
Line 15, change "connections" to -- connection --.

Column 31,
Line 41, before "56" insert -- assembly --;
Line 45, change "FIG." to "FIGS.";
Line 46, change "19" to -- 20-22 --;
Line 54, change "19-21" to -- 20-22 --; and
Line 63, change "connections" to -- connection --.

Column 33, claim 6,
Line 39, change "a" to -- an intermediate cylindrical --.

Column 36, claim 29,
Line 47, after "catheter" insert -- against --; and
Line 56, delete "second".

Column 42, claim 47,
Line 4, change "barbs and each of" to -- barb and --;
Line 5, change "barbs" to -- barb --; and
Line 7, change "an" to -- a first --.

Column 42, claim 48,
Line 13, change "said second" to -- a second --.

Column 43, claim 54,
Line 3, change "compressing a" to -- compress said --.

Column 48, claim 82,
Line 40, change "81" to -- 80 --.

Column 50, claim 89,
Line 45, change "rings" to -- ring --.

Column 52, claim 101,
Line 58, change "95" to -- 97 --.

UNITED STATES PATENT AND TRADEMARK OFFICE
CERTIFICATE OF CORRECTION

PATENT NO. : 6,113,572
DATED : September 5, 2000
INVENTOR(S) : Gailey et al.

It is certified that error appears in the above-identified patent and that said Letters Patent is hereby corrected as shown below:

Column 55, claim 106,
Line 17, change "connection" to -- conversion --.

Column 55, claim 107,
Line 25, change "connection" to -- conversion --.

Column 55, claim 108,
Line 43, change "connection" to -- conversion --.

Column 55, claim 109,
Line 46, change "connection" to -- conversion --.

Column 55, claim 110,
Line 49, change "connection" to -- conversion --.

Column 55, claim 111,
Line 55, change "connection" to -- conversion --.

Column 56, claim 112,
Line 11, change "connection" to -- conversion --.

Column 56, claim 113,
Line 17, change "connection" to -- conversion --.

Column 56, claim 114,
Line 38, change "connection" to -- conversion --.

Column 56, claim 115,
Line 54, change "connection" to -- conversion --.

Column 56, claim 116,
Line 57, change "connection" to -- conversion --; and
Line 57, change "defined" to -- recited --.

Column 56, claim 117,
Line 61, change "connection" to -- conversion --.

UNITED STATES PATENT AND TRADEMARK OFFICE
CERTIFICATE OF CORRECTION

PATENT NO. : 6,113,572
DATED : September 5, 2000
INVENTOR(S) : Gailey et al.

It is certified that error appears in the above-identified patent and that said Letters Patent is hereby corrected as shown below:

Column 57, claim 118,
Line 17, change "connection" to -- conversion --.

Column 57, claim 119,
Line 21, change "connection" to -- conversion --.

Column 58, claim 120,
Line 24, change "connection" to -- conversion --.

Signed and Sealed this

Twenty-second Day of January, 2002

Attest:

Attesting Officer

JAMES E. ROGAN
Director of the United States Patent and Trademark Office